United States Patent
Daniels et al.

(10) Patent No.: US 11,623,930 B2
(45) Date of Patent: Apr. 11, 2023

(54) IMIDAZODIAZEPINEDIONES AND METHODS OF USE THEREOF

(71) Applicant: Goldfinch Bio, Inc., Cambridge, MA (US)

(72) Inventors: Matthew H. Daniels, Somerville, MA (US); Maolin Yu, West Roxbury, MA (US); Jean-Christophe P. Harmange, Andover, MA (US); Thomas T. Tibbitts, Westford, MA (US); Mark W. Ledeboer, Acton, MA (US); Neil A. Castle, Cary, NC (US); Goran Malojcic, Boston, MA (US)

(73) Assignee: Goldfinch Bio, Inc., Cambridge, MA (US)

( * ) Notice: Subject to any disclaimer, the term of this patent is extended or adjusted under 35 U.S.C. 154(b) by 11 days.

(21) Appl. No.: 16/977,945

(22) PCT Filed: Mar. 5, 2019

(86) PCT No.: PCT/US2019/020732
§ 371 (c)(1),
(2) Date: Sep. 3, 2020

(87) PCT Pub. No.: WO2019/173327
PCT Pub. Date: Sep. 12, 2019

(65) Prior Publication Data
US 2021/0087200 A1    Mar. 25, 2021

Related U.S. Application Data

(60) Provisional application No. 62/638,448, filed on Mar. 5, 2018.

(51) Int. Cl.
| | | |
|---|---|---|
| *C07D 487/14* | (2006.01) | |
| *C07D 487/04* | (2006.01) | |
| *C07D 498/14* | (2006.01) | |
| *C07D 513/14* | (2006.01) | |

(52) U.S. Cl.
CPC ......... *C07D 487/14* (2013.01); *C07D 487/04* (2013.01); *C07D 498/14* (2013.01); *C07D 513/14* (2013.01)

(58) Field of Classification Search
CPC .................................................. C07D 487/14
USPC ....................................................... 514/220
See application file for complete search history.

(56) References Cited

U.S. PATENT DOCUMENTS

2009/0163545 A1    6/2009    Goldfarb

FOREIGN PATENT DOCUMENTS

| WO | WO-2014/143799 A2 | 9/2014 |
|---|---|---|
| WO | WO-2014/152287 A2 | 9/2014 |
| WO | WO-2019/173327 | 9/2019 |

OTHER PUBLICATIONS

Bridson et al., "Cyclic homologs of xanthines. I. Imidazo[4,5-e][1,4]diazepine-5,8-diones," Journal of Heterocyclic Chemistry, 25(4): 1179-1182 (1988).
Daly et al., "Imidazodiazepinediones: A New Class of Adenosine Receptor Antagonists," Journal of Medicinal Chemistry, 33: 2818-2821 (1990).
Extended European Search Report for EP Application No. 19763337.3 dated Oct. 21, 2021.
Ivanov., "Novel synthesis and reactions of 1,4,7-trimethyl-4,5,7,8-tetrahydro-6h-imidazo[4,5-e][1,4]diazepine-5,8-dione-a cyclic caffeine analog," Chemistry of Heterocyclic Compounds, 34: 719-722 (1998).
Conte-Camerino et al., "Enantiomers of clofibric acid analogs have opposite actions on rat skeletal muscle chloride channels," European Journal of Psychology, 413:105-107 (1988).
De Luca et al., "Opposite Effects of Enantiomers of Clofibric Acid Derivative on Rat Skeletal Muscle Chloride Conductance: Antagonism Studies and Theoretical Modeling of Two Different Receptor Site Interactions," The Journal of Pharmacology and Experimental Therapeutics, 260(1):364-368 (1992).

(Continued)

*Primary Examiner* — Taofiq A Solola
(74) *Attorney, Agent, or Firm* — Foley Hoag LLP; Dana M. Gordon

(57) ABSTRACT

Disclosed are compounds according to Formula (I) or (II), and pharmaceutical compositions comprising them. Also disclosed are therapeutic methods, e.g., of treating kidney diseases, using the compounds of Formula (I) or (II).

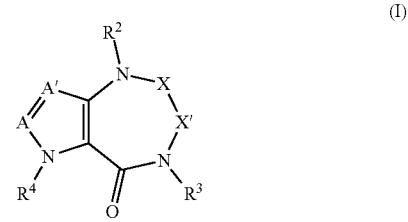

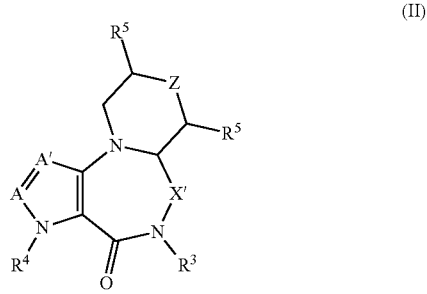

10 Claims, No Drawings
Specification includes a Sequence Listing.

(56) References Cited

OTHER PUBLICATIONS

Hof et al., "Stereoselectivity at the calcium channel: Opposite action of the enantiomers of a 1,4-dihydropyridine," Journal of Cardiovascular Pharmacology, 7:689-693 (1985).
Huang et al., "Discovery of MK-8318, a potent and selective CRTh2 receptor antagonist for the treatment of asthma," ACS Med Chem Lett, 9:679-684 (2018).
International Search Report and Written Opinion for International Application No. PCT/US2019/020732 dated Jul. 19, 2019.
Kim et al., "5-HT7 receptor modulators: Amino groups attached to biphenyl scaffold determine functional activity," European Journal of Medicinal Chemistry, 123:180-190 (2016).
Pubchem, Substance Record for SID 163049317. Available Date: May 22, 2013. [retrieved on Jul. 5, 2019]. Retrieved from the Internet: <http://pubchem.ncbi.nlm.nih.gov/substance/163049317>.
Pubchem, Substance Record for SID 74851019. Available Date: Jun. 11, 2009. [retrieved on May 9, 2019]. Retrieved from the Internet: <http://pubchem.ncbi.nlm.nih.gov/substance/74851019>.
Recio et al., "Design, synthesis and biological studies of a library of NK1-receptor Ligands Based on a 5-srylthiosubstituted 2-amino-4,6-diaryl-3-cyano-4H-pyran core: Switch from antagonist to agonist effect by chemical modification," European Journal of Medicinal Chemistry, 138:644-660 (2017).
Rubaiy et al., "Identification of an (-)-englerin A analogue, which antagonizes (-)-englerin A at TRPC1/4/5 channels," British Journal of Pharmacology, 175(5):830-839 (2018).
Alawi et al., "Transient receptor potential canonical 5 channels plays an essential role in hepatic dyslipidemia associated with cholestasis," Nature Scientific Reports, 7: 2338 (9 pages)(2017).
Gaunt et al., "Transient receptor potential canonical 4 and 5 proteins as targets in cancer therapeutics," Eur Biophys J, 45: 611 -620 (2016).
Just et al., "Treatment with HC-070, a potent inhibitor of TRPC4 and TRPC5, leads to anxiolytic and antidepressant effects in mice," Plos One, 13(1): e0191225 (32 pages)(2018).
Ma et al., "Transient receptor potential channel TRPC5 is essential for P-glycoprotein induction in drug-resistant cancer cells," PNAS, 109(40): 16282-16287 (2012).
Patani et al., "Bioisosterism: A Rational Approach in Drug Design," Chemical Reviews 96(8): 3147-3176(1996).
Sachdeva et al., "TRPC proteins contribute to development of diabetic retinopathy and regulate glyoxalase 1 activity and methylglyoxal accumulation," Molecular Metabolism, 9, 156-167 (2018).
Schaldecker et al., "Inhibition of the TRPC5 ion channel protects the kidney filter," J Clin Invest., 123(12):5298-5309 (2013).
Wei et al., "Regulation of neuropathic pain behavior by amygdaloid TRPC4/C5 channels," Neuroscience Letters, 608: 12-17 (2015).
Wei et al., "Therapeutic Effects of FK506 on IgA Nephropathy Rat," Kidney & Blood Pressure Research, 42: 983-998 (2017).
Westlund et al., "A Rat Knockout Model Implicates TRPC4 In Visceral Pain Sensation," Neuroscience, 262: 165-175 (2014).
Zhou et al., "A small-molecule inhibitor of TRPC5 ion channels suppresses progressive kidney disease in animal models," Science, 358:1332-1336 (2017).
Zhou et al., "Human relevance of blocking the Rac1-TRPC5 pathway as a podocyte-protective strategy for progressive kidney diseases," bioRxiv: 41 pages (2020).

IMIDAZODIAZEPINEDIONES AND METHODS OF USE THEREOF

RELATED APPLICATIONS

This application is a § 371 national stage application based on International Application No. PCT/US19/20732, filed Mar. 5, 2019; which claims the benefit of U.S. Provisional Application 62/638,448, filed Mar. 5, 2018.

INCORPORATION-BY-REFERENCE OF SEQUENCE LISTING

The contents of the sequence listing text file named "GFX-00901_SL.txt", which was created on Jan. 12, 2023, and is 11,636 bytes in size, is hereby incorporated by reference in its entirety.

BACKGROUND

Proteinuria is a condition in which an excessive amount of protein in the blood leaks into the urine. Proteinuria can progress from a loss of 30 mg of protein in the urine over a 24-hour period (called microalbuminuria) to >300 mg/day (called macroalbuminuria), before reaching levels of 3.5 grams of protein or more over a 24-hour period, or 25 times the normal amount. Proteinuria occurs when there is a malfunction in the kidney's glomeruli, causing fluid to accumulate in the body (edema). Prolonged protein leakage has been shown to result in kidney failure. Nephrotic Syndrome (NS) disease accounts for approximately 12% of prevalent end stage renal disease cases at an annual cost in the United States of more than $3 billion. Approximately 5 out of every 100,000 children are diagnosed with NS each year, and 15 out of every 100,000 children are living with it today. Even for patients who respond positively to treatment the relapse frequency is extremely high. About 90% of children with Nephrotic Syndrome will respond to treatment; however, an estimated 75% will relapse. Therefore, more effective methods of treating, or reducing risk of developing, kidney disease, e.g., proteinuria, are required.

Mammalian TRP channel proteins form six-transmembrane cation-permeable channels that may be grouped into six subfamilies on the basis of amino acid sequence homology (TRPC, TRPV, TRPM, TRPA, TRPP, and TRPML). Recent studies of TRP channels indicate that they are involved in numerous fundamental cell functions and are considered to play an important role in the pathophysiology of many diseases. Many TRPs are expressed in kidney along different parts of the nephron, and growing evidence suggest that these channels are involved in hereditary as well as acquired kidney disorders. For example, TRPC6, TRPM6, and TRPP2 have been implicated in hereditary focal segmental glomerulosclerosis (FSGS), hypomagnesemia with secondary hypocalcemia (HSH), and polycystic kidney disease (PKD), respectively. TRPC5 has also been reported to contribute to the mechanisms underlying regulation of innate fear responses. (J Neurosci. 2014 Mar. 5; 34(10): 3653-3667).

Hence, there is a need for additional inhibitors of TRPC5.

SUMMARY

The invention is based, at least in part, on the discovery that Transient Receptor Potential Cation Channel, subfamily C, member 5 (TRPC5) activity abolishes actin stress fibers and diminishes focal adhesion formation, rendering a motile, migratory podocyte phenotype.

In one aspect, the invention relates to small molecule TRPC5 modulators.

In some embodiments, the invention relates to small molecule TRPC5 inhibitors and the use of such inhibitors in methods of treating, or reducing risk of developing, kidney disease (e.g., proteinuria, microalbuminuria, macroalbuminuria), anxiety, depression, or cancer, comprising administering to a subject in need thereof.

In some embodiments, the invention relates to small molecule TRPC5 agonists and the use of such agonists in methods of treating, or reducing risk of developing, obesity.

The interaction of small molecule ligands with proteins can lead to agonist or antagonist (inhibitory) activity. The structural determinants that lead to agonistic or antagonistic activity are often not well understood. Opposing effects of closely related molecules, even enantiomers, on the activity of their biological target has been observed in multiple cases over decades of research. It is particularly common in membrane signaling proteins, such as ion channels and GPCR's (X. Huang et al., ACS Med. Chem. Lett. 2018, 9, 679-684; R. Recio et al., Eur J Med Chem 2017, 138, 644-660; Y. Kim et al., Eur J Med Chem 2016, 123, 180-190). Examples of this behavior include the modulation of calcium channels, such as DHP receptors (G. C. Rovnyak et al., J Med Chem. 1995, 38(1):119-29, from Neil's email), calcium channels in heart cells (RS Kass, Circ Res 1987, 61(4 Pt 2), 11-5 and others (R. P. Hof et al., J Cardiovasc Pharmacol. 1985, 7(4):689-93). These references highlight how small structural features govern whether a compound can act as either an agonist or antagonist. Very recently, such a phenomenon was described for TRPC1/4/5 channels (H. N. Rubaiy et al., Br J Pharmacol. 2018, 175(5):830-839. doi: 10.1111/bph.14128. Epub 2018 Jan. 25). In accordance with such literature reports, we found that Formula I and Formula II described herein include both agonists and inhibitors. One of ordinary skill in the art can easily determine if a compound of Formula I or Formula II is a TRPC5 agonist or inhibitor by testing it in the FLIPR assays described herein or any other assays that can determine if a compound is a TRPC5 inhibitor or a TRPC5 agonist.

The therapeutic methods described above are effective for a variety of subjects including mammals, e.g., humans and other mammals, such as mice, rats, rabbits, and monkeys, and domesticated and farm mammals, e.g., cats, dogs, goats, sheep, pigs, cows, or horses.

In some embodiments, a compound of the invention is a compound of Formula (I) or (II), or a pharmaceutically acceptable salt thereof;

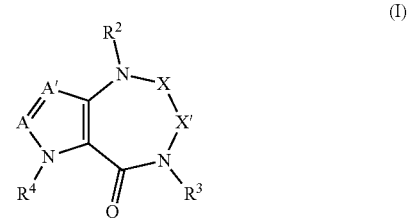

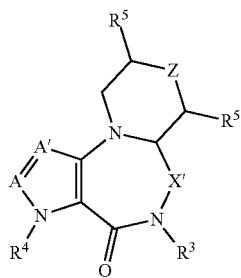

(II)

wherein
A and A' are independently selected from CR and N;
R is L-R$^1$;
L is absent, CH$_2$, O, SO$_2$, or NR$^2$;
R$^1$ is selected from optionally substituted alkyl, optionally substituted aryl, and optionally substituted heteroaryl;
each R$^2$ is independently H, or alkyl;
R$^3$ is selected from optionally substituted alkyl, optionally substituted alkylene-OR$^2$, optionally substituted cycloalkylene-OR$^2$, optionally substituted alkylene-N(R$^7$)$_2$, optionally substituted cycloalkylene-N(R$^7$)$_2$, optionally substituted alkylene-C(O)N(R$^2$)$_2$, optionally substituted cycloalkylene-C(O)N(R$^2$)$_2$, optionally substituted alkylene-S(O)$_2$N(R$^2$)$_2$, and optionally substituted cycloalkylene-S(O)$_2$N(R$^2$)$_2$;
R$^4$ is selected from alkyl, optionally substituted alkylene-aryl, and optionally substituted alkylene-heteroaryl;
each R$^5$ is independently selected from H, N(R$^2$)$_2$, OR$^2$;
each R$^7$ is independently selected from H, alkyl, (alkyl)C(O)—, (aryl)C(O)—, (alkyl)S(O)$_2$—, and (aryl)S(O)$_2$—;
X is —C(O)—, CH$_2$, CHR$^6$, C(R$^6$)$_2$;
each R$^6$ is independently selected from H, alkyl, and optionally substituted alkylene-OH;
X' is —C(O)—, CH$_2$, CHR$^{3'}$, C(R$^{3'}$)$_2$, or X' is taken together with R$^3$ to form a 5- or 6-membered ring;
each R$^{3'}$ is independently selected from optionally substituted alkyl, optionally substituted alkylene-OR$^2$, optionally substituted cycloalkylene-OR$^2$, optionally substituted alkylene-N(R$^7$)$_2$, optionally substituted cycloalkylene-N(R$^7$)$_2$, optionally substituted alkylene-C(O)N(R$^2$)$_2$, optionally substituted cycloalkylene-C(O)N(R$^2$)$_2$, optionally substituted alkylene-S(O)$_2$N(R$^2$)$_2$, and optionally substituted cycloalkylene-S(O)$_2$N(R$^2$)$_2$; and
Z is absent, CH$_2$, CHR$^5$, O, —NR$^2$—, or —SO$_2$—;
provided that X and X' are not both —C(O)—, and R$^5$ is H when Z is O, NR or SO$_2$.

In one aspect, the invention features a composition, comprising a compound of any one of Formula (I) or (II) or a pharmaceutically acceptable salt thereof; and a pharmaceutically acceptable excipient.

In one aspect, the invention features methods of treating, or the reducing risk of developing, a kidney disease, diabetic retinopathy, anxiety, depression, or cancer, comprising administering to a subject in need thereof a therapeutically effective amount of a compound of Formula (I) or (II). In certain embodiments, a kidney disease is treated or the risk of developing a kidney disease is reduced. In certain embodiments, a kidney disease is treated. In certain embodiments, the kidney disease is selected from the group consisting of Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, and IgA nephropathy. In certain embodiments, the kidney disease is proteinuria. In certain embodiments, the kidney disease is microalbuminuria or macroalbuminuria.

In some embodiments, the invention features methods of treating, or the reducing risk of developing, obesity.

In certain embodiments, the subject is a mammal. In certain embodiments, the mammal is a human.

In some embodiments, the invention comprises administering the compound of Formula (I) or (II) to a mammal and evaluating an effect of the compound on calcium transport, wherein a compound that reduces or inhibits calcium transport is a therapeutic agent for treating or reducing risk of developing a kidney disease, anxiety, depression, or cancer.

The invention provides several advantages. The prophylactic and therapeutic methods described herein are effective in treating kidney disease, e.g., proteinuria, and have minimal, if any, side effects. Further, methods described herein are effective to identify compounds that treat or reduce risk of developing a kidney disease, anxiety, depression, or cancer.

Other features, objects, and advantages of the invention will be apparent from the detailed description, and from the claims.

DETAILED DESCRIPTION

Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

Unless otherwise specified, "alkylene" by itself or as part of another substituent refers to a saturated straight-chain or branched divalent group having the stated number of carbon atoms and derived from the removal of two hydrogen atoms from the corresponding alkane. Examples of straight chained and branched alkylene groups include —$CH_2$— (methylene), —$CH_2$—$CH_2$-(ethylene), —$CH_2$—$CH_2$—$CH_2$— (propylene), —$C(CH_3)_2$—, —$CH_2$—$CH(CH_3)$—, —$CH_2$—$CH_2$—$CH_2$—$CH_2$—$CH_2$—$CH_2$—$CH_2$—$CH_2$—$CH_2$— (pentylene), —$CH_2$—$CH(CH_3)$—$CH_2$—, and —$CH_2$—$C(CH_3)_2$—$CH_2$—.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. Co alkyl indicates a hydrogen where the group is in a terminal position, a bond if internal. The terms "$C_{2-y}$ alkenyl" and "$C_{2-y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS-.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

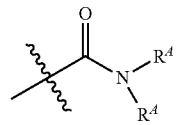

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, aryls, heteroaryls, and/or heterocyclyls. Aryl groups include benzene, naphthalene, phenanthrene, phenol, aniline, and the like.

The term "carbamate" is art-recognized and refers to a group

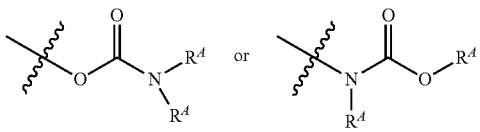

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group —OCO$_2$—$R^A$, wherein $R^A$ represents a hydrocarbyl group.

The term "carboxy", as used herein, refers to a group represented by the formula —CO$_2$H.

The term "ester", as used herein, refers to a group —C(O)OR$^A$ wherein $R^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "heterocyclylalkyl" or "heterocycloalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

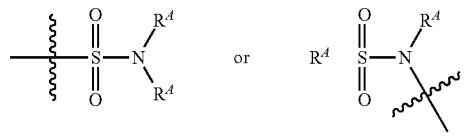

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —$S(O)$—$R^A$, wherein $R^A$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^A$, wherein $R^A$ represents a hydrocarbyl.

The term "thioalkyl", as used herein, refers to an alkyl group substituted with a thiol group.

The term "thioester", as used herein, refers to a group —$C(O)SR^A$ or —$SC(O)R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

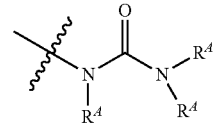

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3$^{rd}$ Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "treating" includes prophylactic and/or therapeutic treatments. The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The phrases "conjoint administration" and "administered conjointly" refer to any form of administration of two or more different therapeutic compounds such that the second compound is administered while the previously administered therapeutic compound is still effective in the body (e.g., the two compounds are simultaneously effective in the patient, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, an individual who receives such treatment can benefit from a combined effect of different therapeutic compounds.

The term "prodrug" is intended to encompass compounds which, under physiologic conditions, are converted into the therapeutically active agents of the present invention. A common method for making a prodrug is to include one or more selected moieties which are hydrolyzed under physiologic conditions to reveal the desired molecule. In other embodiments, the prodrug is converted by an enzymatic activity of the host animal. For example, esters or carbonates (e.g., esters or carbonates of alcohols or carboxylic acids) are preferred prodrugs of the present invention. In certain embodiments, some or all of the compounds of the invention in a formulation represented above can be replaced with the corresponding suitable prodrug, e.g., wherein a hydroxyl in the parent compound is presented as an ester or a carbonate or carboxylic acid present in the parent compound is presented as an ester.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

In some embodiments, a "small molecule" refers to an organic, inorganic, or organometallic compound typically having a molecular weight of less than about 1000. In some embodiments, a small molecule is an organic compound, with a size on the order of 1 nm. In some embodiments, small molecule drugs of the invention encompass oligopeptides and other biomolecules having a molecular weight of less than about 1000.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Compounds of the Invention

One aspect of the invention provides small molecule modulators of TRPC5. In some embodiments, the invention provides small molecule inhibitors of TRPC5. In some embodiments, the invention provides small molecule agonists of TRPC5.

In some embodiments, the compound of the invention is a compound of Formula (I) or (II), or a pharmaceutically acceptable salt thereof;

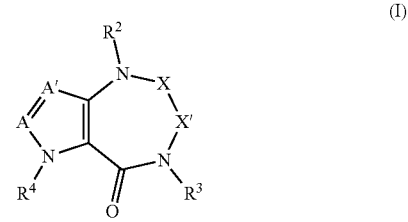

(I)

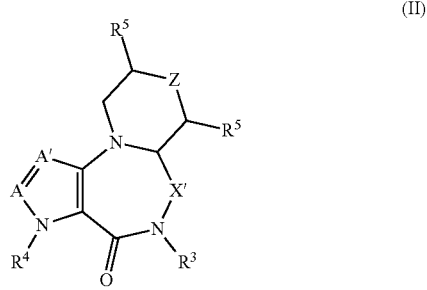

(II)

wherein
A and A' are independently selected from CR and N;
R is L-R$^1$;
L is absent, CH$_2$, O, SO$_2$, or NR$^2$;
R$^1$ is selected from optionally substituted alkyl, optionally substituted aryl, and optionally substituted heteroaryl, and when L is absent, R$^1$ is additionally selected from H;
each R$^2$ is independently H, or alkyl;
R$^3$ is selected from optionally substituted alkyl, optionally substituted alkylene-OR$^2$, optionally substituted cycloalkylene-OR$^2$, optionally substituted alkylene-N(R$^7$)$_2$, optionally substituted cycloalkylene-N(R$^7$)$_2$, optionally substituted alkylene-C(O)N(R$^2$)$_2$, optionally substituted cycloalkylene-C(O)N(R$^2$)$_2$, optionally substituted alkylene-S(O)$_2$N(R$^2$)$_2$, and optionally substituted cycloalkylene-S(O)$_2$N(R$^2$)$_2$;
R$^4$ is selected from alkyl, optionally substituted alkylene-aryl, and optionally substituted alkylene-heteroaryl;
each R$^5$ is independently selected from H, N(R$^2$)$_2$, OR$^2$;
each R$^7$ is independently selected from H, alkyl, (alkyl)C(O)—, (aryl)C(O)—, (alkyl)S(O)$_2$—, and (aryl)S(O)$_2$—;
X is —C(O)—, CH$_2$, CHR$^6$, C(R$^6$)$_2$;
each R$^6$ is independently selected from H, alkyl, and optionally substituted alkylene-OH;
X' is —C(O)—, CH$_2$, CHR$^{3'}$, C(R$^{3'}$)$_2$, or X' is taken together with R$^3$ to form a 5- or 6-membered ring;
each R$^{3'}$ is independently selected from optionally substituted alkyl, optionally substituted alkylene-OR$^2$, optionally substituted cycloalkylene-OR$^2$, optionally substituted alkylene-N(R$^7$)$_2$, optionally substituted cycloalkylene-N(R$^7$)$_2$, optionally substituted alkylene-C(O)N(R$^2$)$_2$, optionally substituted cycloalkylene-C(O)N(R$^2$)$_2$, optionally substituted alkylene-S(O)$_2$N(R$^2$)$_2$, and optionally substituted cycloalkylene-S(O)$_2$N(R$^2$)$_2$; and
Z is absent, CH$_2$, CHR$^5$, O, —NR$^2$—, or —SO$_2$—;
provided that X and X' are not both —C(O)—, and R$^5$ is H when Z is O, NR or SO$_2$.

In some embodiments, the compound is a compound of Formula (I). In some embodiments, the compound is a compound of Formula (II).

In some embodiments, at least one of A and A' is CR.

In some embodiments, A is N. In some embodiments, A is CR.

In some embodiments, A' is N. In some embodiments, A' is CR.

In some embodiments, A' is N and A is CR.

In some embodiments, R is L-R$^1$.

In some embodiments, L is absent. In some embodiments, when L is absent, R$^1$ is additionally selected from H. In some embodiments, L is CH$_2$. In some embodiments, L is O. In some embodiments, L is SO$_2$. In some embodiments, L is NR$^2$.

In some embodiments, R$^1$ is optionally substituted aryl. In some embodiments, R' is optionally substituted phenyl. In some embodiments, R$^1$ is substituted phenyl. In some embodiments, the substituted phenyl is substituted with one or more substituents independently selected from halogen, —CF$_3$, —C(H)F$_2$, and —OCF$_3$.

In some embodiments, R$^1$ is optionally substituted alkyl. In some embodiments, alkyl is selected from methyl, ethyl, n-propyl, iso-propyl, n-butyl, iso-butyl, and tert-butyl.

In some embodiments, R$^1$ is optionally substituted heteroaryl. In some embodiments, R$^1$ is substituted heteroaryl substituted with one or more substituents independently selected from halogen, —CF$_3$, —C(H)F$_2$, and —OCF$_3$.

In some embodiments, L is O and R$^1$ is 3-chlorophenyl, 3-fluorophenyl, 3-trifluoromethoxyphenyl, isopropyl, or n-propyl.

In some embodiments, R$^2$ is H. In some embodiments, R$^2$ is alkyl. In some embodiments, R$^2$ is selected from methyl, ethyl, n-propyl, iso-propyl, n-butyl, iso-butyl, and tert-butyl. In some embodiments, R$^2$ is methyl.

In some embodiments, R$^3$ is optionally substituted alkyl. In some embodiments, R$^3$ is optionally substituted alkylene-OR$^2$. In some embodiments, R$^3$ is optionally substituted cycloalkylene-OR$^2$. In some embodiments, R$^3$ is optionally substituted alkylene-N(R$^7$)$_2$. In some embodiments, R$^3$ is optionally substituted cycloalkylene-N(R$^7$)$_2$. In some embodiments, R$^3$ is optionally substituted alkylene-C(O)N(R$^2$)$_2$. In some embodiments, R$^3$ is optionally substituted cycloalkylene-C(O)N(R$^2$)$_2$. In some embodiments, R$^3$ is optionally substituted alkylene-S(O)$_2$N(R$^2$)$_2$. In some embodiments, R$^3$ is optionally substituted cycloalkylene-S(O)$_2$N(R$^2$)$_2$. In some embodiments, R$^3$ is methyl, 2-hydroxyethyl, 2,3-dihydroxypropyl, 2,2-difluoro-3-hydroxypropyl, 3-hydroxypropyl, 3-methoxypropyl, 3-hydroxycyclobutyl, or 3-hydroxycyclopentyl.

In some embodiments, one instance of R$^7$ is H; and the second instance of R$^7$ is alkyl, (alkyl)C(O)—, (aryl)C(O)—, (alkyl)S(O)$_2$—, or (aryl)S(O)$_2$—. In some embodiments, one instance of R$^7$ is alkyl; and the second instance of R$^7$ is H, (alkyl)C(O)—, (aryl)C(O)—, (alkyl)S(O)$_2$—, or (aryl)S(O)$_2$—. In some embodiments, both instances of R$^7$ are H. In some embodiments, both instances of R$^7$ are alkyl.

In some embodiments, R$^3$ is selected from

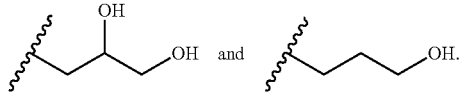 [SMILES: *CC(O)CO ; "and" ; *CCCO]

In some embodiments, R$^3$ is

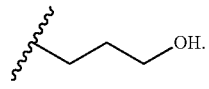 [SMILES: *CCCO]

In some embodiments, R$^3$ is selected from

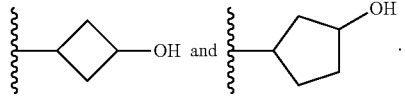 [SMILES: *C1CC(O)C1 ; "and" ; *C1CCC(O)C1 ; "."]

In some embodiments, R$^3$ is selected from

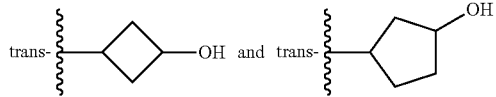

In some embodiments, R$^4$ is alkyl. In some embodiments, R$^4$ is selected from methyl, ethyl, n-propyl, iso-propyl, n-butyl, iso-butyl, and tert-butyl. In some embodiments, R$^4$ is selected from n-butyl, iso-butyl, and tert-butyl. In some embodiments, R$^4$ is n-butyl.

In some embodiments, R$^4$ is optionally substituted alkylene-aryl. In some embodiments, the alkylene of alkylene-aryl is substituted. In some embodiments, aryl of alkylene-aryl is substituted. In some embodiments, substituted aryl is substituted with halogen, —CF$_3$, —C(H)F$_2$, or —OCF$_3$. In some embodiments, aryl of alkylene-aryl is optionally substituted phenyl. In some embodiments, phenyl is substituted with one or more instances of halogen. In some embodiments, alkylene of alkylene-aryl is methylene. In some embodiments, R$^4$ is optionally substituted alkylene-heteroaryl.

In some embodiments, R$^4$ is n-butyl, 4-chlorobenzyl, or 2-(4-chlorophenyl)ethan-2-yl.

In some embodiments, R$^4$ is

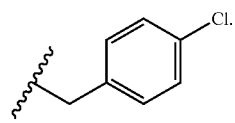 [SMILES: *Cc1ccc(Cl)cc1]

In some embodiments, R$^4$ is

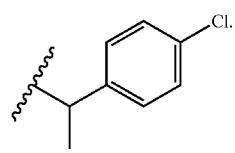 [SMILES: *C(C)c1ccc(Cl)cc1]

In some embodiments, R$^4$ is

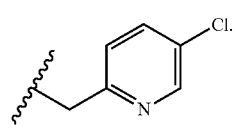

In some embodiments, each R$^5$ is H. In some embodiments, one R$^5$ is hydrogen and the other R$^5$ is —O-alkyl. In some embodiments, one R$^5$ is hydrogen and the other R$^5$ is —OMe. In some embodiments, one R$^5$ is hydrogen and the other R$^5$ is —OH. In some embodiments, one R$^5$ is hydrogen and the other R$^5$ is —NMe$_2$. In some embodiments, one R$^5$ is hydrogen and the other R$^5$ is —NH$_2$.

In some embodiments, X is —C(O)—. In some embodiments, X is CH$_2$. In some embodiments, X is —CHR$^6$—. In some embodiments, X is —C(R$^6$)$_2$—. In some embodiments, R$^6$ is alkyl. In some embodiments, R$^6$ is selected from methyl, ethyl, n-propyl, iso-propyl, n-butyl, iso-butyl, and tert-butyl. In some embodiments, R$^6$ is methyl. In some embodiments, R$^6$ is optionally substituted alkylene-OH. In some embodiments, R$^6$ is optionally substituted ethylene-OH. In some embodiments, R$^6$ is substituted ethylene-OH. In some embodiments, R$^6$ is H.

In some embodiments, X' is —C(O)—. In some embodiments, X' is CH$_2$.

In some embodiments, X' is —CHR$^{3'}$—. In some embodiments, X' is —C(R$^{3'}$)$_2$—. In some embodiments, R$^{3'}$ is alkyl. In some embodiments, R$^{3'}$ is selected from methyl, ethyl, n-propyl, iso-propyl, n-butyl, iso-butyl, and tert-butyl. In some embodiments, R$^{3'}$ is methyl. In some embodiments, R$^{3'}$ is optionally substituted alkylene-OH. In some embodiments, R$^{3'}$ is optionally substituted ethylene-OH. In some embodiments, R$^{3'}$ is substituted ethylene-OH.

In some embodiments, Z is absent. In some embodiments, Z is CH$_2$. In some embodiments, Z is —N(alkyl)-. In some embodiments, Z is selected from —N(n-butyl)-, —N(iso-butyl)-, and —N(tert-butyl)-. In some embodiments, Z is —SO$_2$—. In some embodiments, Z is absent and each R$^5$ is hydrogen.

In some embodiments, the compound is selected from:

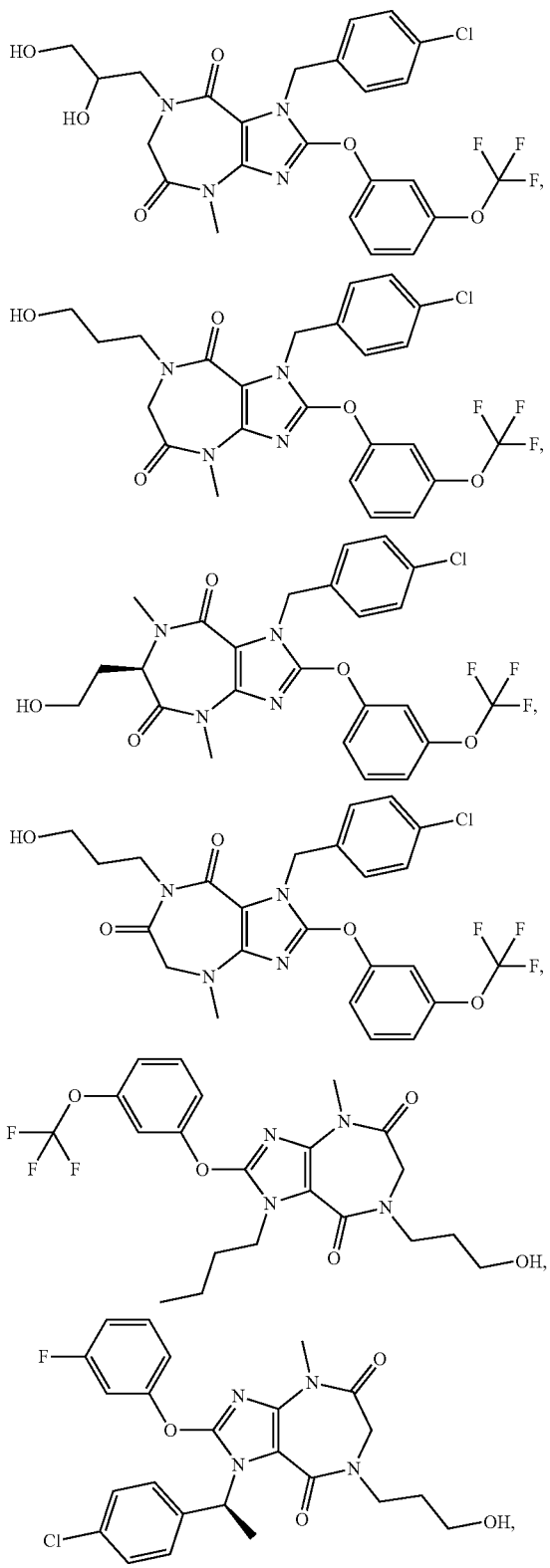

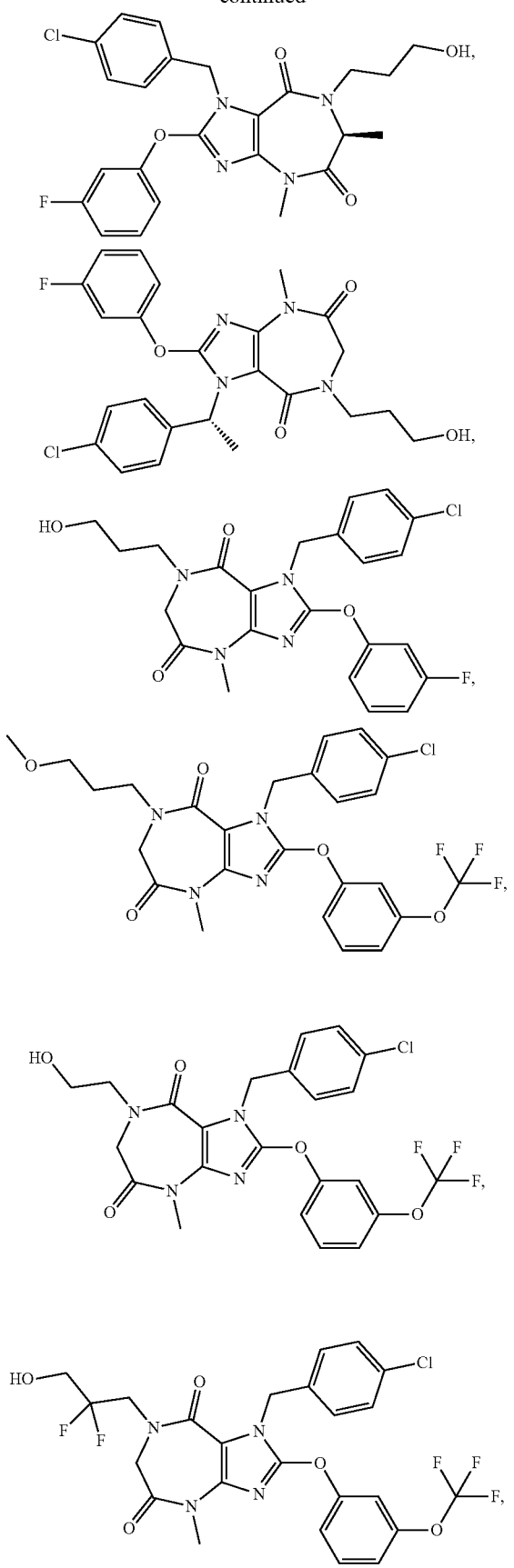
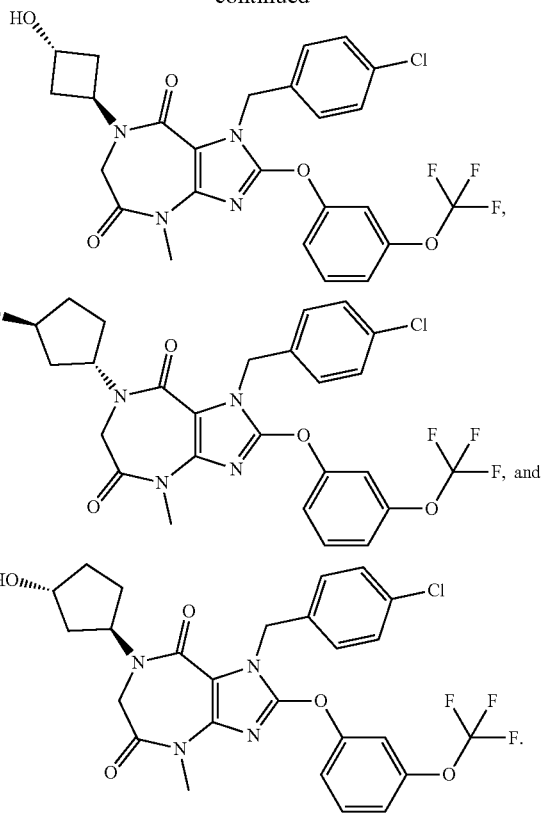
In some embodiments, the compound is:
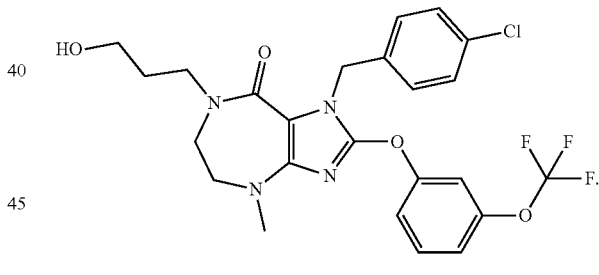
In some embodiments, the compound is:
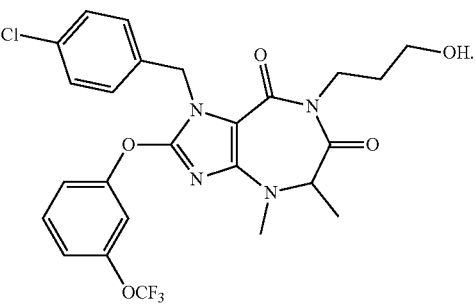 [SMILES: CC1C(=O)N(CCCO)C(=O)c2c(nc(Oc3cccc(OC(F)(F)F)c3)n2Cc2ccc(Cl)cc2)N1C]

In some embodiments, the compound is selected from:
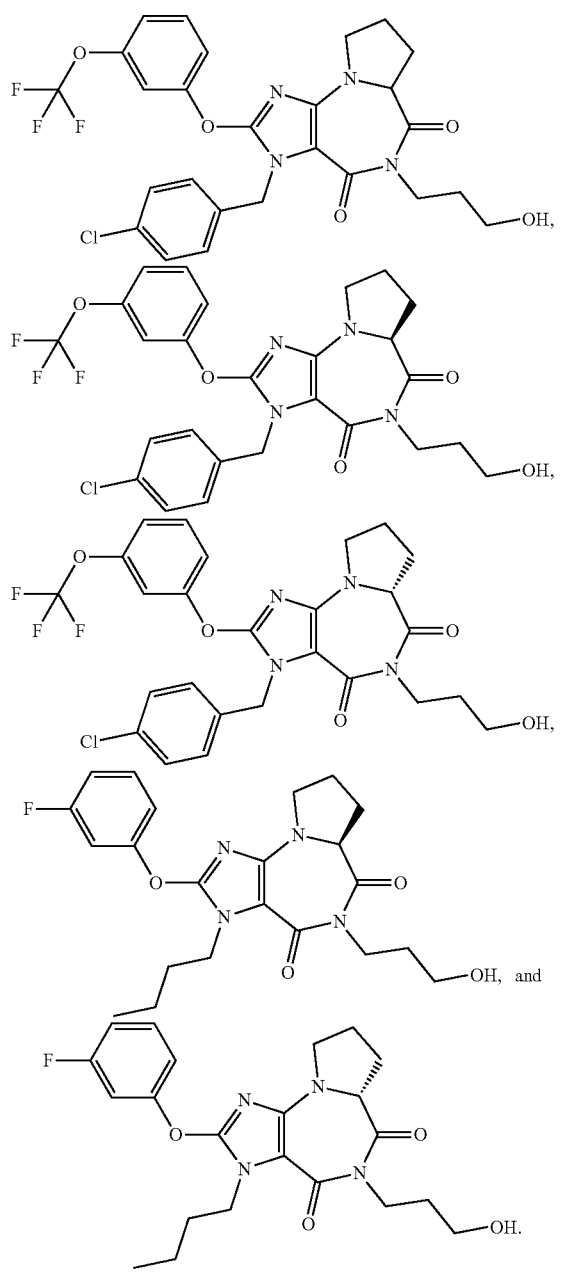
In some embodiments, the compound is selected from:
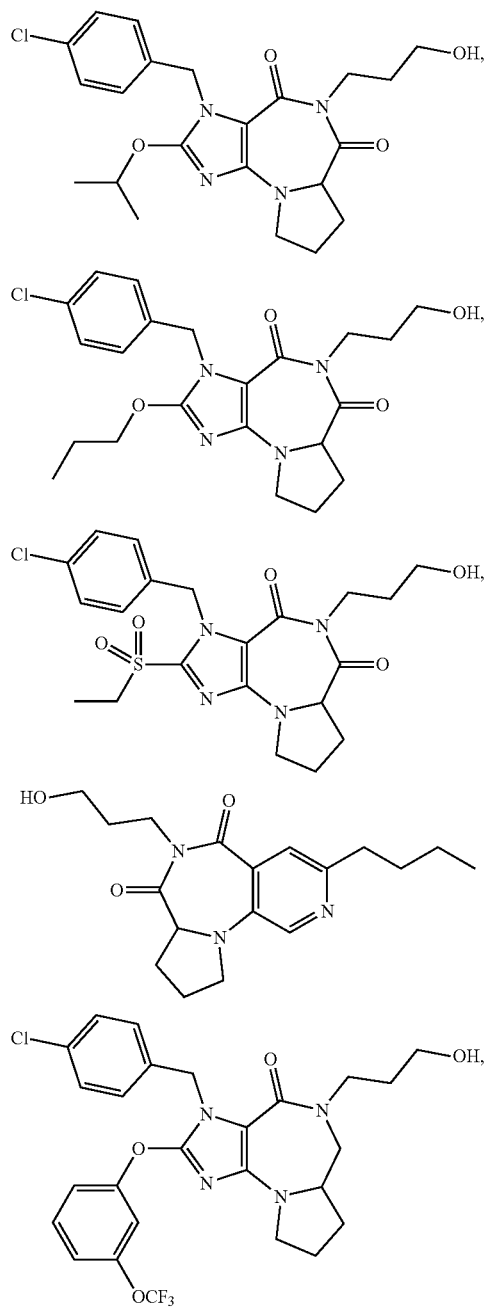
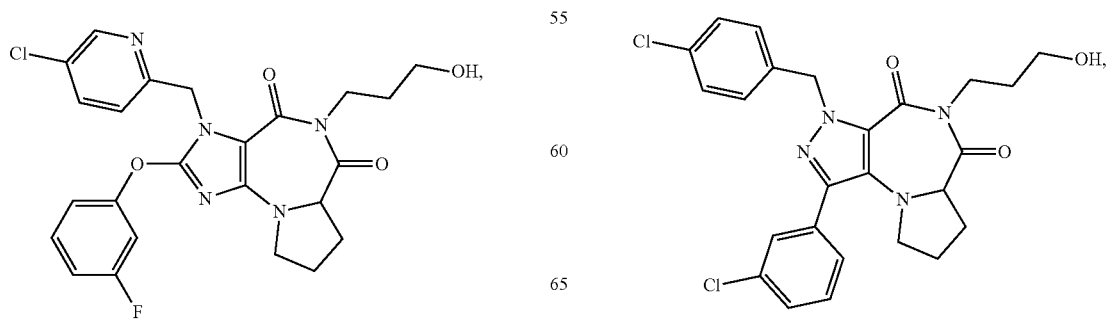

-continued
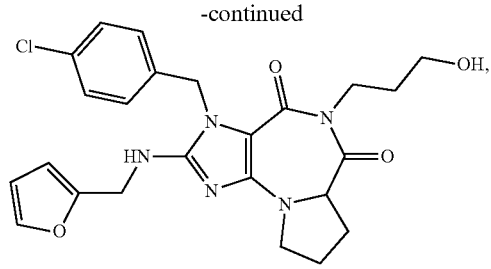
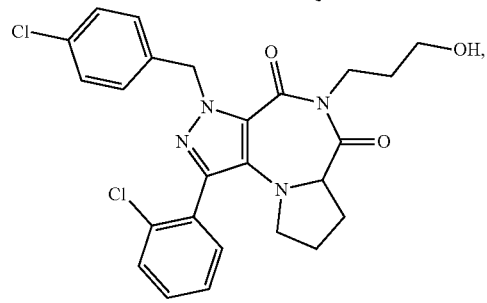
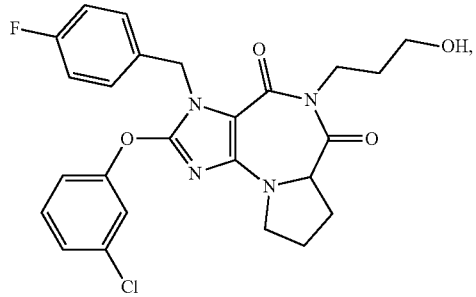
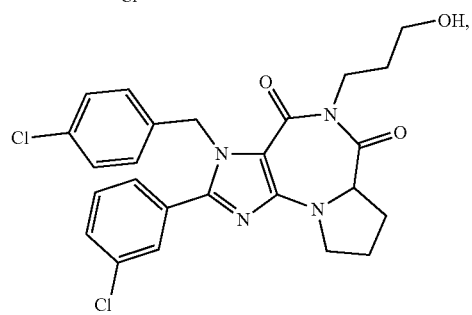
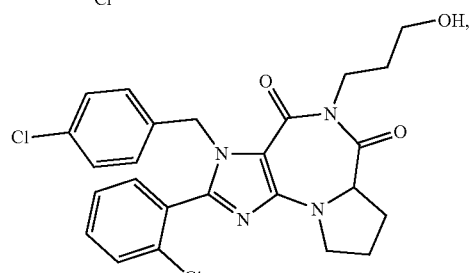
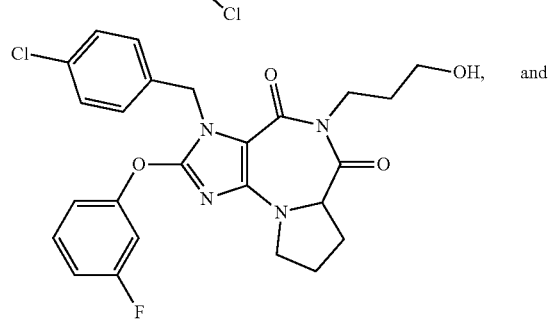
-continued
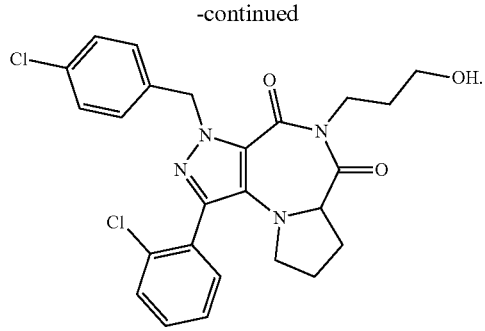
In some embodiments, wherein the compound is selected from:
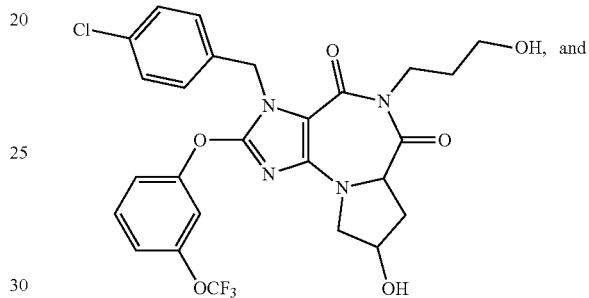
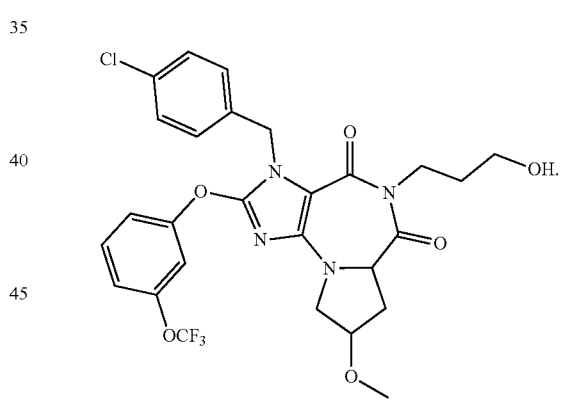
In some embodiments, the compound is:
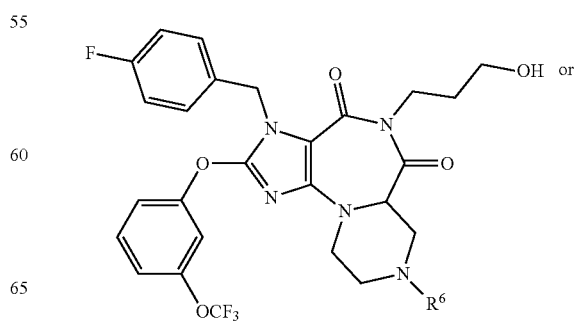

-continued
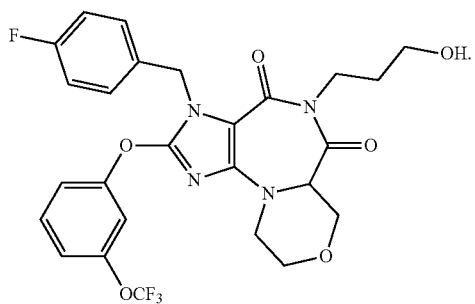
In some embodiments, the compound is:
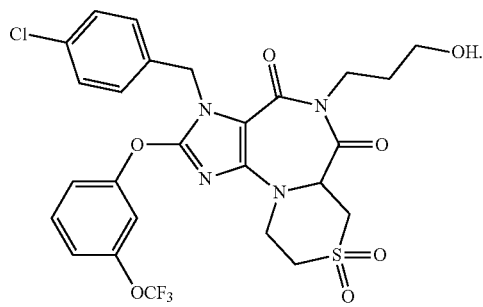 [SMILES: O=C1c2c(nc(Oc3cccc(OC(F)(F)F)c3)n2Cc2ccc(Cl)cc2)N2CCS(=O)(=O)CC2C(=O)N1CCCO]
In some embodiments, the compound is:
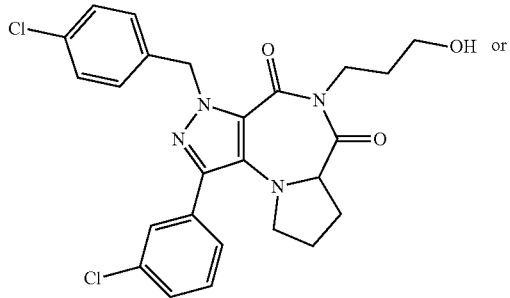
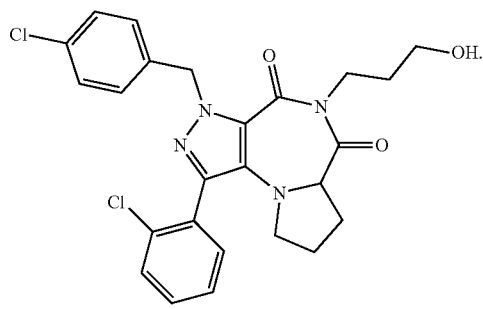
In some embodiments, the compound is:
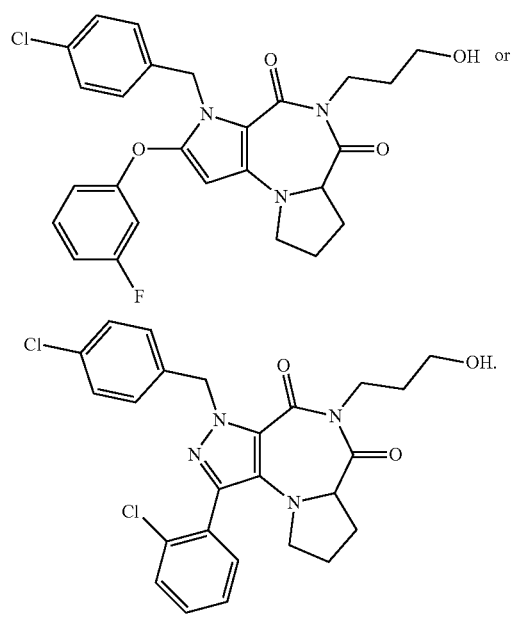
In some embodiments, the compound is:
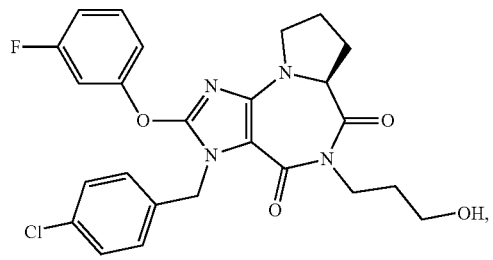
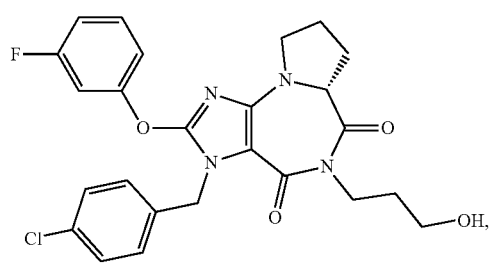
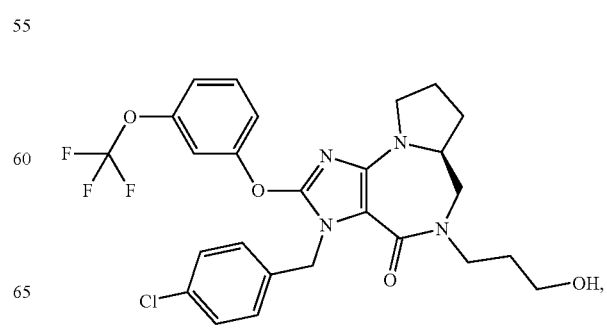

-continued

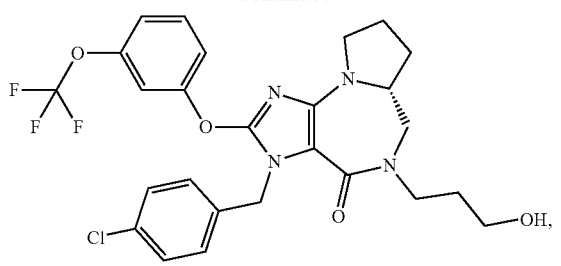

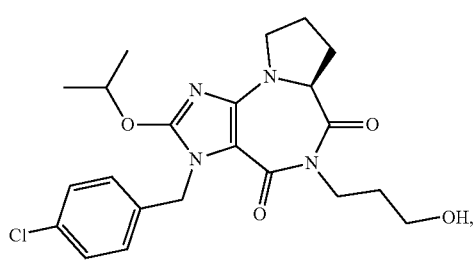

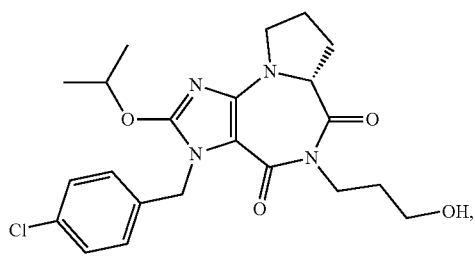

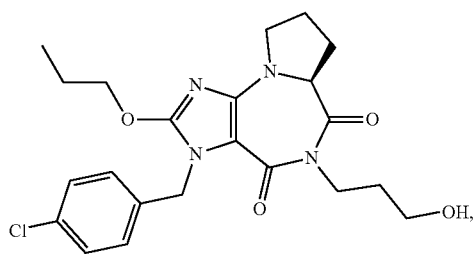

-continued

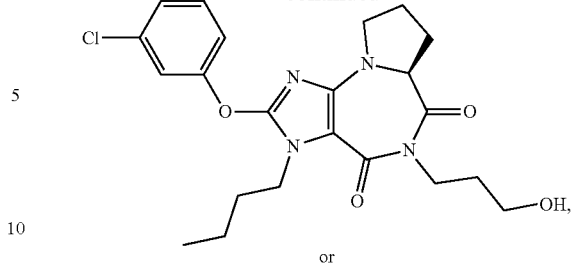

or

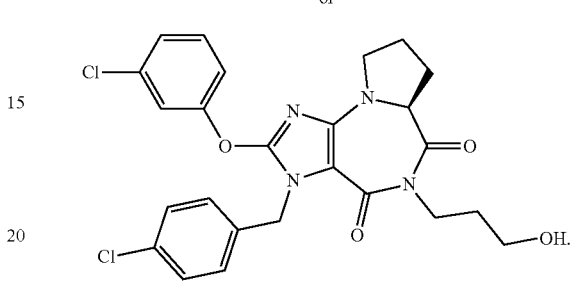

In certain embodiments, the compounds of the invention may be racemic. In certain embodiments, the compounds of the invention may be enriched in one enantiomer. For example, a compound of the invention may have greater than 30% ee, 40% ee, 50% ee, 60% ee, 70% ee, 80% ee, 90% ee, or even 95% or greater ee.

The compounds of the invention have more than one stereocenter. Accordingly, the compounds of the invention may be enriched in one or more diastereomers. For example, a compound of the invention may have greater than 30% de, 40% de, 50% de, 60% de, 70% de, 80% de, 90% de, or even 95% or greater de. In certain embodiments, the compounds of the invention have substantially one isomeric configuration at one or more stereogenic centers, and have multiple isomeric configurations at the remaining stereogenic centers.

In certain embodiments, the enantiomeric excess of the stereocenter is at least 40% ee, 50% ee, 60% ee, 70% ee, 80% ee, 90% ee, 92% ee, 94% ee, 95% ee, 96% ee, 98% ee or greater ee.

As used herein, single bonds drawn without stereochemistry do not indicate the stereochemistry of the compound.

As used herein, hashed or bolded non-wedge bonds indicate relative, but not absolute, stereochemical configuration (e.g., do not distinguish between enantiomers of a given diastereomer).

As used herein, hashed or bolded wedge bonds indicate absolute stereochemical configuration.

In certain embodiments, a therapeutic preparation of the compound of the invention may be enriched to provide predominantly one enantiomer of a compound. An enantiomerically enriched mixture may comprise, for example, at least 60 mol percent of one enantiomer, or more preferably at least 75, 90, 95, or even 99 mol percent. In certain embodiments, the compound enriched in one enantiomer is substantially free of the other enantiomer, wherein substantially free means that the substance in question makes up less than 10%, or less than 5%, or less than 4%, or less than 3%, or less than 2%, or less than 1% as compared to the amount of the other enantiomer, e.g., in the composition or compound mixture. For example, if a composition or compound mixture contains 98 grams of a first enantiomer and 2 grams of a second enantiomer, it would be said to contain 98 mol percent of the first enantiomer and only 2% of the second enantiomer.

In certain embodiments, a therapeutic preparation may be enriched to provide predominantly one diastereomer of the compound of the invention. A diastereomerically enriched mixture may comprise, for example, at least 60 mol percent of one diastereomer, or more preferably at least 75, 90, 95, or even 99 mol percent.

Methods of Treatment

The non-selective $Ca^{2+}$-permeable Transient Receptor Potential (TRP) channels act as sensors that transduce extracellular cues to the intracellular environment in diverse cellular processes, including actin remodeling and cell migration (Greka et al., Nat Neurosci 6, 837-845, 2003; Ramsey et al., Annu Rev Physiol 68, 619-647, 2006; Montell, Pflugers Arch 451, 19-28, 2005; Clapham, Nature 426, 517-524, 2003). Dynamic rearrangement of the actin cytoskeleton relies on spatiotemporally regulated $Ca^{2+}$ influx (Zheng and Poo, Annu Rev Cell Dev Biol 23, 375-404, 2007); Brandman and Meyer, Science 322, 390-395, 2008); Collins and Meyer, Dev Cell 16, 160-161, 2009) and the small GTPases RhoA and Rac1 serve as key modulators of these changes (Etienne-Manneville and Hall, Nature 420, 629-635, 2002); Raftopoulou and Hall, Dev Biol 265, 23-32, 2004). RhoA induces stress fiber and focal adhesion formation, while Rac1 mediates lamellipodia formation (Etienne-Manneville and Hall, Nature 420, 629-635, 2002). The Transient Receptor Potential Cation Channel, subfamily C, member 5 (TRPC5) acts in concert with TRPC6 to regulate $Ca^{2+}$ influx, actin remodeling, and cell motility in kidney podocytes and fibroblasts. TRPC5-mediated $Ca^{2+}$ influx increases Rac1 activity, whereas TRPC6-mediated $Ca^{2+}$ influx promotes RhoA activity. Gene silencing of TRPC6 channels abolishes stress fibers and diminishes focal contacts, rendering a motile, migratory cell phenotype. In contrast, gene silencing of TRPC5 channels rescues stress fiber formation, rendering a contractile cell phenotype. The results described herein unveil a conserved signaling mechanism whereby TRPC5 and TRPC6 channels control a tightly regulated balance of cytoskeletal dynamics through differential coupling to Rac1 and RhoA.

$Ca^{2+}$-dependent remodeling of the actin cytoskeleton is a dynamic process that drives cell migration (Wei et al., Nature 457, 901-905, 2009). RhoA and Rac1 act as switches responsible for cytoskeletal rearrangements in migrating cells (Etienne-Manneville and Hall, Nature 420, 629-635, 2002); Raftopoulou and Hall, Dev Biol 265, 23-32, 2004). Activation of Rac1 mediates a motile cell phenotype, whereas RhoA activity promotes a contractile phenotype (Etienne-Manneville and Hall, Nature 420, 629-635, 2002). $Ca^{2+}$ plays a central role in small GTPase regulation (Aspenstrom et al., Biochem J 377, 327-337, 2004). Spatially and temporally restricted flickers of $Ca^{2+}$ are enriched near the leading edge of migrating cells (Wei et al., Nature 457, 901-905, 2009). $Ca^{2+}$ microdomains have thus joined local bursts in Rac1 activity (Gardiner et al., Curr Biol 12, 2029-2034, 2002; Machacek et al., Nature 461, 99-103, 2009) as critical events at the leading edge. To date, the sources of $Ca^{2+}$ influx responsible for GTPase regulation remain largely elusive. TRP (Transient Receptor Potential) channels generate time and space-limited $Ca^{2+}$ signals linked to cell migration in fibroblasts and neuronal growth cones0. Specifically, TRPC5 channels are known regulators of neuronal growth cone guidance1 and their activity in neurons is dependent on PI3K and Rac1 activity (Bezzerides et al., Nat Cell Biol 6, 709-720, 2004).

Podocytes are neuronal-like cells that originate from the metanephric mesenchyme of the kidney glomerulus and are essential to the formation of the kidney filtration apparatus (Somlo and Mundel, Nat Genet. 24, 333-335, 2000; Fukasawa et al., J Am Soc Nephrol 20, 1491-1503, 2009). Podocytes possess an exquisitely refined repertoire of cytoskeletal adaptations to environmental cues (Somlo and Mundel, Nat Genet 24, 333-335, 2000; Garg et al., Mol Cell Biol 27, 8698-8712, 2007; Verma et al., J Clin Invest 116, 1346-1359, 2006; Verma et al., J Biol Chem 278, 20716-20723, 2003; Barletta et al., J Biol Chem 278, 19266-19271, 2003; Holzman et al., Kidney Int 56, 1481-1491, 1999; Ahola et al., Am J Pathol 155, 907-913, 1999; Tryggvason and Wartiovaara, N Engl J Med 354, 1387-1401, 2006; Schnabel and Farquhar, J Cell Biol 111, 1255-1263, 1990; Kurihara et al., Proc Natl Acad Sci USA 89, 7075-7079, 1992). Early events of podocyte injury are characterized by dysregulation of the actin cytoskeleton (Faul et al., Trends Cell Biol 17, 428-437, 2007; Takeda et al., J Clin Invest 108, 289-301, 2001; Asanuma et al., Nat Cell Biol 8, 485-491, 2006) and $Ca^{2+}$ homeostasis (Hunt et al., J Am Soc Nephrol 16, 1593-1602, 2005; Faul et al., Nat Med 14, 931-938, 2008). These changes are associated with the onset of proteinuria, the loss of albumin into the urinary space, and ultimately kidney failure (Tryggvason and Wartiovaara, N Engl J Med 354, 1387-1401, 2006). The vasoactive hormone Angiotensin II induces $Ca^{2+}$ influx in podocytes, and prolonged treatment results in loss of stress fibers (Hsu et al., J Mol Med 86, 1379-1394, 2008). While there is a recognized link between $Ca^{2+}$ influx and cytoskeletal reorganization, the mechanisms by which the podocyte senses and transduces extracellular cues that modulate cell shape and motility remain elusive. TRP Canonical 6 (TRPC6) channel mutations have been linked to podocyte injury (Winn et al., Science 308, 1801-1804, 2005; Reiser et al., Nat Genet 37, 739-744, 2005; Moller et al., J Am Soc Nephrol 18, 29-36, 2007; Hsu et al., Biochim Biophys Acta 1772, 928-936, 2007), but little is known about the specific pathways that regulate this process. Moreover, TRPC6 shares close homology with six other members of the TRPC channel family (Ramsey et al., Annu Rev Physiol 68, 619-647, 2006; Clapham, Nature 426, 517-524, 2003). TRPC5 channels antagonize TRPC6 channel activity to control a tightly regulated balance of cytoskeletal dynamics through differential coupling to distinct small GTPases.

Proteinuria

Proteinuria is a pathological condition wherein protein is present in the urine. Albuminuria is a type of proteinuria. Microalbuminuria occurs when the kidney leaks small amounts of albumin into the urine. In a properly functioning body, albumin is not normally present in urine because it is retained in the bloodstream by the kidneys. Microalbuminuria is diagnosed either from a 24-hour urine collection (20 to 200 µg/min) or, more commonly, from elevated concentrations (30 to 300 mg/L) on at least two occasions. Microalbuminuria can be a forerunner of diabetic nephropathy. An albumin level above these values is called macroalbuminuria. Subjects with certain conditions, e.g., diabetic nephropathy, can progress from microalbuminuria to macroalbuminuria and reach a nephrotic range (>3.5 g/24 hours) as kidney disease reaches advanced stages.

Causes of Proteinuria

Proteinuria can be associated with a number of conditions, including focal segmental glomerulosclerosis, IgA nephropathy, diabetic nephropathy, lupus nephritis, membranoproliferative glomerulonephritis, progressive (crescentic) glomerulonephritis, and membranous glomerulonephritis.

A. Focal Segmental Glomerulosclerosis (FSGS)

Focal Segmental Glomerulosclerosis (FSGS) is a disease that attacks the kidney's filtering system (glomeruli) causing serious scarring. FSGS is one of the many causes of a disease known as Nephrotic Syndrome, which occurs when protein in the blood leaks into the urine (proteinuria).

Very few treatments are available for patients with FSGS. Many patients are treated with steroid regimens, most of which have very harsh side effects. Some patients have shown to respond positively to immunosuppressive drugs as well as blood pressure drugs which have shown to lower the level of protein in the urine. To date, there is no commonly accepted effective treatment or cure and there are no FDA approved drugs to treat FSGS. Therefore, more effective methods to reduce or inhibit proteinuria are desirable.

B. IgA Nephropathy

IgA nephropathy (also known as IgA nephritis, IgAN, Berger's disease, and synpharyngitic glomerulonephritis) is a form of glomerulonephritis (inflammation of the glomeruli of the kidney). IgA nephropathy is the most common glomerulonephritis throughout the world. Primary IgA nephropathy is characterized by deposition of the IgA antibody in the glomerulus. There are other diseases associated with glomerular IgA deposits, the most common being Henoch-Schönlein purpura (HSP), which is considered by many to be a systemic form of IgA nephropathy. Henoch-Schonlein purpura presents with a characteristic purpuric skin rash, arthritis, and abdominal pain and occurs more commonly in young adults (16-35 yrs old). HSP is associated with a more benign prognosis than IgA nephropathy. In IgA nephropathy there is a slow progression to chronic renal failure in 25-30% of cases during a period of 20 years.

C. Diabetic Nephropathy

Diabetic nephropathy, also known as Kimmelstiel-Wilson syndrome and intercapillary glomerulonephritis, is a progressive kidney disease caused by angiopathy of capillaries in the kidney glomeruli. It is characterized by nephrotic syndrome and diffuse glomerulosclerosis. It is due to long-standing diabetes mellitus and is a prime cause for dialysis. The earliest detectable change in the course of diabetic nephropathy is a thickening in the glomerulus. At this stage, the kidney may start allowing more serum albumin than normal in the urine. As diabetic nephropathy progresses, increasing numbers of glomeruli are destroyed by nodular glomerulosclerosis and the amount of albumin excreted in the urine increases.

D. Lupus Nephritis

Lupus nephritis is a kidney disorder that is a complication of systemic lupus erythematosus. Lupus nephritis occurs when antibodies and complement build up in the kidneys, causing inflammation. It often causes proteinuria and may progress rapidly to renal failure. Nitrogen waste products build up in the bloodstream. Systemic lupus erythematosus causes various disorders of the internal structures of the kidney, including interstitial nephritis. Lupus nephritis affects approximately 3 out of 10,000 people.

E. Membranoproliferative Glomerulonephritis I/II/III

Membranoproliferative glomerulonephritis is a type of glomerulonephritis caused by deposits in the kidney glomerular mesangium and basement membrane thickening, activating complement and damaging the glomeruli. There are three types of membranoproliferative glomerulonephritis. Type I is caused by immune complexes depositing in the kidney and is believed to be associated with the classical complement pathway. Type II is similar to Type I, however, it is believed to be associated with the alternative complement pathway. Type III is very rare and it is characterized by a mixture of subepithelial deposits and the typical pathological findings of Type I disease.

F. Progressive (Crescentic) Glomerulonephritis

Progressive (crescentic) glomerulonephritis (PG) is a syndrome of the kidney that, if left untreated, rapidly progresses into acute renal failure and death within months. In 50% of cases, PG is associated with an underlying disease such as Goodpasture's syndrome, systemic lupus erythematosus, or Wegener granulomatosis; the remaining cases are idiopathic. Regardless of the underlying cause, PG involves severe injury to the kidney's glomeruli, with many of the glomeruli containing characteristic crescent-shaped scars. Patients with PG have hematuria, proteinuria, and occasionally, hypertension and edema. The clinical picture is consistent with nephritic syndrome, although the degree of proteinuria may occasionally exceed 3 g/24 hours, a range associated with nephrotic syndrome. Untreated disease may progress to decreased urinary volume (oliguria), which is associated with poor kidney function.

G. Membranous Glomerulonephritis

Membranous glomerulonephritis (MGN) is a slowly progressive disease of the kidney affecting mostly patients between ages of 30 and 50 years, usually Caucasian. It can develop into nephrotic syndrome. MGN is caused by circulating immune complex. Current research indicates that the majority of the immune complexes are formed via binding of antibodies to antigens in situ to the glomerular basement membrane. The said antigens may be endogenous to the basement membrane, or deposited from systemic circulation.

H. Obesity

Experimentally induced TrpC5 deficiency in mice has been shown to cause a positive energy balance that leads to excess weight gain Y Gao et al., Cell Rep 2017, 18(3), pp. 583-92. Thus, agonism of TrpC5 may lead to a reduction in obesity.

Measurement of Urine Protein Levels

Protein levels in urine can be measured using methods known in the art. Until recently, an accurate protein measurement required a 24-hour urine collection. In a 24-hour collection, the patient urinates into a container, which is kept refrigerated between trips to the bathroom. The patient is instructed to begin collecting urine after the first trip to the bathroom in the morning. Every drop of urine for the rest of the day is to be collected in the container. The next morning, the patient adds the first urination after waking and the collection is complete.

More recently, researchers have found that a single urine sample can provide the needed information. In the newer technique, the amount of albumin in the urine sample is compared with the amount of creatinine, a waste product of normal muscle breakdown. The measurement is called a urine albumin-to-creatinine ratio (UACR). A urine sample containing more than 30 milligrams of albumin for each gram of creatinine (30 mg/g) is a warning that there may be a problem. If the laboratory test exceeds 30 mg/g, another UACR test should be performed 1 to 2 weeks later. If the second test also shows high levels of protein, the person has persistent proteinuria, a sign of declining kidney function, and should have additional tests to evaluate kidney function.

Tests that measure the amount of creatinine in the blood will also show whether a subject's kidneys are removing wastes efficiently. Too much creatinine in the blood is a sign that a person has kidney damage. A physician can use the creatinine measurement to estimate how efficiently the kidneys are filtering the blood. This calculation is called the estimated glomerular filtration rate, or eGFR. Chronic kidney disease is present when the eGFR is less than 60 milliliters per minute (mL/min).

TRPC5

TRPC is a family of transient receptor potential cation channels in animals. TRPC5 is subtype of the TRPC family of mammalian transient receptor potential ion channels. Three examples of TRPC5 are highlighted below in Table 1.

TABLE 1

The TRPC5 orthologs from three different species along with their GenBank Ref Seq Accession Numbers.

| Species | Nucleic Acid | Amino Acid | GeneID |
|---|---|---|---|
| Homo sapiens | NM_012471.2 | NP_036603.1 | 7224 |
| Mus musculus | NM_009428.2 | NP_033454.1 | 22067 |
| Rattus norvegicus | NM_080898.2 | NP_543174.1 | 140933 |

Accordingly, in certain embodiments, the invention provides methods for treating, or the reducing risk of developing, a kidney disease comprising administering to a subject in need thereof a therapeutically effective amount of a TRPC5 inhibitory compound of the invention (e.g., a TRPC5 inhibitory compound of Formula I or II), or a pharmaceutical composition comprising said compound.

In some embodiments, the kidney disease is selected from the group consisting of Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, and IgA nephropathy. In some embodiments, the kidney disease is proteinuria. In some embodiments, the kidney disease is microalbuminuria or macroalbuminuria.

The invention also provides methods of treating, or the reducing risk of developing, anxiety, or depression, or cancer, comprising administering to a subject in need thereof a therapeutically effective amount of a TRPC5 inhibitory compound of the invention (e.g., a TRPC5 inhibitory compound of Formula I or II), or a pharmaceutical composition comprising said compound.

In certain embodiments, the invention provides methods for treating, or the reducing risk of developing, obesity comprising administering to a subject in need thereof a therapeutically effective amount of a TRPC5 agonist compound of the invention (e.g., a TRPC5 agonist compound of Formula I or II), or a pharmaceutical composition comprising said compound.

Subjects to be Treated

In one aspect of the invention, a subject is selected on the basis that they have, or are at risk of developing, a kidney disease, anxiety, depression, or cancer.

Subjects that have, or are at risk of developing, proteinuria include those with diabetes, hypertension, or certain family backgrounds. In the United States, diabetes is the leading cause of end-stage renal disease (ESRD). In both type 1 and type 2 diabetes, albumin in the urine is one of the first signs of deteriorating kidney function. As kidney function declines, the amount of albumin in the urine increases. Another risk factor for developing proteinuria is hypertension. Proteinuria in a person with high blood pressure is an indicator of declining kidney function. If the hypertension is not controlled, the person can progress to full kidney failure. African Americans are more likely than Caucasians to have high blood pressure and to develop kidney problems from it, even when their blood pressure is only mildly elevated. Other groups at risk for proteinuria are American Indians, Hispanics/Latinos, Pacific Islander Americans, older adults, and overweight subjects.

In one aspect of the invention, a subject is selected on the basis that they have, or are at risk of developing proteinuria. A subject that has, or is at risk of developing, proteinuria is one having one or more symptoms of the condition. Symptoms of proteinuria are known to those of skill in the art and include, without limitation, large amounts of protein in the urine, which may cause it to look foamy in the toilet. Loss of large amounts of protein may result in edema, where swelling in the hands, feet, abdomen, or face may occur. These are signs of large protein loss and indicate that kidney disease has progressed. Laboratory testing is the only way to find out whether protein is in a subject's urine before extensive kidney damage occurs.

The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses. In some embodiments, the subject is a mammal. In some embodiments, the subject is a human.

EXAMPLES

The invention is further described in the following examples, which do not limit the scope of the invention described in the claims.

Example 1: Synthetic Methods

The following illustrate synthetic routes to exemplary compounds of the invention.

Preparation of Intermediate A

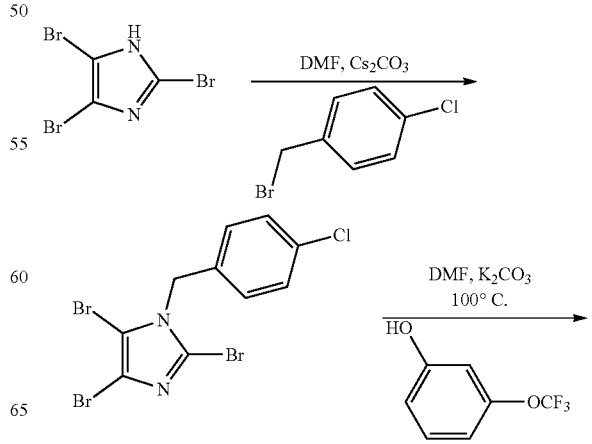

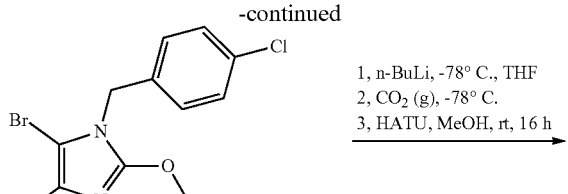

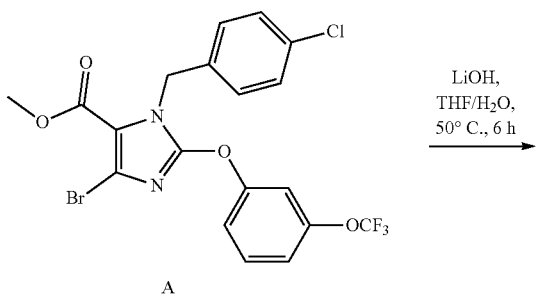

A

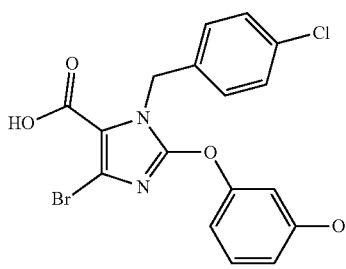

B 2,4,5-tribromo-1-[(4-chlorophenyl)methyl]-1H-imidazole

A mixture of 2,4,5-tribromo-1H-imidazole (120 g, 393.75 mmol, 1 equiv.), 1-(bromomethyl)-4-chlorobenzene (100 g, 486.67 mmol, 1.236 equiv.) and Cs₂CO₃ (200 g, 613.84 mmol, 1.559 equiv.) in DMF (1000 mL) was stirred at room temperature for 16 hours. To the reaction mixture was added EtOAc (500 mL) and H₂O (300 mL). The organic layer was washed with H₂O (2×300 mL) and brine (300 mL), dried over anhydrous Na₂SO₄, filtered. The filtrate was concentrated to afford 2,4,5-tribromo-1-[(4-chlorophenyl)methyl]-1H-imidazole (170 g, crude) as a light yellow solid.

4,5-dibromo-1-[(4-chlorophenyl)methyl]-2-[3-(trifluoromethoxy)phenoxy]-1H-imidazole A mixture of 2,4,5-tribromo-1-[(4-chlorophenyl)methyl]-1H-imidazole (175 g, 407.61 mmol, 1 equiv.), 3-(trifluoromethoxy)phenol (87.5 g, 491.27 mmol, 1.205 equiv.) and DMF (1000 mL) K₂CO₃ (175 g, 1266.23 mmol, 3.106 equiv.) in DMF (1000 mL) was stirred at 100° C. for 16 hours. The reaction mixture was cooled to room temperature and added EtOAc (750 mL) and H₂O (500 mL). The organic layer was washed with H₂O (2×300 mL) and brine (150 mL), then dried over anhydrous Na₂SO₄ and filtered. The filtrate was concentrated to give the crude product which was purified by silica gel column chromatography, eluted with PE:EtOAc (20:1 to 10:1) to give 4,5-dibromo-1-[(4-chlorophenyl)methyl]-2-[3-(trifluoromethoxy)phenoxy]-1H-imidazole (200 g, 93.19%) as a light yellow solid.

methyl 4-bromo-1-[(4-chlorophenyl)methyl]-2-[3-(trifluoromethoxy)phenoxy]-1H-imidazole-5-carboxylate (Intermediate A)

To a stirred solution of 4,5-dibromo-1-[(4-chlorophenyl)methyl]-2-[3-(trifluoromethoxy)phenoxy]-1H-imidazole (10.52 g, 19.98 mmol, 1 equiv.) in THF (100 mL) was added dropwise n-BuLi (25.8 mL, 64.57 mmol, 1 equiv.) at −78° C. The resulting mixture was stirred at −78° C. for 30 min, then CO₂ (g) was bubbled through the above mixture at −78° C. for 50 min. The reaction mixture was stirred at −78° C. for 30 min. To the above solution was added HATU (36.8 g, 96.86 mmol, 1.5 equiv.), MeOH (180 mL) and TEA (70 mL), then the resulting mixture was stirred at room temperature for 12 hours. The reaction mixture was filtered and the filtrate was concentrated to give the crude product which was purified by silica gel column chromatography, eluting with PE:EA (20:1 to 5:1) to afford methyl 4-bromo-1-[(4-chlorophenyl)methyl]-2-[3-(trifluoromethoxy)phenoxy]-1H-imidazole-5-carboxylate (26 g, 79.63%) as a white solid. ¹H NMR (400 MHz, Chloroform-d) δ 7.46-7.40 (m, 1H), 7.36-7.30 (m, 2H), 7.22 (dd, J=8.4, 2.4 Hz, 3H), 7.13 (dtd, J=9.9, 2.1, 1.1 Hz, 2H), 5.52 (s, 2H), 3.89 (s, 3H).

Preparation of intermediates C, E, G, I, J, K, L, M and N shown in the table below follows the methods and protocols as described for the synthesis of intermediate A, starting with the appropriate halide and phenol:

| Intermediate | Halide | Phenol | Structure | Characterization |
|---|---|---|---|---|
| C | 1-bromobutane | 3-(trifluoromethoxy)phenol | 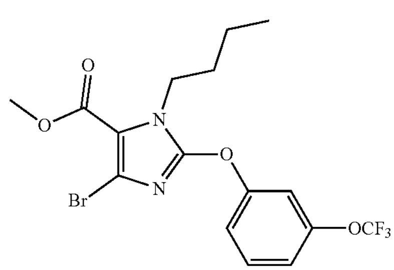 [SMILES: CCCCn1c(Oc2cccc(OC(F)(F)F)c2)nc(Br)c1C(=O)OC] | ¹H NMR (400 MHz, Chloroform-d) δ 7.44 (t, J = 8.3 Hz, 1H), 7.25 (ddd, J = 8.3, 2.4, 0.9 Hz, 1H), 7.19-7.09 (m, 2H), 4.30 (t, J = 7.3 Hz, 2H), 3.92 (s, 3H), 1.81-1.70 (m, 2H), 1.45-1.34 (m, 2H), 0.97 (t, J = 7.4 Hz, 3H) |

-continued

| Intermediate | Halide | Phenol | Structure | Characterization |
|---|---|---|---|---|
| E | 1-(bromomethyl)-4-chlorobenzene | 3-fluorophenol | 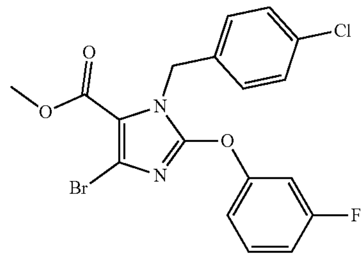 [SMILES: COC(=O)c1c(Br)nc(Oc2cccc(F)c2)n1Cc1ccc(Cl)cc1] | $^1$H NMR (400 MHz, Chloroform-d) δ 7.41-7.30 (m, 3H), 7.25-7.20 (m, 2H), 7.07-6.94 (m, 3H), 5.51 (s, 2H), 3.89 (s, 3H) |
| G | 1-(1-bromoethyl)-4-chlorobenzene | 3-fluorophenol | 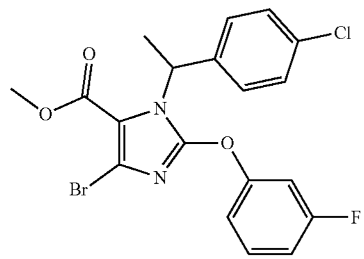 [SMILES: COC(=O)c1c(Br)nc(Oc2cccc(F)c2)n1C(C)c1ccc(Cl)cc1] | $^1$H NMR (400 MHz, Chloroform-d) δ 7.30 (s, 2H), 7.17 (d, J = 8.4 Hz, 1H), 6.91 (tdd, J = 8.8, 5.2, 2.8 Hz, 2H), 6.78-6.69 (m, 2H), 6.62 (q, J = 7.2 Hz, 1H), 5.45 (q, J = 7.2 Hz, 0H), 4.14 (q, J = 7.0 Hz, 0H), 3.94 (s, 3H), 1.95 (d, J = 7.2 Hz, 3H) |
| I | 1-bromobutane | 3-fluorophenol | 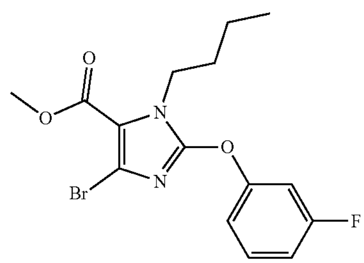 [SMILES: CCCCn1c(Oc2cccc(F)c2)nc(Br)c1C(=O)OC] | $^1$H NMR (400 MHz, Chloroform-d) δ 7.42-7.27 (m, 1H), 7.11-7.01 (m, 2H), 6.96 (ddd, J = 9.9, 8.1, 2.2 Hz, 1H), 4.30 (t, J = 7.3 Hz, 2H), 3.92 (s, 3H), 1.75 (p, J = 7.4 Hz, 2H), 1.39 (h, J = 7.3 Hz, 2H), 0.97 (t, J = 7.3 Hz, 3H). |
| J | 1-(bromomethyl)-4-chlorobenzene | 3-fluorophenol | 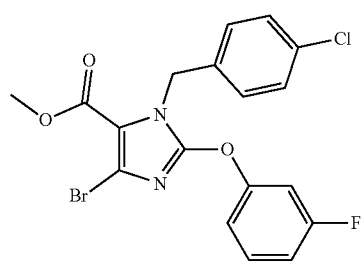 [SMILES: COC(=O)c1c(Br)nc(Oc2cccc(F)c2)n1Cc1ccc(Cl)cc1] | $^1$H NMR (400 MHz, Chloroform-d) δ 7.39-7.31 (m, 3H), 7.23 (d, J = 8.4 Hz, 2H), 7.04 (dt, J = 9.6, 3.8 Hz, 2H), 6.97 (td, J = 8.3, 2.3 Hz, 1H), 5.51 (s, 2H), 3.89 (s, 3H) |
| K | 1-(bromomethyl)-4-chlorobenzene | isopropanol | 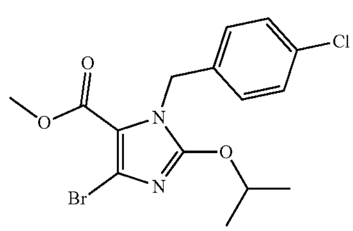 [SMILES: COC(=O)c1c(Br)nc(OC(C)C)n1Cc1ccc(Cl)cc1] | |
| L | 1-(bromomethyl)-4-chlorobenzene | N-propanol | 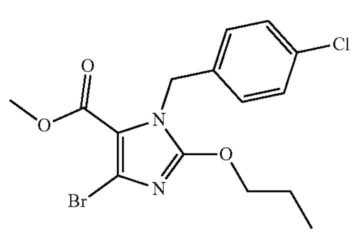 [SMILES: CCCOc1nc(Br)c(C(=O)OC)n1Cc1ccc(Cl)cc1] | |

| Intermediate | Halide | Phenol | Structure | Characterization |
|---|---|---|---|---|
| M | 1-bromobutane | 3-chlorophenol | 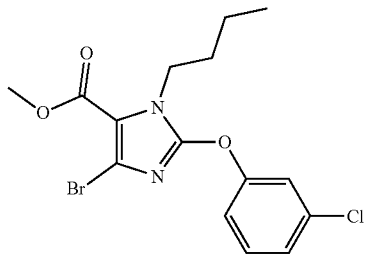 [SMILES: CCCCn1c(Oc2cccc(Cl)c2)nc(Br)c1C(=O)OC] | $^1$H NMR (400 MHz, Chloroform-d) δ 7.34 (t, J = 8.1 Hz, 1H), 7.29 (d, J = 2.5 Hz, 1H), 7.24-7.16 (m, 2H), 4.29 (t, J = 7.3 Hz, 2H), 3.92 (s, 3H), 1.75 (p, J = 7.6 Hz, 2H), 1.39 (h, J = 7.4 Hz, 2H), 0.97 (t, J = 7.3 Hz, 3H) |
| N | 1-(bromomethyl)-4-chlorobenzene | 3-chlorophenol | 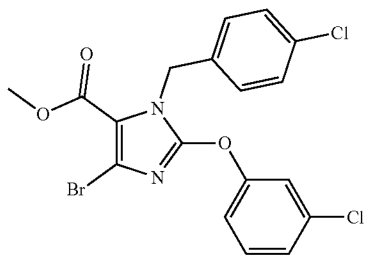 [SMILES: COC(=O)c1c(Br)nc(Oc2cccc(Cl)c2)n1Cc1ccc(Cl)cc1] | |

4-bromo-1-[(4-chlorophenyl)methyl]-2-[3-(trifluoromethoxy)phenoxy]-1H-imidazole-5-carboxylic acid (Intermediate B)

A mixture of methyl 4-bromo-1-[(4-chlorophenyl)methyl]-2-[3-(trifluoromethoxy)phenoxy]-1H-imidazole-5-carboxylate (8 g, 15.82 mmol, 1 equiv.) in THF (50 mL) and H$_2$O (50 mL) was added LiOH (3.8 g, 158.21 mmol, 10 equiv.) and stirred for 10 hours at room temperature. The resulting mixture was extracted with EA (4×200 mL). The combined organic layers were washed with water (1×100 mL), dried over anhydrous Na$_2$SO$_4$. After filtration, the filtrate was concentrated under reduced pressure. The residue/crude product was purified by reverse phase flash with the following conditions (Column: Spherical C18 Column, 20-40 um, 120 g. Mobile Phase A: Water (0.1% AcOH), Mobile Phase B: ACN, Flow rate: 60 mL/min, Gradient:80-90% B in 15 min, 254 nm) to afford 4-bromo-1-[(4-chlorophenyl)methyl]-2-[3-(trifluoromethoxy)phenoxy]-1H-imidazole-5-carboxylic acid (7.5 g, 96.42%) as a white solid. $^1$H NMR (400 MHz, DMSO-d6) δ 13.41 (s, 1H), 7.59 (t, J=8.3 Hz, 1H), 7.42 (dd, J=8.7, 2.1 Hz, 3H), 7.37 (dt, J=8.2, 1.5 Hz, 1H), 7.33-7.29 (m, 1H), 7.29-7.24 (m, 2H), 5.51 (s, 2H)

Preparation of intermediates D, F and H shown in the table below follows the methods and protocols as described for the synthesis of intermediate B, starting with the appropriate intermediate:

| Intermediate | Starting Material | Structure | Characterization |
|---|---|---|---|
| D | C | 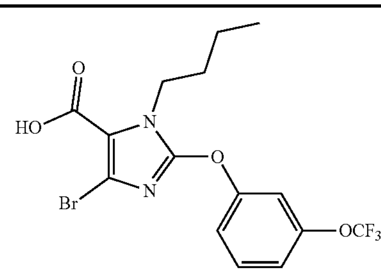 | $^1$H NMR (400 MHz, Chloroform-d) δ 7.46 (t, J = 8.3 Hz, 1H), 7.29-7.25 (m, 1H), 7.21-7.12 (m, 2H), 4.34 (t, J = 7.2 Hz, 2H), 1.85-1.73 (m, 2H), 1.41 (h, J = 7.4 Hz, 2H), 0.99 (t, J = 7.4 Hz, 3H) |
| F | E | 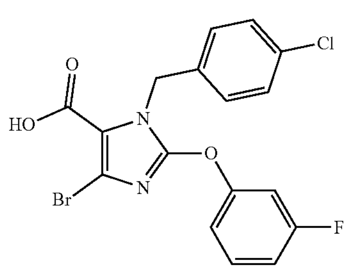 [SMILES: O=C(O)c1c(Br)nc(Oc2cccc(F)c2)n1Cc1ccc(Cl)cc1] | |

-continued
| Intermediate | Starting Material | Structure | Characterization |
|---|---|---|---|
| H | G | 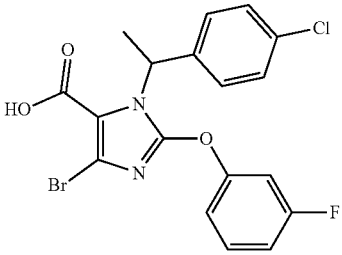 [SMILES: CC(c1ccc(Cl)cc1)n1c(Oc2cccc(F)c2)nc(Br)c1C(=O)O] | |
Preparation of Compound 1
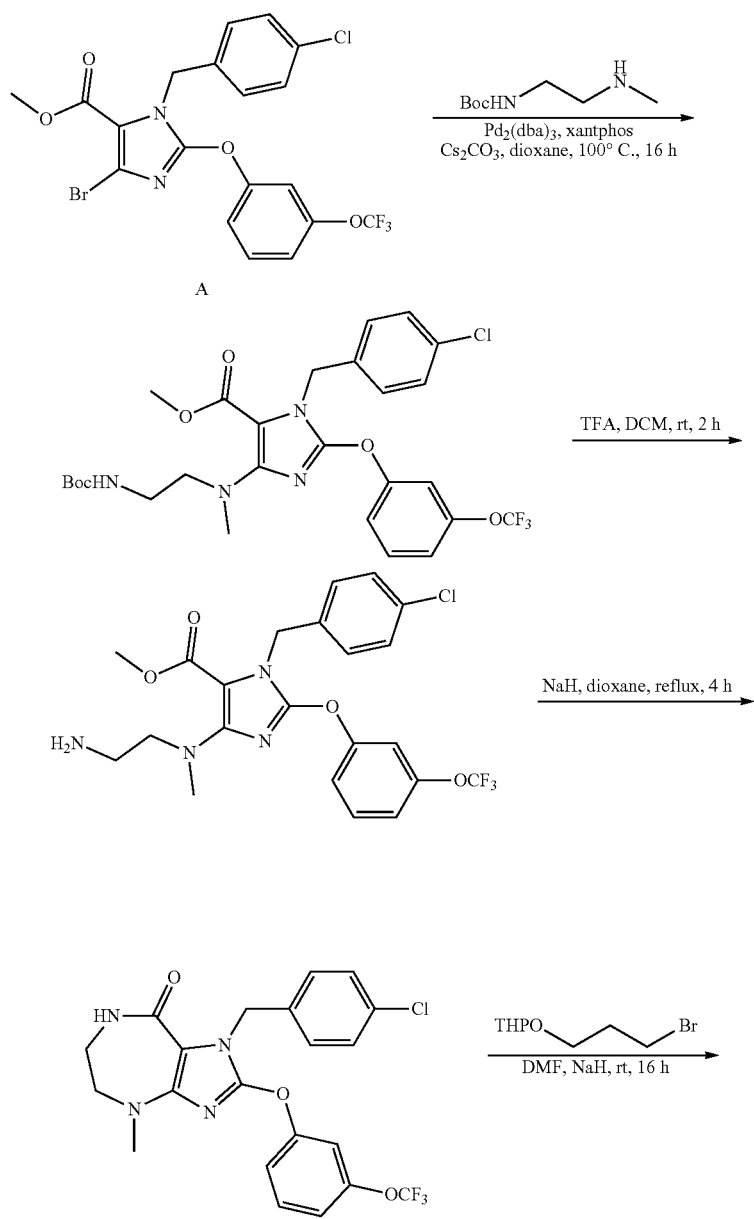

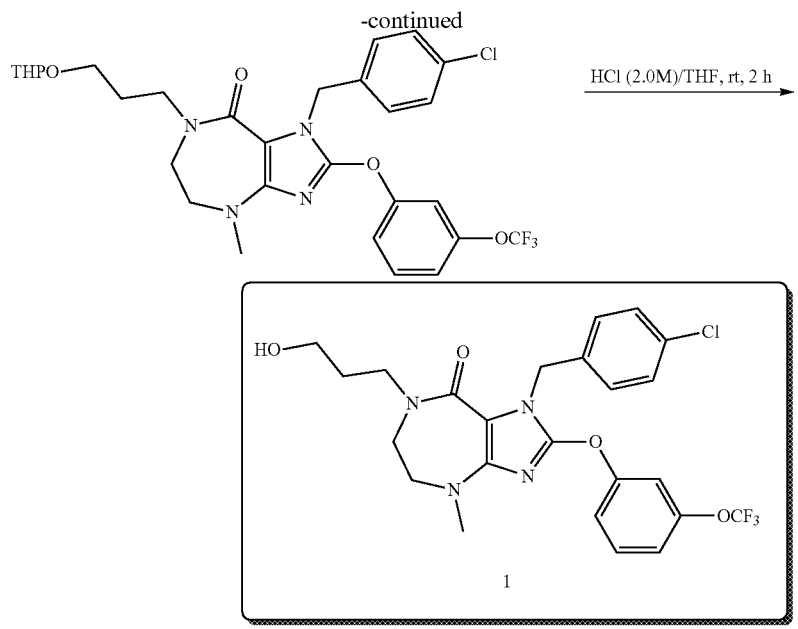

methyl 4-[(2-[[(tert-butoxy)carbonyl]amino]ethyl)(methyl)amino]-1-[(4-chlorophenyl)methyl]-2-[3-(trifluoromethoxy)phenoxy]-1H-imidazole-5-carboxylate A mixture of methyl 4-bromo-1-[(4-chlorophenyl)methyl]-2-[3-(trifluoromethoxy)phenoxy]-1H-imidazole-5-carboxylate (2 g, 3.96 mmol, 1 equiv.), tert-butyl N-[2-(methylamino)ethyl]carbamate (1.4 g, 7.91 mmol, 2.00 equiv.), XantPhos (686.6 mg, 1.19 mmol, 0.3 equiv.), $Pd_2(dba)_3$ (362.2 mg, 0.40 mmol, 0.1 equiv.) and $Cs_2CO_3$ (3.9 g, 11.87 mmol, 3 equiv.) in dioxane (30 mL, 89.53 equiv.) was stirred at 100° C. for 14 hr. The reaction mixture was filtered and the filtrate was concentrated to give the crude product which was purified by silica gel column chromatography, eluted with PE:EA (10:1 to 3:2) to afford methyl 4-[(2-[[(tert-butoxy)carbonyl]amino]ethyl)(methyl)amino]-1-[(4-chlorophenyl)methyl]-2-[3-(trifluoromethoxy)phenoxy]-1H-imidazole-5-carboxylate (630 mg, 26.59%) as a light yellow oil. $^1$H NMR (400 MHz, Chloroform-d) δ 7.41 (t, J=8.2 Hz, 1H), 7.34-7.26 (m, 3H), 7.18 (t, J=8.7 Hz, 2H), 7.09 (d, J=8.4 Hz, 1H), 5.39 (s, 2H), 5.28 (s, 1H), 3.78 (s, 3H), 3.38 (dd, J=18.5, 5.7 Hz, 4H), 2.94 (s, 3H), 1.43 (s, 9H)

methyl 4-[(2-aminoethyl)(methyl)amino]-1-[(4-chlorophenyl)methyl]-2-[3-(trifluoromethoxy)phenoxy]-1H-imidazole-5-carboxylate To a stirred solution of methyl 4-[(2-[[(tert-butoxy)carbonyl]amino]ethyl)(methyl)amino]-1-[(4-chlorophenyl)methyl]-2-[3-(trifluoromethoxy)phenoxy]-1H-imidazole-5-carboxylate (700 mg, 1.17 mmol, 1 equiv.) in DCM (30 mL) was added dropwise TFA (10 mL) at room temperature. Then the resulting mixture was stirred at room temperature for 2 hours. The reaction mixture was basified to pH 10 with $K_2CO_3$ and extracted with ethyl acetate (5×50 mL), then the organic layer was washed with brine (2×50 mL), dried over anhydrous $Na_2SO_4$ and filtered. The filtrate was concentrated to afford methyl 4-[(2-aminoethyl)(methyl)amino]-1-[(4-chlorophenyl)methyl]-2-[3-(trifluoromethoxy)phenoxy]-1H-imidazole-5-carboxylate (500 mg, crude) as a light yellow oil.

1-[(4-chlorophenyl)methyl]-4-methyl-2-[3-(trifluoromethoxy)phenoxy]-1H,4H,5H,6H,7H,8H-imidazo[4,5-e][1,4]diazepin-8-one To a stirred mixture of methyl 4-[(2-aminoethyl)(methyl)amino]-1-[(4-chlorophenyl)methyl]-2-[3-(trifluoromethoxy)phenoxy]-1H-imidazole-5-carboxylate (370 mg, 0.74 mmol, 1 equiv.) in dioxane (15 mL) was added NaH (59.3 mg, 1.48 mmol, 2.00 equiv, 60%) at 0° C. under nitrogen atmosphere for 0.5 hours. The resulting mixture was stirred for additional 4 hours at 100° C. The resulting mixture was added ethyl acetate (100 mL) and brine (50 mL), then the water layer was extracted with ethyl acetate (100 mL). The combined organic layer was dried over anhydrous $Na_2SO_4$ and filtered. The filtrate was concentrated to give the crude product which was purified by reverse phase flash with the following conditions (Column: Spherical $C_{18}$ Column, 20-40 um, 120 g; Mobile Phase A: Water (0.1% HOAc), Mobile Phase B: ACN; Flow rate: 60 mL/min; Gradient: 40% B to 70% B in 30 min, 254 nm) to afford 1-[(4-chlorophenyl)methyl]-4-methyl-2-[3-(trifluoromethoxy)phenoxy]-1H,4H,5H,6H,7H,8H-imidazo[4,5-e][1,4]diazepin-8-one (23 mg, 6.64%) as a light yellow oil. $^1$H NMR (400 MHz, Chloroform-d) δ 7.37 (q, J=10.5, 9.4 Hz, 1H), 7.27 (d, J=11.1 Hz, 5H), 7.19 (d, J=8.5 Hz, 1H), 7.07 (d, J=8.3 Hz, 1H), 5.80 (s, 1H), 5.53 (s, 2H), 3.54-3.33 (m, 4H), 3.03 (s, 3H)

1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepin-8-one A mixture of 1-[(4-chlorophenyl)methyl]-4-methyl-2-[3-(trifluoromethoxy)phenoxy]-1H,4H,5H,6H,7H,8H-imidazo[4,5-e][1,4]diazepin-8-one (23 mg, 0.05 mmol, 1 equiv.), 2-(3-bromopropoxy)oxane (22.0 mg, 0.10 mmol, 2 equiv.) and $K_2CO_3$ (20.4 mg, 0.15 mmol, 3 equiv.) in DMF (5 mL)

was stirred at room temperature for 8 hours. The reaction was added EtOAc (50 mL) and H2O (50 mL). The organic layer was washed with brine (2×30 mL) and concentrated to give a residue which was purified by reverse phase flash with the following conditions (Column: Spherical C18 Column, 20-40 um, 40 g; Mobile Phase A: Water (0.1% HOAc), Mobile Phase B: ACN; Flow rate: 40 mL/min; Gradient: 50% B to 70% B in 30 min, 254 nm) to afford 1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepin-8-one (10 mg, 33.33%) as a light yellow oil.

1-[(4-chlorophenyl)methyl]-7-(3-hydroxypropyl)-4-methyl-2-[3-(trifluoromethoxy)phenoxy]-1H,4H,5H,6H,7H,8H-imidazo[4,5-e][1,4]diazepin-8-one (Compound 1)

To a stirred solution of 1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepin-8-one (10 mg) in THF (5 mL) was added dropwise 2M HCl (5 mL) at room temperature. Then the resulting mixture was stirred at room temperature for 1 hours. The reaction mixture was basified to pH 10 with $K_2CO_3$ and extracted with ethyl acetate (3×50 mL), then the organic layer was washed with brine (2×20 mL), dried over anhydrous $Na_2SO_4$ and filtered. The filtrate was concentrated to give the crude product which was purified by prep chiral HPLC (Column: XBridge Prep C18 OBD Column, 5 um, 19*150 mm; Mobile Phase A: Water(0.1% FA), Mobile Phase B: ACN; Flow rate: 20 mL/min; Gradient: 50% B to 85% B in 7 min; 254&220 nm; RT: 6.5 min) to afford 1-[(4-chlorophenyl)methyl]-7-(3-hydroxypropyl)-4-methyl-2-[3-(trifluoromethoxy)phenoxy]-1H,4H,5H,6H,7H,8H-imidazo[4,5-e][1,4]diazepin-8-one (2.2 mg, 25.53%) as a light yellow oil. $^1$H NMR (400 MHz, Methanol-d4) δ 7.50 (t, J=8.2 Hz, 1H), 7.33-7.26 (m, 2H), 7.23-7.15 (m, 5H), 5.47 (s, 2H), 3.59-3.54 (m, 2H), 3.53-3.41 (m, 6H), 3.01 (s, 3H), 1.79-1.70 (m, 2H). $[M+H]^+$ calculated for molecular formula $C_{24}H_{24}ClF_3N_4O_4$: 525, observed: 525.

Preparation of Compound 2

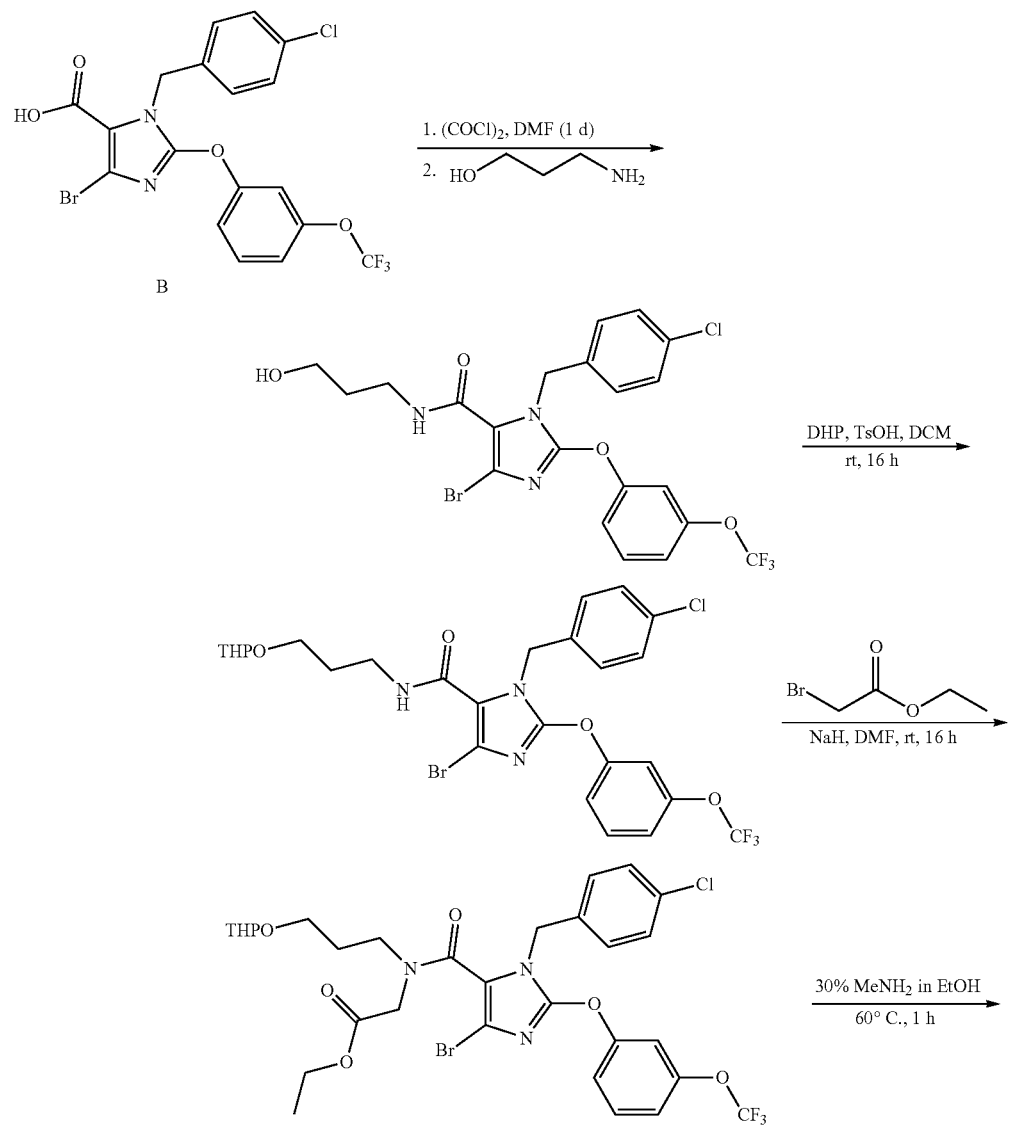

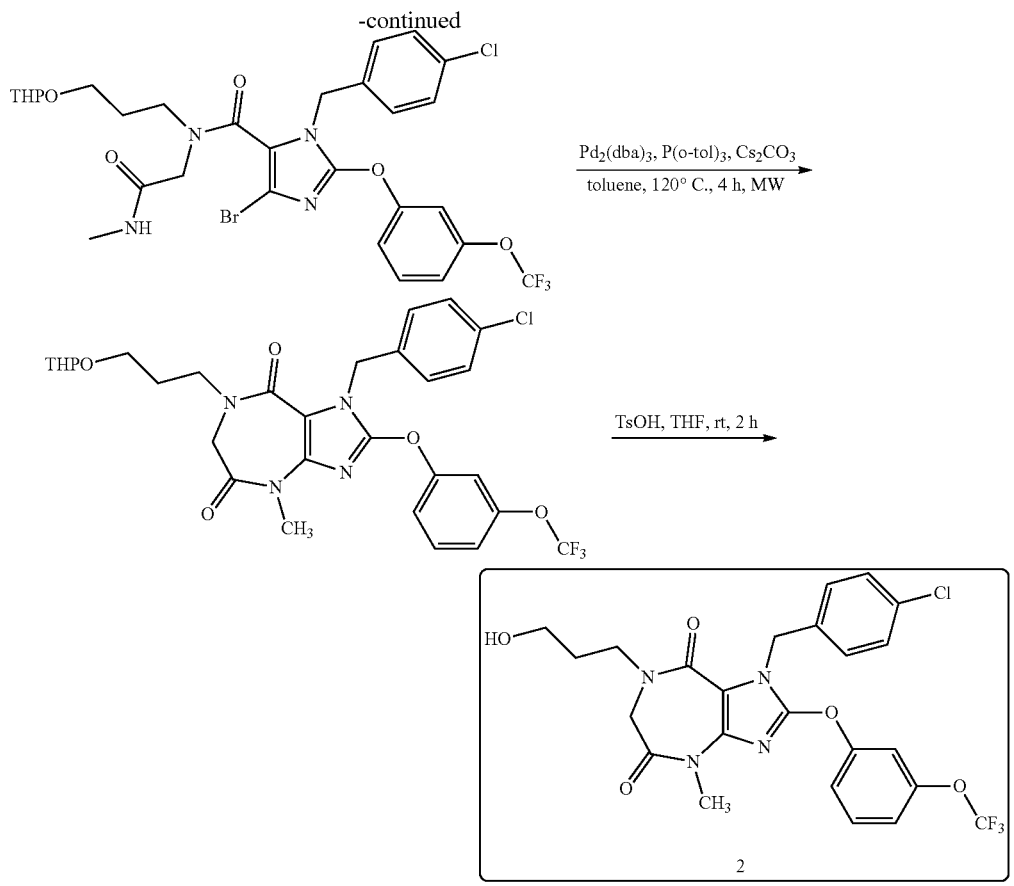

4-bromo-1-[(4-chlorophenyl)methyl]-N-(3-hydroxypropyl)-2-[3-(trifluoromethoxy)phenoxy]-1H-imidazole-5-carboxamide A mixture of 3-aminopropan-1-ol (77.3 mg, 1.03 mmol, 1.5 equiv.), 4-bromo-1-[(4-chlorophenyl)methyl]-2-[3-(trifluoromethoxy)phenoxy]-1H-imidazole-5-carbonyl chloride (350 mg, 0.69 mmol, 1 equiv.) in DCM (20 mL) and TEA (0.5 mL, 4.71 mmol, 5.0 equiv.) was stirred at room temperature for 16 hours. The reaction mixture was concentrated under reduced pressure. The residue was purified by silica gel column chromatography, eluted with PE:EtOAc (1:1 to 1:2) to afford 4-bromo-1-[(4-chlorophenyl)methyl]-N-(3-hydroxypropyl)-2-[3-(trifluoromethoxy)phenoxy]-1H-imidazole-5-carboxamide (220 mg, 58.43%) as a light yellow solid. $^1$H NMR (300 MHz, Chloroform-d) δ 7.43 (td, J=8.0, 7.5, 1.0 Hz, 1H), 7.34-7.28 (m, 4H), 7.26 (d, J=2.4 Hz, 2H), 7.24 (s, 1H), 7.22-7.18 (m, 1H), 7.16-7.08 (m, 2H), 5.58 (s, 2H), 3.61 (dt, J=9.8, 6.0 Hz, 4H), 1.78 (p, J=5.8 Hz, 2H).

4-bromo-1-[(4-chlorophenyl)methyl]-N-[3-(oxan-2-yloxy)propyl]-2-[3-(trifluoromethoxy)phenoxy]-1H-imidazole-5-carboxamide To a mixture of 4-bromo-1-[(4-chlorophenyl)methyl]-N-(3-hydroxypropyl)-2-[3-(trifluoromethoxy)phenoxy]-1H-imidazole-5-carboxamide (1.00 g, 1.82 mol, 1 equiv.) in DCM (30 mL) was added 3,4-dihydro-2H-pyran (306.6 mg, 3.64 mol, 2.0 equiv.) and p-toluenesulfonic acid (15.7 mg, 0.09 mmol, 0.05 equiv.). The resulting mixture was stirred at room temperature for 16 hours. The reaction mixture was concentrated to give the crude which was purified by silica gel column chromatography, eluted with PE:EtOAc (5:1 to 3:1) to afford 4-bromo-1-[(4-chlorophenyl)methyl]-N-[3-(oxan-2-yloxy)propyl]-2-[3-(trifluoromethoxy)phenoxy]-1H-imidazole-5-carboxamide (1.00 g, 86.71%) as a light yellow oil. $^1$H NMR (300 MHz, Chloroform-d) δ 7.52-7.05 (m, 8H), 6.92 (s, 1H), 5.56 (s, 2H), 4.58 (dd, J=4.7, 2.6 Hz, 1H), 4.12-3.30 (m, 9H), 2.01-1.33 (m, 5H).

ethyl 2-(1-[4-bromo-1-[(4-chlorophenyl)methyl]-2-[3-(trifluoromethoxy)phenoxy]-1H-imidazol-5-yl]-N-[3-(oxan-2-yloxy)propyl]formamido)acetate To a mixture of 4-bromo-1-[(4-chlorophenyl)methyl]-N-[3-(oxan-2-yloxy)propyl]-2-[3-(trifluoromethoxy)phenoxy]-1H-imidazole-5-carboxamide (1000 mg, 1.58 mmol, 1 equiv.) in DMF (20 mL) and NaH (126.4 mg, 3.16 mmol, 2.0 equiv, 60%) was added dropwise ethyl 2-bromoacetate (527.8 mg, 3.16 mmol, 2.0 equiv.) at 0° C. The resulting mixture was warmed to room temperature and stirred at room temperature for 16 hours. To the reaction mixture was added H$_2$O (100 mL), the resulting mixture was extracted with ethyl acetate (3×100 mL), the organic layer was washed with brine (100 mL), dried over anhydrous and filtered. The filtrated was concentrated to give a residue which was purified by silica gel column chromatography, eluted with PE:EtOAc (5:1 to 3:1) to afford ethyl 2-(1-[4-bromo-1-[(4-chlorophenyl)methyl]-2-[3-(trifluoromethoxy)phenoxy]-1H-imidazol-5-yl]-N-[3-(oxan-2-yloxy)propyl]formamido) acetate (970 mg, 87.08%) as a light yellow oil. $^1$H NMR (300 MHz, Chloroform-d) δ 7.45-7.35 (m, 4H), 7.34-7.30 (m, 8H), 7.09 (d, J=15.8 Hz, 8H), 6.93 (s, 1H), 5.57 (d, J=5.3 Hz, 2H), 5.17 (s, 6H), 4.53 (d, J=27.3 Hz, 1H), 4.25 (q, J=7.7, 6.9 Hz, 2H), 3.96-3.18 (m, 9H), 1.96-1.70 (m, 3H), 1.31 (d, J=3.1 Hz, 4H).

2-(1-[4-bromo-1-[(4-chlorophenyl)methyl]-2-[3-(trifluoromethoxy)phenoxy]-1H-imidazol-5-yl]-N-[3-(oxan-2-yloxy)propyl]formamido)-N-methylacetamide A mixture of ethyl 2-(1-[4-bromo-1-[(4-chlorophenyl)methyl]-2-[3-(trifluoromethoxy)phenoxy]-1H-imidazol-5-yl]-N-[3-(oxan-2-yloxy)propyl]formamido)acetate (970 mg, 1.35 mmol, 1 equiv.) in 2M methylamine in methanol (3.00 mL) was irradiated with microwave radiation for 1 hour at 60° C. The reaction mixture was cooled to the room temperature and concentrated under reduced pressure. The residue was purified by silica gel column chromatography, eluted with PE:EtOAc (1:6 to 1:9) to afford 2-(1-[4-bromo-1-[(4-chlorophenyl)methyl]-2-[3-(trifluoromethoxy)phenoxy]-1H-imidazol-5-yl]-N-[3-(oxan-2-yloxy)propyl]formamido)-N-methylacetamide (600 mg, 63.17%) as a colorless oil. $^1$H NMR (300 MHz, DMSO-d6) δ 8.07-7.88 (m, 11H), 7.61-7.47 (m, 1H), 7.38 (d, J=1.6 Hz, 6H), 7.24 (dd, J=27.9, 9.7 Hz, 5H), 5.12 (s, 2H), 4.49 (d, J=30.7 Hz, 2H), 4.15 (s, 1H), 3.79-3.55 (m, 1H), 3.39 (s, 6H), 3.27 (d, J=4.1 Hz, OH), 2.60 (dd, J=13.1, 4.4 Hz, 5H), 1.87-1.26 (m, 14H).

1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepine-5,8-dione A mixture of 2-(1-[4-bromo-1-[(4-chlorophenyl)methyl]-2-[3-(trifluoromethoxy)phenoxy]-1H-imidazol-5-yl]-N-[3-(oxan-2-yloxy)propyl]formamido)-N-methylacetamide (500 mg, 0.71 mmol, 1 equiv.), Pd$_2$(dba)$_3$·CHCl$_3$ (73.5 mg, 0.07 mmol, 0.1 equiv.), P(o-Tol)$_3$ (43.2 mg, 0.14 mmol, 0.2 equiv.) and Cs$_2$CO$_3$ (462.9 mg, 1.42 mmol, 2.0 equiv.) in Toluene (10.0 mL) was irradiated with microwave radiation for 4 hours at 120° C. The reaction mixture was cooled to the room temperature and concentrated under reduced pressure. The residue was purified by silica gel column chromatography, eluted with PE:EtOAc (3:1 to 1:1) to afford 1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepine-5,8-dione (300 mg, 67.79%) as a light yellow oil.

1-[(4-chlorophenyl)methyl]-7-(3-hydroxypropyl)-4-methyl-2-[3-(trifluoromethoxy)phenoxy]-1H,4H,5H,6H,7H,8H-imidazo[4,5-e][1,4]diazepine-5,8-dione (Compound 2)

A mixture of 1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepine-5,8-dione (300 mg, 0.48 mmol, 1 equiv) in THF (10 mL) and HCl (6M) (20 mL) was stirred at room temperature for 2 hours. The reaction mixture was concentrated to give the residue. The residue was basified to pH 9 with sat K$_2$CO$_3$ (aq), then the mixture was extracted with ethyl acetate (3×100 mL). The organic layer was washed with brine (50 mL) and concentrated to give the crude product which was purified by reverse phase flash with the following conditions (Column: Spherical C18 Column, 20-40 um, 120 g; Mobile Phase A: Water (0.1% HOAc), Mobile Phase B: ACN; Flow rate: 60 mL/min; Gradient: 50% B to 60% B in 15 min, 254 nm) to afford 1-[(4-chlorophenyl)methyl]-7-(3-hydroxypropyl)-4-methyl-2-[3-(trifluoromethoxy)phenoxy]-1H,4H,5H,6H,7H,8H-imidazo[4,5-e][1,4]diazepine-5,8-dione (220 mg, 84.78%) as a light yellow oil. $^1$H NMR (300 MHz, DMSO-d6) δ 7.59-7.54 (m, 1H), 7.42-7.26 (m, 7H), 5.44 (s, 2H), 4.48 (t, J=5.1 Hz, 1H), 4.05 (s, 2H), 3.51 (t, J=7.1 Hz, 2H), 3.39-3.33 (m, 2H), 3.20 (s, 3H), 1.69-1.60 (m, 2H). [M+H]$^+$ calculated for molecular formula C$_{24}$H$_{22}$ClF$_3$N$_4$O$_5$: 539, observed: 539.

Preparation of compounds 3-5 shown in the table below follows the methods and protocols as described for the synthesis of compound 2, starting with the appropriate intermediate E:

| Compound | Starting Material | NMR | LCMS |
| --- | --- | --- | --- |
| 3 | D | $^1$H NMR (400 MHz, Methanol-d4) δ 7.56 (t, J = 8.3 Hz, 1H), 7.42-7.32 (m, 2H), 7.24-7.20 (m, 1H), 4.30 (t, J = 7.3 HZ, 2H), 4.13 (s, 2H), 3.68 (t, J = 7.0 Hz, 2H), 3.59 (t, J = 6.2 Hz, 2H), 3.33 (s, 3H), 1.90-1.83 (m, 2H), 1.81-1.74 (m, 2H), 1.42-1.33 (m, 2H), 0.97 (t, J = 7.4 Hz, 3H) | [M + H]$^+$ calculated for molecular formula C$_{21}$H$_{25}$F$_3$N$_4$O$_5$: 471, observed: 471 |
| 4 | F | $^1$H NMR (400 MHz, Methanol-d4) δ 7.45-7.39 (m, 1H), 7.37-7.26 (m, 4H), 7.18-7.06 (m, 2H), 7.04-6.99 (, 1H), 5.47 (s, 2H), 4.03 (s, 2H), 3.64 (t, J = 7.0 Hz, 2H), 3.50 (t, J = 6.1 Hz, 2H), 3.31 (s, 3H), 1.81 (p, J = 6.6 Hz, 2H) | [M + H]$^+$ calculated for molecular formula C$_{23}$H$_{22}$ClFN$_4$O$_4$: 473, observed: 473 |
| 5 | H | | |

Preparation of Compounds 6 and 7

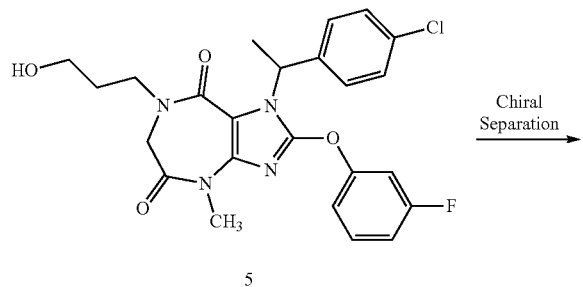

Preparation of Compound 8

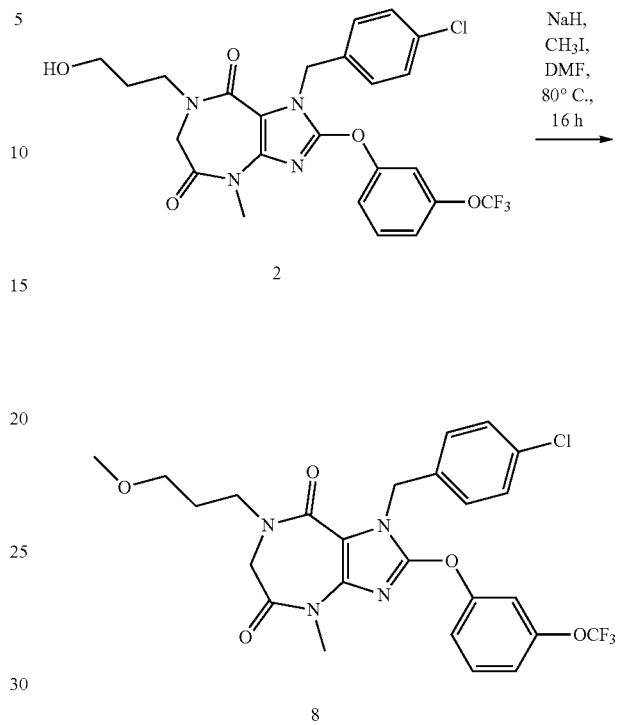

1-[(1R)-1-(4-chlorophenyl)ethyl]-2-(3-fluorophenoxy)-7-(3-hydroxypropyl)-4-methyl-1H,4H,5H,6H,7H,8H-imidazo[4,5-e][1,4]diazepine-5,8-dione and 1-[(1S)-1-(4-chlorophenyl)ethyl]-2-(3-fluorophenoxy)-7-(3-hydroxypropyl)-4-methyl-1H,4H,5H,6H,7H,8H-imidazo[4,5-e][1,4]diazepine-5,8-dione Crude 1-(1-(4-chlorophenyl)ethyl)-2-(3-fluorophenoxy)-7-(3-hydroxypropyl)-4-methyl-1,4,6,7-tetrahydroimidazo[4,5-e][1,4]diazepine-5,8-dione (200 mg) was purified by chiral HPLC with the following conditions (Column: CHIRALPAK IE, 2*25 cm, 5 um; Mobile Phase A: Hexane 0.1% DEA—HPLC, Mobile Phase B: EtOH—HPLC; Flow rate: 17 mL/min; Gradient: 50 B to 50 B in 11 min; 220/254 nm; RT1:7.423; RT2:9.034) to afford the separated enantiomers compound 6 (RT 7.423 min, 73 mg, 23.14%) and compound 7 (RT 9.034 min, 77 mg, 24.41%).

Characterization of Compound 6: $^1$H NMR (400 MHz, Methanol-d4) δ 7.44-7.41 (m, 2H), 7.38-7.31 (m, 3H), 6.98-6.93 (m, 1H), 6.87-6.82 (m, 2H), 6.25 (q, J=7.2 Hz, 1H), 4.16 (s, 2H), 3.73-3.63 (m, 2H), 3.56 (t, J=6.1 Hz, 2H), 3.32 (s, 3H), 2.00 (d, J=7.2 Hz, 3H), 1.85 (p, J=6.6 Hz, 2H). [M+H]$^+$ calculated for molecular formula $C_{24}H_{24}ClFN_4O_4$: 487, observed: 487.

Characterization of Compound 7: $^1$H NMR (400 MHz, Methanol-d4) δ 7.43-7.41 (m, 2H), 7.40-7.30 (m, 3H), 6.98-6.95 (m, 1H), 6.87-6.82 (m, 2H), 6.25 (q, J=7.2 Hz, 1H), 4.17 (s, 2H), 3.68 (t, J=6.8, 2H), 3.56 (t, J=6.1 Hz, 2H), 3.32 (s, 3H), 2.00 (d, J=7.2 Hz, 3H), 1.85 (p, J=6.7 Hz, 2H). [M+H]$^+$ calculated for molecular formula $C_{24}H_{24}ClFN_4O_4$: 487, observed: 487.

1-[(4-chlorophenyl)methyl]-7-(3-methoxypropyl)-4-methyl-2-[3-(trifluoromethoxy)phenoxy]-1H,4H,5H,6H,7H,8H-imidazo[4,5-e][1,4]diazepine-5,8-dione (Compound 8)

To a mixture of 1-[(4-chlorophenyl)methyl]-7-(3-hydroxypropyl)-4-methyl-2-[3-(trifluoromethoxy)phenoxy]-1H,4H,5H,6H,7H,8H-imidazo[4,5-e][1,4]diazepine-5,8-dione (120 mg, 0.22 mmol, 1 equiv.) in DMF (20 mL) was added NaH (44.5 mg, 1.11 mmol, 5 equiv, 60 wt %) at 0° C. under nitrogen atmosphere for 0.5 hours. To the above mixture was added $CH_3I$ (94.8 mg, 0.67 mmol, 3 equiv.) at 0° C. The resulting mixture was stirred for additional 16 hours at 80° C. The mixture was basified to pH 10 with $K_2CO_3$ (aq) and extracted with ethyl acetate (5×50 mL), then the organic layer was washed with brine (2×50 mL) and concentrated under reduced pressure. The residue was purified by reverse phase flash with the following conditions (Column: XBridge Prep OBD C18 Column 30*150 mm 5 um; Mobile Phase A: Water (0.05% TFA), Mobile Phase B: ACN; Flow rate: 60 mL/min; Gradient: 45% B to 80% B in 7 min; 220 nm; RT: 6.55 min) to afford 1-[(4-chlorophenyl)methyl]-7-(3-methoxypropyl)-4-methyl-2-[3-(trifluoromethoxy)phenoxy]-1H,4H,5H,6H,7H,8H-imidazo[4,5-e][1,4]diazepine-5,8-dione (34.1 mg, 27.70%) as a light yellow oil. $^1$H NMR (400 MHz, Methanol-d4) δ 7.52 (t, J=8.2 Hz, 1H), 7.36-7.28 (m, 6H), 7.20 (d, J=8.1 Hz, 1H), 5.50 (s, 2H), 4.05 (s, 2H), 3.63 (t, J=6.9 Hz, 2H), 3.37-3.32 (m, 5H), 3.29 (s, 3H), 1.89-1.82 (m, 2H). [M+H]$^+$ calculated for molecular formula $C_{25}H_{24}ClF_3N_4O_5$: 553, observed: 553.

Preparation of Compound 9

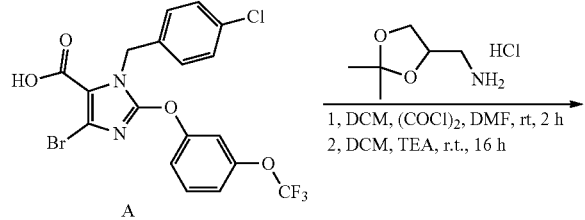

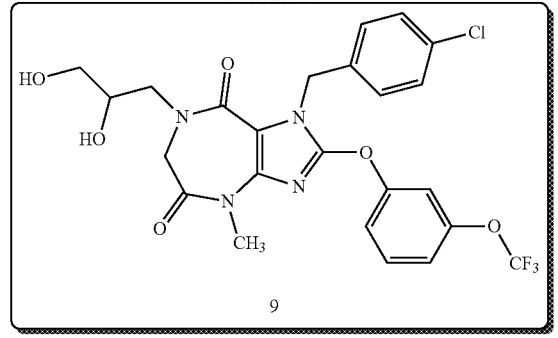

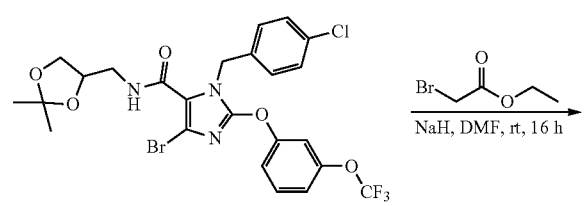

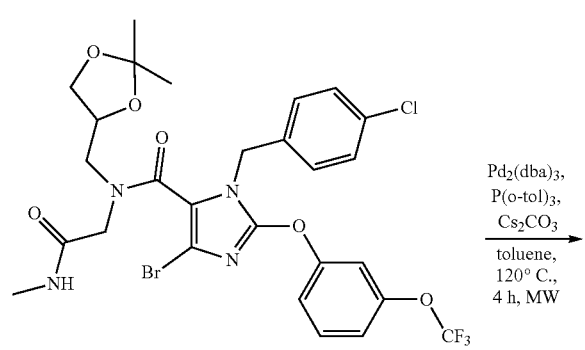

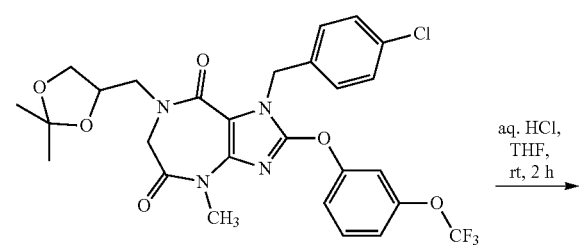

4-bromo-1-[(4-chlorophenyl)methyl]-N-[(2,2-dimethyl-1,3-dioxolan-4-yl)methyl]-2-[3-(trifluoromethoxy)phenoxy]-1H-imidazole-5-carboxamide To a mixture of (2,2-dimethyl-1,3-dioxolan-4-yl)methanamine (617.2 mg, 4.71 mmol, 2.0 equiv.) in DCM (30 mL) and TEA (1.0 mL, 9.69 mmol, 3.0 equiv.) was added dropwise 4-bromo-1-[(4-chlorophenyl)methyl]-2-[3-(trifluoromethoxy)phenoxy]-1H-imidazole-5-carbonyl chloride (1.2 g, 2.35 mmol, 1 equiv.) in DCM (20 mL) at 0° C. The resulting mixture was warmed to room temperature and stirred at room temperature for 16 hours. The reaction mixture was concentrated under reduced pressure which was purified by silica gel column chromatography, eluted with PE:EtOAc (3:1 to 2:1) to afford 4-bromo-1-[(4-chlorophenyl)methyl]-N-[(2,2-dimethyl-1,3-dioxolan-4-yl)methyl]-2-[3-(trifluoromethoxy)phenoxy]-1H-imidazole-5-carboxamide (1.30 g, 91.37%) as a light yellow oil. $^1$H NMR (300 MHz, Chloroform-d) δ 7.46-7.38 (m, 1H), 7.35-7.29 (m, 2H), 7.27-7.16 (m, 3H), 7.15-7.08 (m, 2H), 7.01 (t, J=5.6 Hz, 1H), 5.59 (s, 2H), 4.32 (qd, J=6.2, 3.8 Hz, 1H), 4.07 (dd, J=8.4, 6.4 Hz, 1H), 3.71-3.62 (m, 2H), 3.57 (dt, J=14.1, 5.8 Hz, 1H), 1.47 (s, 3H), 1.38 (s, 3H).

ethyl 2-(1-[4-bromo-1-[(4-chlorophenyl)methyl]-2-[3-(trifluoromethoxy)phenoxy]-1H-imidazol-5-yl]-N-[(2,2-dimethyl-1,3-dioxolan-4-yl)methyl]formamido)acetate To a mixture of 4-bromo-1-[(4-chlorophenyl)methyl]-N-[(2,2-dimethyl-1,3-dioxolan-4-yl)methyl]-2-[3-(trifluoromethoxy)phenoxy]-1H-imidazole-5-carboxamide (1 g, 1.65 mol, 1 equiv.) in DMF (20 mL) was added NaH (99.2 mg, 2.48 mmol, 1.5 equiv, 60 wt %) at 0° C. under nitrogen atmosphere for 0.5 hours. To the above mixture was added ethyl 2-bromoacetate (0.3 mL, 1.80 mmol, 1.636 equiv.) at 0° C. The resulting mixture was stirred for additional 16 hours at room temperature. The resulting mixture was added ethyl acetate (300 mL) and brine (100 mL), then the water layer was extracted with ethyl acetate (100 mL). The combined organic layer was dried over anhydrous Na$_2$SO$_4$ and filtered. The filtrate was concentrated to give the crude product which was purified by silica gel column chromatography, eluted with PE:EA (20:1 to 4:1) to afford ethyl 2-(1-[4-bromo-1-[(4-chlorophenyl)methyl]-2-[3-(trifluoromethoxy)phenoxy]-1H-imidazol-5-yl]-N-[(2,2-dimethyl-1,3-dioxolan-4-yl)methyl]formamido)acetate (1.1 g, 96.3%) as a light yellow oil.

2-(1-[4-bromo-1-[(4-chlorophenyl)methyl]-2-[3-(trifluoromethoxy)phenoxy]-1H-imidazol-5-yl]-N-[(2,2-dimethyl-1,3-dioxolan-4-yl)methyl]formamido)-N-methylacetamide A mixture of ethyl 2-(1-[4-bromo-1-[(4-chlorophenyl)methyl]-2-[3-(trifluoromethoxy)phenoxy]-1H-imidazol-5-yl]-N-[(2,2-dimethyl-1,3-dioxolan-4-yl)methyl]formamido)acetate (1.2 g, 1.74 mmol, 1 equiv.) in 2M methylamine in methanol (5 mL) was irradiated with microwave radiation for 1 hour at 60° C. The mixture was allowed to cool down to room temperature. The reaction mixture was concentrated to give the crude product which was purified by silica gel column chromatography, eluted with PE:EA (1:1 to 1:8) to afford 2-(1-[4-bromo-1-[(4-chlorophenyl)methyl]-2-[3-(trifluoromethoxy)phenoxy]-1H-imidazol-5-yl]-N-[(2,2-dimethyl-1,3-dioxolan-4-yl)methyl]formamido)-N-methylacetamide (0.92 g, 78.37%) as an white solid.

1-[(4-chlorophenyl)methyl]-7-[(2,2-dimethyl-1,3-dioxolan-4-yl)methyl]-4-methyl-2-[3-(trifluoromethoxy)phenoxy]-1H,4H,5H,6H,7H,8H-imidazo[4,5-e][1,4]diazepine-5,8-dione A mixture of 2-(1-[4-bromo-1-[(4-chlorophenyl)methyl]-2-[3-(trifluoromethoxy)phenoxy]-1H-imidazol-5-yl]-N-[(2,2-dimethyl-1,3-dioxolan-4-yl)methyl]formamido)-N-methylacetamide (1 g, 1.48 mmol, 1 equiv.), Pd$_2$(dba)$_3$·CHCl$_3$ (150 mg, 0.14 mmol, 0.098 equiv.), P(o-Tol)$_3$ (90 mg, 0.30 mmol, 0.200 equiv.) and Cs$_2$CO$_3$ (1 g, 3.07 mmol, 2.074 equiv.) in Toluene (15 mL) was irradiated with microwave radiation for 4 hours at 120° C. The mixture was allowed to cool down to room temperature. The reaction mixture was filtered and the filtrate was concentrated to give the crude product which was purified by silica gel column chromatography, eluted with PE:EA (4:1 to 2:3) to afford 1-[(4-chlorophenyl)methyl]-7-[(2,2-dimethyl-1,3-dioxolan-4-yl)methyl]-4-methyl-2-[3-(trifluoromethoxy)phenoxy]-1H,4H,5H,6H,7H,8H-imidazo[4,5-e][1,4]diazepine-5,8-dione (470 mg, 53.39%) as a light yellow oil.

1-[(4-chlorophenyl)methyl]-7-(2,3-dihydroxypropyl)-4-methyl-2-[3-(trifluoromethoxy)phenoxy]-1H,4H,5H,6H,7H,8H-imidazo[4,5-e][1,4]diazepine-5,8-dione (Compound 9)

To a stirred solution of 1-[(4-chlorophenyl)methyl]-7-[(2,2-dimethyl-1,3-dioxolan-4-yl)methyl]-4-methyl-2-[3-(trifluoromethoxy)phenoxy]-1H,4H,5H,6H,7H,8H-imidazo[4,5-e][1,4]diazepine-5,8-dione (600 mg, 1.01 mol, 1 equiv.) in THF (15 mL) was added dropwise HCl (15 mL) in H$_2$O (15.0 mL) at room temperature. Then the resulting mixture was stirred at room temperature for 2 hours. The mixture was basified to pH 10 with K$_2$CO$_3$ (aq) and extracted with ethyl acetate (5×50 mL), then the organic layer was washed with brine (2×50 mL) and concentrated under reduced pressure. The residue was purified by reverse phase flash with the following conditions (Column: Spherical C18 Column, 20-40 um, 330 g; Mobile Phase A: Water (0.1% HOAc), Mobile Phase B: ACN; Flow rate: 80 mL/min; Gradient: 60% B to 95% B in 35 min, 254 nm) to afford 1-[(4-chlorophenyl)methyl]-7-(2,3-dihydroxypropyl)-4-methyl-2-[3-(trifluoromethoxy)phenoxy]-1H,4H,5H,6H,7H,8H-imidazo[4,5-e][1,4]diazepine-5,8-dione (520 mg, 92.92%) as a white solid. $^1$H NMR (300 MHz, DMSO-d6) δ 7.57 (t, J=8.3 Hz, 1H), 7.41-7.35 (m, 7H), 5.44 (d, J=1.8 Hz, 2H), 4.81 (d, J=5.3 Hz, 1H), 4.63 (t, J=5.7 Hz, 1H), 4.25-4.01 (m, 2H), 3.83-3.62 (m, 1H), 3.55-3.48 (m, 1H), 3.43-3.40 (m, 1H), 3.32-3.24 (m, 2H), 3.19 (s, 3H). [M+H]$^+$ calculated for molecular formula C$_{24}$H$_{22}$ClF$_3$N$_4$O$_6$: 555, observed: 555

Preparation of Compound 10

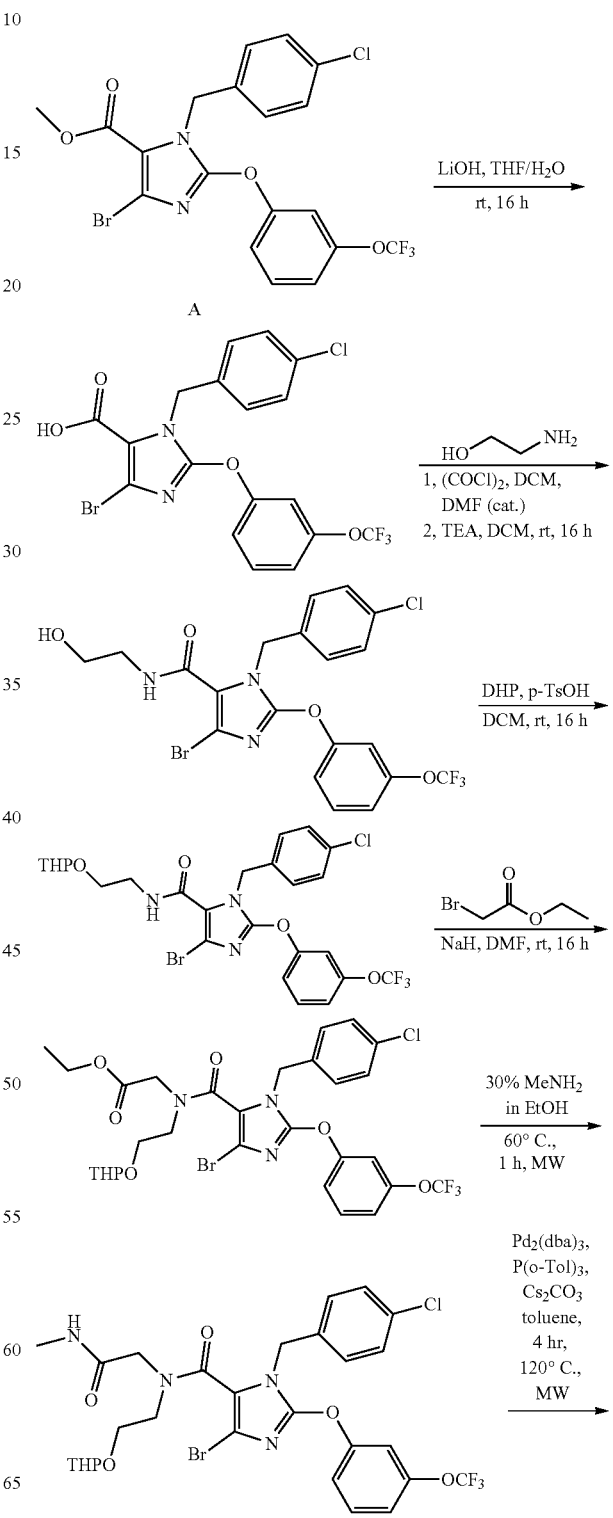

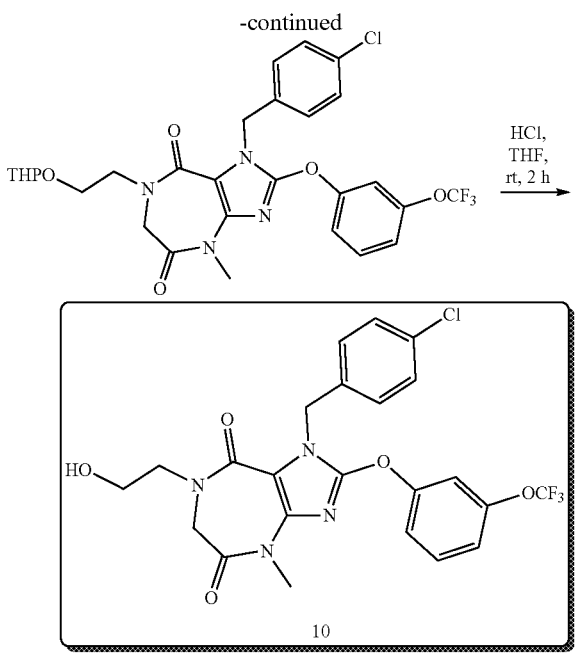

-continued 4-bromo-1-[(4-chlorophenyl)methyl]-2-[3-(trifluoromethoxy)phenoxy]-1H-imidazole-5-carboxylic acid A mixture of methyl 4-bromo-1-[(4-chlorophenyl)methyl]-2-[3-(trifluoromethoxy)phenoxy]-1H-imidazole-5-carboxylate (2.5 g, 4.94 mmol, 1 equiv.) and LiOH (1.2 g, 49.44 mmol, 10 equiv.) in THF(50 mL) and H$_2$O (50 mL) was stirred for 10 hours at room temperature. The resulting mixture was extracted with EA (4×200 mL). The combined organic layers were washed with water (1×100 mL), dried over anhydrous Na$_2$SO$_4$. After filtration, the filtrate was concentrated under reduced pressure. The residue/crude product was purified by reverse phase flash with the following conditions (Column: Spherical C18 Column, 20-40 um, 120 g. Mobile Phase A: Water (0.1% AcOH), Mobile Phase B: ACN, Flow rate: 60 mL/min, Gradient:80-90% B in 15 min, 254 nm.) to afford 4-bromo-1-[(4-chlorophenyl)methyl]-2-[3-(trifluoromethoxy)phenoxy]-1H-imidazole-5-carboxylic acid (2.1 g, 86.40%) as a white solid. $^1$H NMR (400 MHz, DMSO-d6) δ 13.41 (s, 1H), 7.59 (t, J=8.3 Hz, 1H), 7.42 (dd, J=8.7, 2.1 Hz, 3H), 7.37 (dt, J=8.2, 1.5 Hz, 1H), 7.33-7.29 (m, 1H), 7.29-7.24 (m, 2H), 5.51 (s, 2H).

4-bromo-1-[(4-chlorophenyl)methyl]-N-(2-hydroxyethyl)-2-[3-(trifluoromethoxy)phenoxy]-1H-imidazole-5-carboxamide A mixture of 4-bromo-1-[(4-chlorophenyl)methyl]-2-[3-(trifluoromethoxy)phenoxy]-1H-imidazole-5-carboxylic acid (1.1 g, 2.24 mmol, 1 equiv.) and 1 drop DMF in DCM (20 mL) was added oxalic dichloride (0.9 g, 6.71 mmol, 3 equiv.) dropwise at 0° C. The mixture was stirred 3 hours at room temperature. The resulting mixture was concentrated under vacuum. The solid was dissolved with DCM (30 mL) to give solution A for the next reaction. A mixture of 2-aminoethan-1-ol (0.4 g, 6.71 mmol, 3 equiv.) and triethylamine (0.7 g, 6.71 mmol, 3 equiv.) in DCM (10 mL) was cooled to 0° C., solution A was added dropwise at 0° C. under nitrogen atmosphere. The mixture was stirred for 3 hours at room temperature. The resulting mixture was concentrated under reduced pressure. The residue was purified by silica gel column chromatography, eluted with PE/EA (2/1 to 1/1) to afford 4-bromo-1-[(4-chlorophenyl)methyl]-N-(2-hydroxyethyl)-2-[3-(trifluoromethoxy)phenoxy]-1H-imidazole-5-carboxamide (0.91 g, 76.06%) as a white solid. $^1$H NMR (400 MHz, DMSO-d6) δ 7.99 (t, J=5.6 Hz, 1H), 7.58 (t, J=8.3 Hz, 1H), 7.45-7.37 (m, 2H), 7.38-7.26 (m, 5H), 5.39 (s, 2H), 4.77 (t, J=5.4 Hz, 1H), 3.47 (q, J=6.1 Hz, 2H), 3.35-3.27 (m, 2H).

4-bromo-1-[(4-chlorophenyl)methyl]-N-[2-(oxan-2-yloxy)ethyl]-2-[3-(trifluoromethoxy)phenoxy]-1H-imidazole-5-carboxamide To a stirred mixture of 4-bromo-1-[(4-chlorophenyl)methyl]-N-(2-hydroxyethyl)-2-[3-(trifluoromethoxy)phenoxy]-1H-imidazole-5-carboxamide (0.9 g, 1.68 mmol, 1 equiv.) and 4-methylbenzene-1-sulfonic acid (0.0 g, 0.17 mmol, 0.1 equiv.) in DCM (50 mL) was added 3,4-dihydro-2H-pyran (0.0 g, 0.34 mmol, 0.2 equiv.) at room temperature under nitrogen atmosphere. The mixture was reacted for 10 hours at room temperature. The resulting mixture was quenched with water (100 mL) and was extracted with DCM (4×100 mL). The combined organic layers were washed with water (1×100 mL), dried over anhydrous Na$_2$SO$_4$. After filtration, the filtrate was concentrated under reduced pressure. The residue was purified by silica gel column chromatography, eluted with PE/EA (4/1) to afford 4-bromo-1-[(4-chlorophenyl)methyl]-N-[2-(oxan-2-yloxy)ethyl]-2-[3-(trifluoromethoxy)phenoxy]-1H-imidazole-5-carboxamide (0.8 g, 76.81%) as a yellow oil. $^1$H NMR (400 MHz, DMSO-d6) δ 8.09 (d, J=5.6 Hz, 1H), 7.60-7.55 (m, 1H), 7.43-7.38 (m, 2H), 7.36-7.25 (m, 5H), 5.38 (s, 2H), 4.59 (d, J=4.0 Hz, 1H), 3.76-3.66 (m, 2H), 3.42 (dq, J=10.2, 5.9, 5.4 Hz, 4H), 1.50-1.41 (m, 6H).

ethyl 2-(1-[4-bromo-1-[(4-chlorophenyl)methyl]-2-[3-(trifluoromethoxy)phenoxy]-1H-imidazol-5-yl]-N-[2-(oxan-2-yloxy)ethyl]formamido)acetate To a stirred solution of 4-bromo-1-[(4-chlorophenyl)methyl]-N-[2-(oxan-2-yloxy)ethyl]-2-[3-(trifluoromethoxy)phenoxy]-1H-imidazole-5-carboxamide (0.64 g, 1.03 mmol, 1 equiv.) in DMF(15 mL) was added NaH (0.1 g, 4.14 mmol, 4 equiv.) in portions at 0° C. under nitrogen atmosphere. The mixture was stirred for 30 min at 0° C. and was added ethyl 2-bromoacetate (0.7 g, 4.14 mmol, 4 equiv.). The mixture was stirred for 16 hours at room temperature. The resulting mixture was quenched with water (100 mL) and extracted with EA (3×100 mL). The combined organic layers were washed with water (1×100 mL), dried over anhydrous Na$_2$SO$_4$. After filtration, the filtrate was concentrated under reduced pressure to gain crude compound. The crude product was purified by reverse phase flash with the following conditions (Column: Spherical C18 Column, 20-40 um, 120 g. Mobile Phase A: Water (0.1% AcOH), Mobile Phase B: ACN, Flow rate: 60 mL/min, Gradient:60-80% B in 35 min, 254 nm) to afford ethyl 2-(1-[4-bromo-1-[(4-chlorophenyl)methyl]-2-[3-(trifluoromethoxy)phenoxy]-1H-imidazol-5-yl]-N-[2-(oxan-2-yloxy)ethyl]formamido)acetate (400 mg, 54.87%) as a yellow oil.

2-(1-[4-bromo-1-[(4-chlorophenyl)methyl]-2-[3-(trifluoromethoxy)phenoxy]-1H-imidazol-5-yl]-N-[2-(oxan-2-yloxy)ethyl]formamido)-N-methylacetamide Into a 20 mL vessel were added ethyl 2-(1-[4-bromo-1-[(4-chlorophenyl)methyl]-2-[3-(trifluoromethoxy)phenoxy]-1H-imidazol-5-yl]-N-[2-(oxan-2-yloxy)ethyl]formamido)acetate(0.4 g, 0.57 mmol, 1 equiv.) and $CH_3NH_2$ MeOH (6 mL, 30%) at room temperature. The mixture was reacted at 60° C. for 1 hour under microwave irradiation. The resulting mixture was allowed to cool down to room temperature and concentrated under vacuum. The residue was purified by silica gel column chromatography, eluted with PE/EA (1/1) to afford 2-(1-[4-bromo-1-[(4-chlorophenyl)methyl]-2-[3-(trifluoromethoxy)phenoxy]-1H-imidazol-5-yl]-N-[2-(oxan-2-yloxy)ethyl]formamido)-N-methylacetamide(0.28 g, 71.52%) as a yellow oil. $^1$H NMR (400 MHz, Chloroform-d) δ 7.42 (d, J=8.5 Hz, 1H), 7.33 (d, J=8.6 Hz, 3H), 7.14 (dd, J=31.1, 7.5 Hz, 4H), 5.17 (s, 2H), 4.41 (s, 1H), 4.17 (s, 2H), 3.75 (d, J=53.6 Hz, 4H), 3.51 (s, 2H), 2.82 (s, 3H), 1.73 (d, J=36.0 Hz, 6H).

1-[(4-chlorophenyl)methyl]-4-methyl-7-[2-(oxan-2-yloxy)ethyl]-2-[3-(trifluoromethoxy)phenoxy]-1H,4H,5H,6H,7H,8H-imidazo[4,5-e][1,4]diazepine-5,8-dione Into a 20 mL vessel were added 2-(1-[4-bromo-1-[(4-chlorophenyl)methyl]-2-[3-(trifluoromethoxy)phenoxy]-1H-imidazol-5-yl]-N-[2-(oxan-2-yloxy)ethyl]formamido)-N-methylacetamide (280 mg, 0.41 mmol, 1 equiv.), $Pd_2(dba)_3$ (55.9 mg, 0.06 mmol, 0.150 equiv.), $Cs_2CO_3$ (397.7 mg, 1.22 mmol, 3.008 equiv.) and tris(2-methylphenyl)phosphane (37.23 mg, 0.12 mmol, 0.301 equiv.) at room temperature. The mixture was heated for 4 hours at 120° C. under microwave condition. The mixture was allowed to cool down to room temperature. The residue was purified by silica gel column chromatography, eluted with PE/EA (1/1) to afford 1-[(4-chlorophenyl)methyl]-4-methyl-7-[2-(oxan-2-yloxy)ethyl]-2-[3-(trifluoromethoxy)phenoxy]-1H,4H,5H,6H,7H,8H-imidazo[4,5-e][1,4]diazepine-5,8-dione(110 mg, 44.51%) as a yellow oil.

1-[(4-chlorophenyl)methyl]-7-(2-hydroxyethyl)-4-methyl-2-[3-(trifluoromethoxy)phenoxy]-1H,4H,5H,6H,7H,8H-imidazo[4,5-e][1,4]diazepine-5,8-dione (Compound 10)

A mixture of 1-[(4-chlorophenyl)methyl]-4-methyl-7-[2-(oxan-2-yloxy)ethyl]-2-[3-(trifluoromethoxy)phenoxy]-1H,4H,5H,6H,7H,8H-imidazo[4,5-e][1,4]diazepine-5,8-dione (120 mg, 200 mmol, 1 equiv.) and 2M HCl (20 mL) in THF (20 mL) was stirred for 1 hour at room temperature. The reaction was monitored by LCMS. The resulting mixture was extracted with EA (3×200 mL). The combined organic layers were washed with water (1×200 mL), dried over anhydrous $Na_2SO_4$. After filtration, the filtrate was concentrated under reduced pressure. The crude product (88 mg) was purified by Prep-HPLC with the following conditions (Column: XBridge Prep C18 OBD Column, 5 um, 19*150 mm; Mobile Phase A: Water(0.05% TFA), Mobile Phase B: ACN; Flow rate: 20 mL/min; Gradient: 35% B to 60% B in 12 min; 254 nm; RT: 11.70 min.) to afford 1-[(4-chlorophenyl)methyl]-7-(2-hydroxyethyl)-4-methyl-2-[3-(trifluoromethoxy)phenoxy]-1H,4H,5H,6H,7H,8H-imidazo[4,5-e][1,4]diazepine-5,8-dione (60 mg, 73.28%) as a yellow semi-solid. $^1$H NMR (400 MHz, Methanol-d4) δ 7.52 (t, J=8.3 Hz, 1H), 7.34-7.27 (m, 6H), 7.20 (d, J=8.3 Hz, 1H), 5.51 (s, 2H), 4.14 (s, 2H), 3.74 (t, J=5.5 Hz, 2H), 3.67 (t, J=5.6 Hz, 2H), 3.33 (s, 3H). [M+H]$^+$ calculated for molecular formula $C_{23}H_{20}ClF_3N_4O_5$: 525, observed: 525

Preparation of compounds 11-14 shown in the table below follows the methods and protocols as described for the synthesis of compound 10, starting with the appropriate amine:

| Compound | Amine | NMR |
|---|---|---|
| 11 | ethyl 3-amino-2,2-difluoropropanoate hydrochloride | $^1$H NMR (400 MHz, Methal-d4) δ 7.53 (, J = 8.3 Hz, 1H), 7.39-7.23 (m, 6H), 7.21 (d, J = 8.4 Hz, 1H), 5.51 (s, 2H), 4.17 (s, 2H), 4.05 (t, J = 13.8 Hz, 2H), 3.64 (t, J = 13.1 Hz, 2H), 3.33 (s, 3H). |
| 12 | 3-aminocyclobutan-1-ol | $^1$H NMR (400 MHz, Methanol-d4) δ 7.52 (t, J = 8.1 Hz, 1H), 7.38-7.24 (m, 6H), 7.20 (d, J = 8.3 Hz, 1H), 5.51 (s, 2H), 5.20 (t, J = 8.3 Hz, 1H), 4.41 (d, J = 7.0 Hz, 1H), 4.08 (s, 2H), 3.33 (s, 3H), 2.60-2.53 (m, 2H), 2.28-2.23 (m, 2H). |
| 13 | 3-aminocyclobutan-1-ol | $^1$H NMR (400 MHz, Methanol-d4) δ 7.51 (t, J = 8.2 Hz, 1H), 7.38-7.24 (m, 6H), 7.24-7.16 (m, 1H), 5.51 (s, 2H), 4.41 (tt, J = 9.8, 7.5 Hz, 1H), 4.11 (s, 2H), 4.01 (p, J = 7.2 Hz, 1H), 3.33 (s, 3H), 2.62 (m, 2H), 2.16 (m, 2H) |
| 14 | rac-trans-3-aminocyclopentan-1-ol | |

Preparation of Compounds 15 and 16

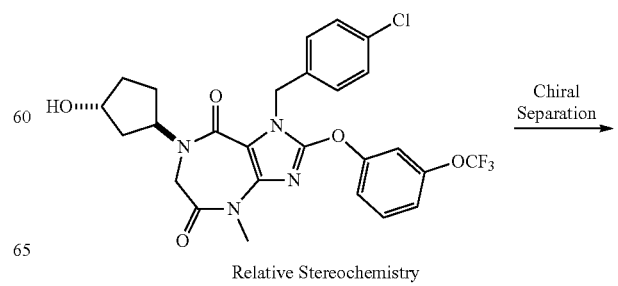

Relative Stereochemistry

-continued

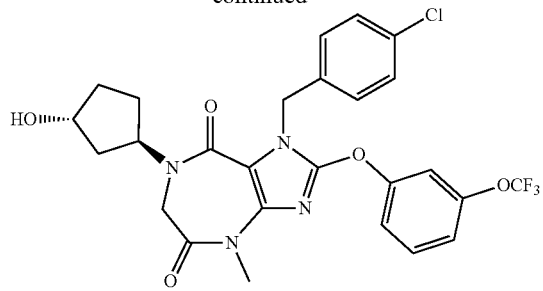

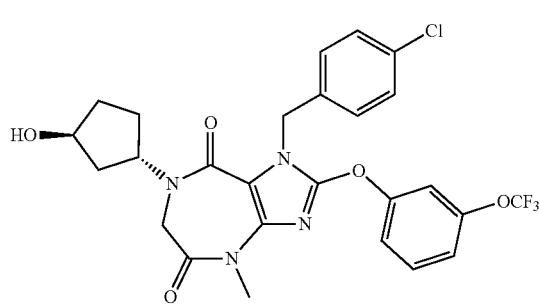

1-[(4-chlorophenyl)methyl]-7-[(1R,3R)-3-hydroxy-cyclopentyl]-4-methyl-2-[3-(trifluoromethoxy)phenoxy]-1H,4H,5H,6H,7H,8H-imidazo[4,5-e][1,4]diazepine-5,8-dione and 1-[(4-chlorophenyl)methyl]-7-[(1S,3S)-3-hydroxycyclopentyl]-4-methyl-2-[3-(trifluoromethoxy)phenoxy]-1H,4H,5H,6H,7H,8H-imidazo[4,5-e][1,4]diazepine-5,8-dione Crude 1-(4-chlorobenzyl)-7-((trans-3-hydroxycyclopentyl)-4-methyl-2-(3-(trifluoromethoxy)phenoxy)-1,4,6,7-tetrahydroimidazo[4,5-e][1,4]diazepine-5,8-dione was purified by chiral Prep-HPLC with the following conditions (Column: CHIRALPAK IC, 2*25 cm, 5 um; Mobile Phase A: Hexane 0.1% DEA—HPLC, Mobile Phase B: EtOH—HPLC; Flow rate: 20 mL/min; Gradient: 20 B to 20 B in 18 min; 220/254 nm; RT1:12.901; RT2:15.068) to provide compound 15 (RT 12.901 min, 23.8 mg, 16.08%) and compound 16 (RT 15.068 min, 22.0 mg, 14.87%).

Compound 15 characterization: $^1$H NMR (400 MHz, Methanol-d4) δ 7.52 (t, J=8.3 Hz, 1H), 7.43-7.24 (m, 6H), 7.20 (d, J=8.4 Hz, 1H), 5.51 (s, 2H), 5.17 (p, J=8.5 Hz, 1H), 4.40 (s, 1H), 3.93 (s, 2H), 3.33 (s, 3H), 2.10-2.09 (m, 2H), 1.99-1.97 (m, 2H), 1.68-1.59 (m, 2H). [M+H]$^+$ calculated for molecular formula $C_{26}H_{24}ClF_3N_4O_5$: 565, observed: 565.

Compound 16 characterization: $^1$H NMR (400 MHz, Methanol-d4) δ 7.52 (t, J=8.3 Hz, 1H), 7.36-7.27 (m, 6H), 7.20 (d, J=8.4 Hz, 1H), 5.51 (s, 2H), 5.18 (p, J=8.5 Hz, 1H), 4.40 (s, 1H), 3.93 (s, 2H), 3.33 (s, 3H), 2.10-2.08 (m, 2H), 1.87-1.77 (m, 2H), 1.68-1.59 (m, 2H). [M+H]$^+$ calculated for molecular formula $C_{26}H_{24}ClF_3N_4O_5$: 565, observed: 565.

Preparation of Compounds 17 and 18

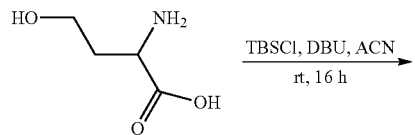

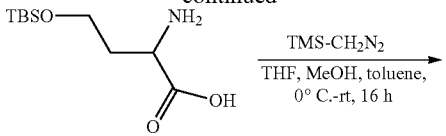

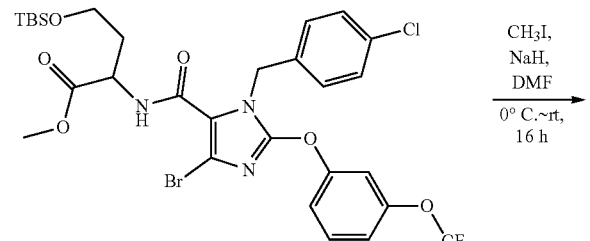

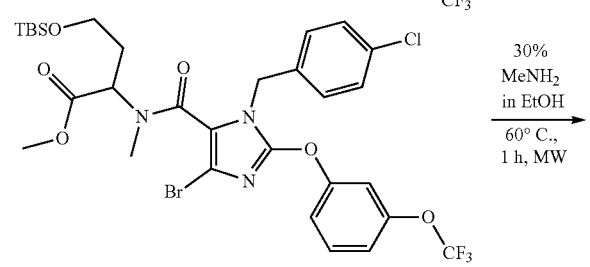

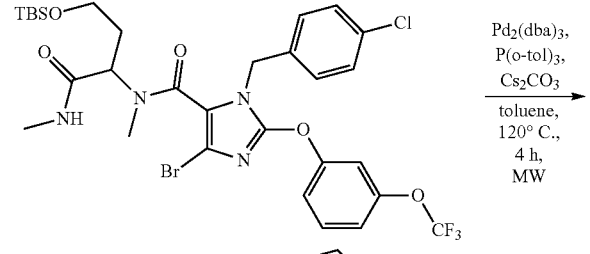

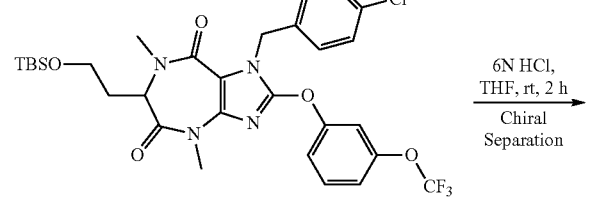

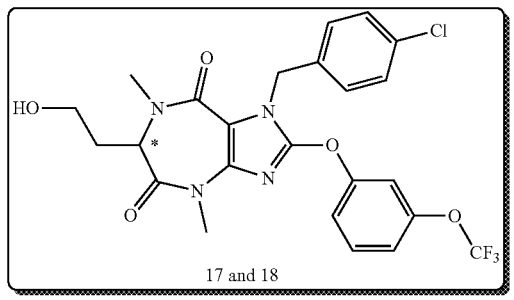

17 and 18

2-amino-4-[(tert-butyldimethylsilyl)oxy]butanoic acid

To a stirred solution of 2-amino-4-hydroxybutanoic acid (5.0 g, 41.97 mmol, 1 equiv.) in MeCN (150 mL) and DBU (6.6 mL, 43.25 mmol, 1.05 equiv.) was added slowly TBSCl (6.6 g, 44.07 mmol, 1.05 equiv.) at 0° C. The resulting mixture was warmed to room temperature and stirred at room temperature for 16 hours. The reaction mixture was filtered, the filter cake was washed with MeCN (3×50 mL). The combined filtrate was concentrated to afford 2-amino-4-[(tert-butyldimethylsilyl)oxy]butanoic acid (8.5 g, crude). $^1$H NMR (300 MHz, Methanol-d4) δ 3.89 (t, J=6.1 Hz, 2H), 3.79 (t, J=5.9 Hz, 1H), 3.74-3.55 (m, 2H), 0.95 (s, 9H), 0.14 (s, 6H).

methyl 2-amino-4-[(tert-butyldimethylsilyl)oxy]butanoate

To a mixture of 2-amino-4-[(tert-butyldimethylsilyl)oxy]butanoic acid (5 g, 21.42 mmol, 1 equiv.) in toluene (200 mL) and MeOH (50 mL) was added trimethylsilyl diazomethane (60 mL, 0.53 mmol, 0.025 equiv.) at room temperature. The resulting mixture was stirred for 16 hours at room temperature. The reaction mixture was concentrated to afford methyl 2-amino-4-[(tert-butyldimethylsilyl)oxy]butanoate (5 g, crude) as a light yellow oil.

methyl 2-([4-bromo-1-[(4-chlorophenyl)methyl]-2-[3-(trifluoromethoxy)phenoxy]-1H-imidazol-5-yl]formamido)-4-[(tert-butyldimethylsilyl)oxy]butanoate A mixture of 4-bromo-1-[(4-chlorophenyl)methyl]-2-[3-(trifluoromethoxy)phenoxy]-1H-imidazole-5-carboxylic acid (1.1 g, 2.24 mmol, 1 equiv.) and (COCl)$_2$ (0.6 mL, 4.73 mmol, 3.148 equiv.) in DCM (20.0 mL) and DMF (5 drops) was stirred at room temperature for 1 hour. The resulting mixture was concentrated to give the crude product. To the above crude product was added methyl 2-amino-4-[(tert-butyldimethylsilyl)oxy]butanoate (1.1 g, 4.45 mmol, 1.987 equiv.), TEA (1.6 mL, 15.37 mmol, 5 equiv.) and DCM (25.0 mL), then the resulting mixture was stirred at room temperature for 4 hours. The reaction mixture was purified by silica gel column chromatography, eluted with PE:EA (20:1 to 5:1) to afford methyl 2-([4-bromo-1-[(4-chlorophenyl)methyl]-2-[3-(trifluoromethoxy)phenoxy]-1H-imidazol-5-yl]formamido)-4-[(tert-butyldimethylsilyl)oxy]butanoate (1.2 g, 74.38%) as a light yellow oil. $^1$H NMR (400 MHz, DMSO-d6) δ 8.51 (d, J=7.6 Hz, 1H), 7.68-7.53 (m, 1H), 7.44-7.23 (m, 7H), 5.47-5.26 (m, 2H), 4.55 (ddd, J=9.5, 7.5, 4.3 Hz, 1H), 3.70 (dd, J=7.1, 4.7 Hz, 2H), 3.34 (s, 3H), 2.08-1.89 (m, 2H), 0.85 (s, 9H), 0.01 (d, J=5.2 Hz, 7H).

methyl 2-(1-[4-bromo-1-[(4-chlorophenyl)methyl]-2-[3-(trifluoromethoxy)phenoxy]-1H-imidazol-5-yl]-N-methylformamido)-4-[(tert-butyldimethylsilyl)oxy]butanoate To a mixture of methyl 2-([4-bromo-1-[(4-chlorophenyl)methyl]-2-[3-(trifluoromethoxy)phenoxy]-1H-imidazol-5-yl]formamido)-4-[(tert-butyldimethylsilyl)oxy]butanoate (1.2 g, 1.66 mmol, 1 equiv.) in DMF (20 mL) was added NaH (100 mg, 2.50 mmol, 1.502 equiv., 60 wt %) at 0° C. under nitrogen atmosphere for 0.5 hours. To the above mixture was added CH$_3$I (0.2 mL, 3.21 mmol, 1.930 equiv.) at 0° C. The resulting mixture was stirred for additional 16 hours at room temperature. The resulting mixture was added ethyl acetate (300 mL) and brine (300 mL), then the water layer was extracted with ethyl acetate (200 mL). The combined organic layer was dried over anhydrous Na$_2$SO$_4$ and filtered. The filtrate was purified by silica gel column chromatography, eluted with PE:EA (20:1 to 6:1) to afford methyl 2-(1-[4-bromo-1-[(4-chlorophenyl)methyl]-2-[3-(trifluoromethoxy)phenoxy]-1H-imidazol-5-yl]-N-methylformamido)-4-[(tert-butyldimethylsilyl)oxy]butanoate (880 mg, 71.93%) as a light yellow oil.

2-(1-[4-bromo-1-[(4-chlorophenyl)methyl]-2-[3-(trifluoromethoxy)phenoxy]-1H-imidazol-5-yl]-N-methylformamido)-4-[(tert-butyldimethylsilyl)oxy]-N-methylbutanamide A mixture of methyl 2-(1-[4-bromo-1-[(4-chlorophenyl)methyl]-2-[3-(trifluoromethoxy)phenoxy]-1H-imidazol-5-yl]-N-methylformamido)-4-[(tert-butyldimethylsilyl)oxy]butanoate (1.1 g, 1.50 mmol, 1 equiv.) in 2M methylamine in methanol (5 mL) was irradiated with microwave radiation for 1 hour at 60° C. The reaction mixture was purified by silica gel column chromatography, eluted with PE:EA (1:1 to 1:8) to afford 2-(1-[4-bromo-1-[(4-chlorophenyl)methyl]-2-[3-(trifluoromethoxy)phenoxy]-1H-imidazol-5-yl]-N-methylformamido)-4-[(tert-butyldimethylsilyl)oxy]-N-methylbutanamide (550 mg, 50.07%) as a light yellow oil. $^1$H NMR (300 MHz, DMSO-d6) δ 7.70 (s, 1H), 7.58 (t, J=8.2 Hz, 1H), 7.46-7.21 (m, 6H), 5.16 (s, 2H), 4.94 (s, 1H), 3.60 (s, 3H), 2.88 (s, 3H), 2.60 (d, J=4.5 Hz, 3H), 2.03 (d, J=8.7 Hz, 1H), 1.90 (d, J=12.3 Hz, 1H), 0.86 (s, 9H), 0.02 (d, J=2.7 Hz, 6H).

6-[2-[(tert-butyldimethylsilyl)oxy]ethyl]-1-[(4-chlorophenyl)methyl]-4,7-dimethyl-2-[3-(trifluoromethoxy)phenoxy]-1H,4H,5H,6H,7H,8H-imidazo[4,5-e][1,4]diazepine-5,8-dione A mixture of 2-(1-[4-bromo-1-[(4-chlorophenyl)methyl]-2-[3-(trifluoromethoxy)phenoxy]-1H-imidazol-5-yl]-N-methylformamido)-4-[(tert-butyldimethylsilyl)oxy]-N-methylbutanamide (450 mg, 610 mmol, 1 equiv.), Pd$_2$(dba)$_3$·CHCl$_3$ (63.45 mg, 0.06 mmol, 0.100 equiv.), P(o-Tol)$_3$ (37.35 mg, 0.12 mmol, 0.200 equiv.) and Cs$_2$CO$_3$ (400 mg, 1.23 mmol, 2.003 equiv.) in Toluene (8 mL) was irradiated with microwave radiation for 4 hours at 120° C. The mixture was allowed to cool down to room temperature. The reaction mixture was filtered and the filtrate was concentrated to give the crude product which was purified by silica gel column chromatography, eluted with PE:EA (2:1 to 2:3) to afford 6-[2-[(tert-butyldimethylsilyl)oxy]ethyl]-1-[(4-chlorophenyl)methyl]-4,7-dimethyl-2-[3-(trifluoromethoxy)phenoxy]-1H,4H,5H,6H,7H,8H-imidazo[4,5-e][1,4]diazepine-5,8-dione (220 mg, 54.95%) as a light yellow oil.

(6S)-1-[(4-chlorophenyl)methyl]-6-(2-hydroxyethyl)-4,7-dimethyl-2-[3-(trifluoromethoxy)phenoxy]-1H,4H,5H,6H,7H,8H-imidazo[4,5-e][1,4]diazepine-5,8-dione and (6R)-1-[(4-chlorophenyl)methyl]-6-(2-hydroxyethyl)-4,7-dimethyl-2-[3-(trifluoromethoxy)phenoxy]-1H,4H,5H,6H,7H,8H-imidazo[4,5-e][1,4]diazepine-5,8-dione To a stirred solution of 6-[2-[(tert-butyldimethylsilyl)oxy]ethyl]-1-[(4-chlorophenyl)methyl]-4,7-dimethyl-2-[3-(trifluoromethoxy)phenoxy]-1H,4H,5H,6H,7H,8H-imidazo[4,5-e][1,4]diazepine-5,8-dione (200 mg, 310 mmol, 1 equiv.)

in THF (10 mL) was added dropwise 6M HCl (10 mL) at room temperature. The resulting mixture was stirred at room temperature for 2 hours. The reaction mixture was basified to pH 10 with $K_2CO_3$ and extracted with ethyl acetate (3×100 mL), then the organic layer was washed with brine (2×50 mL), dried over anhydrous $Na_2SO_4$ and filtered. The filtrate was concentrated to give the crude product which was purified by prep chiral HPLC (Column: CHIRALPAK IG, 20*250 mm,5 um; Mobile Phase A: Hexane 0.1% DEA—HPLC, Mobile Phase B: EtOH—HPLC; Flow rate: 20 mL/min; Gradient: 20 B to 20 B in 18 min; 220/254 nm; RT1:10.297; RT2:13.612) to afford compound 17 (RT 10.297 min, 20.2 mg, 12.24%) and compound 18 (RT 13.612 min, 18.2 mg, 11.03%) as light yellow oils.

Compound 17 characterization: $^1$H NMR (300 MHz, DMSO-d6) δ 7.63-7.50 (m, 1H), 7.46-7.24 (m, 7H), 5.65-5.32 (m, 2H), 4.72-4.59 (m, 1H), 4.41-4.30 (m, 1H), 3.55-3.43 (m, 0.8H), 3.42-3.36 (m, 0.7H), 3.23 (s, 3H), 3.08-3.01 (m, 1H), 3.00-2.90 (m, 0.3H), 2.84 (s, 2.2H), 2.25-2.14 (m, 0.7H), 2.07-1.93 (m, 0.7H), 1.61-1.49 (m, 0.7H). [M+H]$^+$ calculated for molecular formula $C_{24}H_{22}ClF_3N_4O_5$: 539, observed: 539.

Compound 18 characterization: $^1$H NMR (300 MHz, DMSO-d6) δ 7.63-7.53 (m, 1H), 7.47-7.23 (m, 7H), 5.64-5.32 (m, 2H), 4.72-4.59 (m, 1H), 4.39-4.27 (m, 1H), 3.55-3.42 (m, 0.8H), 3.42-3.36 (m, 0.8H), 3.23 (s, 3H), 3.08-3.01 (m, 1H), 3.00-2.89 (m, 0.5H), 2.84 (s, 2.2H), 2.27-2.13 (m, 0.7H), 2.08-1.94 (m, 0.7H), 1.62-1.49 (m, 0.5H). [M+H]$^+$ calculated for molecular formula $C_{24}H_{22}ClF_3N_4O_5$: 539, observed: 539.

Preparation of Compounds 19 and 20

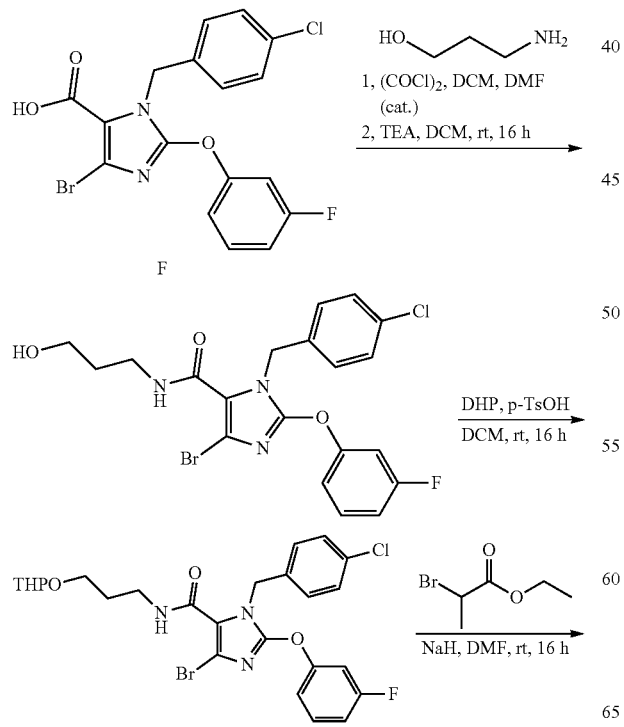

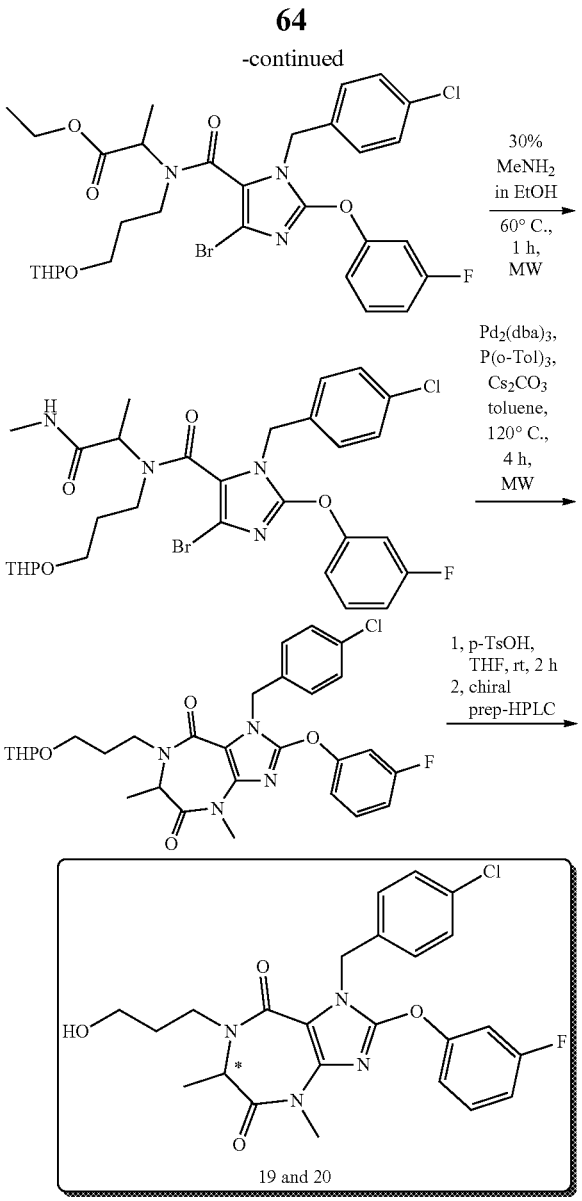

4-bromo-1-[(4-chlorophenyl)methyl]-2-(3-fluorophenoxy)-N-(3-hydroxypropyl)-1H-imidazole-5-carboxamide A mixture of 4-bromo-1-[(4-chlorophenyl)methyl]-2-(3-fluorophenoxy)-1H-imidazole-5-carboxylic acid (2 g, 4.70 mmol, 1 equiv.) and 1 drop DMF in DCM (30 mL) was added oxalic dichloride (1.8 g, 14.10 mmol, 3 equiv.) dropwise at 0° C. The mixture was stirred 3 hours at room temperature. The resulting mixture was concentrated under vacuum. The solid was dissolved with DCM (30 mL) to give solution A. A mixture of 3-aminopropan-1-ol (1.8 g, 23.49 mmol, 5 equiv.) and triethylamine (2.4 g, 23.49 mol, 5 equiv.) in DCM (5 mL) was cooled to 0° C., solution A was added dropwise at 0° C. under nitrogen atmosphere. The mixture was stirred for 3 hours at room temperature. The resulting mixture was concentrated under reduced pressure. The residue was purified by silica gel column chromatography, eluted with PE/EA (2/1 to 1/1) to afford 4-bromo-1-

[(4-chlorophenyl)methyl]-2-(3-fluorophenoxy)-N-(3-hydroxypropyl)-1H-imidazole-5-carboxamide (1.65 g, 72.74%) as a white solid.

4-bromo-1-[(4-chlorophenyl)methyl]-2-(3-fluorophenoxy)-N-[3-(oxan-2-yloxy)propyl]-1H-imidazole-5-carboxamide To a stirred mixture of 4-bromo-1-[(4-chlorophenyl)methyl]-2-(3-fluorophenoxy)-N-(3-hydroxypropyl)-1H-imidazole-5-carboxamide (1.65 g, 3.42 mmol, 1 equiv.) and 3,4-dihydro-2H-pyran (1.4427 g, 17.15 mmol, 5.018 equiv.) in DCM (50 mL) was added 4-methylbenzene-1-sulfonic acid (0.059 g, 0.34 mmol, 0.100 equiv.) at room temperature. The mixture was stirred for 16 hours at room temperature. The resulting mixture was washed with saturated NaHCO$_3$ aqueous solution. The DCM layer was concentrated under reduced pressure. The residue was purified by silica gel column chromatography, eluted with PE/EA (6/1 to 3/1) to afford 4-bromo-1-[(4-chlorophenyl)methyl]-2-(3-fluorophenoxy)-N-[3-(oxan-2-yloxy)propyl]-1H-imidazole-5-carboxamide (1.65 g, 85.16%) as a white solid.

ethyl 2-(1-[4-bromo-1-[(4-chlorophenyl)methyl]-2-(3-fluorophenoxy)-1H-imidazol-5-yl]-N-[3-(oxan-2-yloxy)propyl]formamido)propanoate To a stirred solution of 4-bromo-1-[(4-chlorophenyl)methyl]-2-(3-fluorophenoxy)-N-[3-(oxan-2-yloxy)propyl]-1H-imidazole-5-carboxamide (2.5 g, 4.41 mmol, 1 equiv.) in DMF (15 mL) was added NaH (0.7 g, 17.64 mmol, 4 equiv, 60%) in portions at 0° C. under nitrogen atmosphere. The mixture was stirred for 30 min at 0° C. and was added ethyl 2-bromopropanoate (3.1936 g, 17.64 mmol, 4.000 equiv.). The mixture was stirred for 16 hours at room temperature. The resulting mixture was quenched with water (100 mL) and extracted with EA (3×100 mL). The combined organic layers were washed with water (1×100 mL), dried over anhydrous Na$_2$SO$_4$. After filtration, the filtrate was concentrated under reduced pressure to gain crude compound. The crude product was purified by reverse phase flash with the following conditions (Column: Spherical C18 Column, 20-40 um, 120 g. Mobile Phase A: Water (0.1% AcOH), Mobile Phase B: ACN, Flow rate: 60 mL/min, Gradient:60-80% B in 35 min, 254 nm) to afford ethyl 2-(1-[4-bromo-1-[(4-chlorophenyl)methyl]-2-(3-fluorophenoxy)-1H-imidazol-5-yl]-N-[3-(oxan-2-yloxy)propyl]formamido)propanoate (1.38 g, 46.91%) as a yellow oil.

2-(1-[4-bromo-1-[(4-chlorophenyl)methyl]-2-(3-fluorophenoxy)-1H-imidazol-5-yl]-N-[3-(oxan-2-yloxy)propyl]formamido)-N-methylpropanamide Into a 20 mL vessel were added ethyl 2-(1-[4-bromo-1-[(4-chlorophenyl)methyl]-2-(3-fluorophenoxy)-1H-imidazol-5-yl]-N-[3-(oxan-2-yloxy)propyl]formamido)propanoate (1.3 g, 1 equiv.) and methylamine in methanol (6 mL, 30%) at room temperature. The mixture was reacted at 60° C. for 1 hour under Microwave condition. The resulting mixture was allowed to cool down to room temperature and concentrated under vacuum. The residue was purified by silica gel column chromatography, eluted with PE/EA (1/1) to afford 2-(1-[4-bromo-1-[(4-chlorophenyl)methyl]-2-(3-fluorophenoxy)-1H-imidazol-5-yl]-N-[3-(oxan-2-yloxy)propyl]formamido)-N-methylpropanamide (1.2 g, 94.43%) as a yellow oil.

1-[(4-chlorophenyl)methyl]-2-(3-fluorophenoxy)-4,6-dimethyl-7-[3-[(2R)-oxan-2-yloxy]propyl]-1H,4H,5H,6H,7H,8H-imidazo[4,5-e][1,4]diazepine-5,8-dione Into a 20 mL vessel were added 2-(1-[4-bromo-1-[(4-chlorophenyl)methyl]-2-(3-fluorophenoxy)-1H-imidazol-5-yl]-N-[3-(oxan-2-yloxy)propyl]formamido)-N-methylpropanamide (1.1936 g, 1.83 mol, 1 equiv.), Pd$_2$(dba)$_3$ (0.2 g, 0.18 mmol, 0.1 equiv.), Cs$_2$CO$_3$ (1.1966 g, 3.67 mmol, 2.006 equiv.), and tris(2-methylphenyl)phosphane (0.1 g, 0.37 mmol, 0.2 equiv.) at room temperature. The mixture was heated for 5 hours at 120° C. under microwave condition. The mixture was allowed to cool down to room temperature. The residue was purified by silica gel column chromatography, eluted with PE/EA (1/1) to afford 1-[(4-chlorophenyl)methyl]-2-(3-fluorophenoxy)-4,6-dimethyl-7-[3-[(2R)-oxan-2-yloxy]propyl]-1H,4H,5H,6H,7H,8H-imidazo[4,5-e][1,4]diazepine-5,8-dione (340 mg, 32.52%) as a yellow oil.

(6S)-1-[(4-chlorophenyl)methyl]-2-(3-fluorophenoxy)-7-(3-hydroxypropyl)-4,6-dimethyl-1H,4H,5H,6H,7H,8H-imidazo[4,5-e][1,4]diazepine-5,8-dione and (6R)-1-[(4-chlorophenyl)methyl]-2-(3-fluorophenoxy)-7-(3-hydroxypropyl)-4,6-dimethyl-1H,4H,5H,6H,7H,8H-imidazo[4,5-e][1,4]diazepine-5,8-dione A mixture of 1-[(4-chlorophenyl)methyl]-2-(3-fluorophenoxy)-4,6-dimethyl-7-[3-[(2R)-oxan-2-yloxy]propyl]-1H,4H,5H,6H,7H,8H-imidazo[4,5-e][1,4]diazepine-5,8-dione (200 mg, 0.35 mmol, 1 equiv.) and HCl (2M; 20 mL) in THF (20 mL) was stirred for 1 hour at room temperature. The resulting mixture was extracted with EA (3×200 mL). The combined organic layers were washed with water (1×200 mL), dried over anhydrous Na$_2$SO$_4$. After filtration, the filtrate was concentrated under reduced pressure. The crude product (170 mg) was purified by Prep-HPLC with the following conditions (Column: XBridge Prep C18 OBD Column, 5 um, 19*150 mm; Mobile Phase A: Water (0.05% TFA), Mobile Phase B: ACN; Flow rate: 20 mL/min; Gradient: 40% B to 70% B in 7 min; 254 nm; RT: 6.32 min.) to afford 1-[(4-chlorophenyl)methyl]-2-(3-fluorophenoxy)-7-(3-hydroxypropyl)-4,6-dimethyl-1H,4H,5H,6H,7H,8H-imidazo[4,5-e][1,4]diazepine-5,8-dione(140 mg). The racemate was separated by chiral HPLC with the following conditions (Column: CHIRALPAK IF, 2*25 cm, 5 um; Mobile Phase A: Hexane 0.1% DEA—HPLC, Mobile Phase B: EtOH—HPLC; Flow rate: 15 mL/min; Gradient: 50 B to 50 B in 13 min; 220/254 nm; RT1: 8.349; RT2: 9.504) to afford compound 19 (RT 8.349 min, 20 mg, 11.73%) and compound 20 (RT 9.504 min, 20 mg, 11.73%).

Compound 19 characterization: $^1$H NMR (400 MHz, Methanol-d4) δ 7.45 (dd, J=13.8, 6.2 Hz, 1H), 7.41-7.29 (m, 4H), 7.23-6.99 (m, 3H), 5.63-5.53 (m, 1H), 5.45-5.38 (m, 1H), 4.38 (dd, J=16.4, 8.3 Hz, 1H), 3.96 (dt, J=14.8, 7.7 Hz, 1H), 3.64 (t, J=7.0 Hz, 1H), 3.49 (t, J=6.3 Hz, 2H), 3.35 (s, 3H), 1.85-1.73 (m, 1H), 1.69-1.62 (dt, J=13.5, 6.9 Hz, 1H), 1.56 (d, J=7.0 Hz, 2H), 1.10 (d, J=7.5 Hz, 1H). [M+H]$^+$ calculated for molecular formula C$_{24}$H$_{24}$ClFN$_4$O$_4$: 487, observed: 487.

Compound 20 characterization: $^1$H NMR (400 MHz, Methanol-d4) δ 7.49-7.40 (m, 1H), 7.37-7.29 (m, 4H), 7.22-7.00 (m, 3H), 5.62-5.53 (m, 1H), 5.42-5.39 (m, 1H), 4.43-4.33 (m, 1H), 3.99-3.92 (dt, J=14.9, 7.7 Hz, 1H), 3.64 (t, J=8.0 Hz, 1H), 3.49 (t, J=8.0 Hz, 2H), 3.35 (s, 3H), 1.82-1.75 (m, 1H), 1.69-1.62 (dt, J=13.7, 6.9 Hz, 1H), 1.56

(d, J=8.0 Hz, 2H), 1.10 (d, J=8.0 Hz, 1H). [M+H]+ calculated for molecular formula $C_{24}H_{24}ClFN_4O_4$: 487, observed: 487.

Preparation of Compound 21

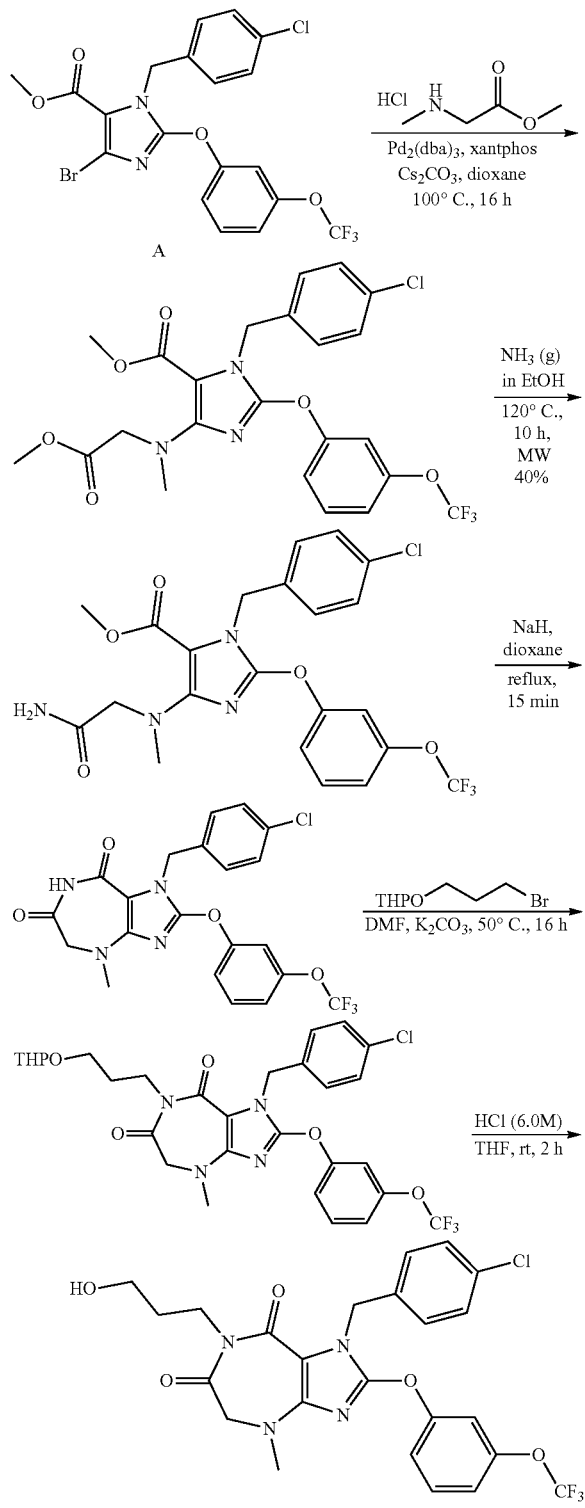

methyl 1-[(4-chlorophenyl)methyl]-4-[(2-methoxy-2-oxoethyl)(methyl)amino]-2-[3-(trifluoromethoxy)phenoxy]-1H-imidazole-5-carboxylate A mixture of methyl 4-bromo-1-[(4-chlorophenyl)methyl]-2-[3-(trifluoromethoxy)phenoxy]-1H-imidazole-5-carboxylate (1.00 g, 1.98 mol, 1 equiv.), methyl 2-(methylamino)acetate (1019.6 mg, 9.89 mol, 5.0 equiv.), $Pd_2(dba)_3$ (452.7 mg, 0.49 mmol, 0.25 equiv.), XantPhos (572.1 mg, 0.99 mmol, 0.50 equiv.) and $Cs_2CO_3$ (6.4 g, 19.78 mmol, 10.0 equiv.) in dioxane (100.0 mL) was stirred at 100° C. for 16 hours under nitrogen atmosphere. The reaction mixture was cooled to room temperature and added ethyl acetate (200 mL) and $H_2O$ (200 mL). The organic layer was washed with brine (3×50 mL), dried over anhydrous $Na_2SO_4$ and filtered. The filtrate was concentrated under reduced pressure. The residue was purified by silica gel column chromatography, eluted with PE:EtOAc (6:1 to 4:1) to afford methyl 1-[(4-chlorophenyl)methyl]-4-[(2-methoxy-2-oxoethyl)(methyl)amino]-2-[3-(trifluoromethoxy)phenoxy]-1H-imidazole-5-carboxylate (150 mg, 14.37%) as a light yellow oil.

methyl 4-[(carbamoylmethyl)(methyl)amino]-1-[(4-chlorophenyl)methyl]-2-[3-(trifluoromethoxy)phenoxy]-1H-imidazole-5-carboxylate A mixture of methyl 1-[(4-chlorophenyl)methyl]-4-[(2-methoxy-2-oxoethyl)(methyl)amino]-2-[3-(trifluoromethoxy)phenoxy]-1H-imidazole-5-carboxylate (300 mg, 570 mmol, 1 equiv.) in ammonia solution (10 mL) was irradiated with microwave radiation for 4 hours at 120° C. The reaction mixture was concentrated under reduced pressure. The residue was purified by reverse phase flash with the following conditions (Column: Spherical C18 Column, 20-40 um, 120 g; Mobile Phase A: Water (0.1% HOAc), Mobile Phase B: ACN; Flow rate: 60 mL/min; Gradient: 60% B to 70% B in 10 min, 254 nm) to afford methyl 4-[(carbamoylmethyl)(methyl)amino]-1-[(4-chlorophenyl)methyl]-2-[3-(trifluoromethoxy)phenoxy]-1H-imidazole-5-carboxylate (230 mg, 39.46%) as an off-white solid.

1-[(4-chlorophenyl)methyl]-4-methyl-2-[3-(trifluoromethoxy)phenoxy]-1H,4H,5H,6H,7H,8H-imidazo[4,5-e][1,4]diazepine-6,8-dione A mixture of methyl 4-[(carbamoylmethyl)(methyl)amino]-1-[(4-chlorophenyl)methyl]-2-[3-(trifluoromethoxy)phenoxy]-1H-imidazole-5-carboxylate (120 mg, 0.23 mmol, 1 equiv.) in dioxane (20 mL) and NaH (18.7 mg, 0.47 mmol, 2.0 equiv, 60 wt %) was refluxed for 15 min. HOAc (0.5 mL) was added to the reaction mixture and the resulting mixture was stirred at room temperature for 16 hours. The reaction mixture was concentrated under reduced pressure. The residue was purified by reverse phase flash with the following conditions (Column: Spherical C18 Column, 20-40 um, 120 g; Mobile Phase A: Water (0.1% HOAc), Mobile Phase B: ACN; Flow rate: 60 mL/min; Gradient: 60% B to 70% B in 15 min, 254 nm) to afford 1-[(4-chlorophenyl)methyl]-4-methyl-2-[3-(trifluoromethoxy)phenoxy]-1H,4H,5H,6H,7H,8H-imidazo[4,5-e][1,4]diazepine-6,8-dione (45 mg, 40.00%) as an off-white solid.

1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepine-6,8-dione A mixture of 1-[(4-chlorophenyl)methyl]-4-methyl-2-[3-(trifluoromethoxy)phenoxy]-1H,4H,5H,6H,7H,8H-imidazo

[4,5-e][1,4]diazepine-6,8-dione(100 mg, 0.21 mmol, 1 equiv.), 2-(3-bromopropoxy)oxane (139.2 mg, 0.62 mmol, 3.0 equiv.) and K$_2$CO$_3$ (86.2 mg, 0.62 mmol, 3.0 equiv.) in DMF (15.0 mL) was stirred at 50° C. for 16 hours. The reaction mixture was cooled to room temperature and was added H2O (100 mL). The resulting mixture was extracted with EtOAc (3×50 mL). The combined organic layers were washed with brine (2×50 mL), dried over anhydrous Na$_2$SO$_4$. After filtration, the filtrate was concentrated under reduced pressure under reduced pressure. The residue was purified by silica gel column chromatography, eluted with PE:EA (6:1 to 3:1) to afford 1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepine-6,8-dione (120 mg, 92.6:1%) as a light yellow oil. $^1$H NMR (400 MHz, Chloroform-d) δ 7.43 (t, J=8.3 Hz, 1H), 7.27 (d, J=8.7 Hz, 5H), 7.17 (dd, J=33.5, 8.4 Hz, 2H), 5.58 (s, 2H), 4.60 (d, J=14.8 Hz, 2H), 3.88 (s, 2H), 3.85-3.72 (m, 2H), 3.63 (dt, J=10.4, 5.6 Hz, 1H), 3.58-3.47 (m, 2H), 3.13 (s, 3H), 2.04-1.58 (m, 8H).

1-[(4-chlorophenyl)methyl]-7-(3-hydroxypropyl)-4-methyl-2-[3-(trifluoromethoxy)phenoxy]-1H,4H,5H,6H,7H,8H-imidazo[4,5-e][1,4]diazepine-6,8-dione A mixture of 1-[(4-chlorophenyl)methyl]-4-methyl-7-[3-(oxan-2-yloxy)propyl]-2-[3-(trifluoromethoxy)phenoxy]-1H,4H,5H,6H,7H,8H-imidazo[4,5-e][1,4]diazepine-6,8-dione (45 mg, 0.07 mmol, 1 equiv.) in THF (10 mL) and 6M HCl (10 mL) was stirred at room temperature for 2 hours. The reaction mixture was concentrated under reduced pressure. The residue was basified to pH 9 with sat. K$_2$CO$_3$ (aq). The resulting mixture was extracted with ethyl acetate (3×50 mL), and the combined organic layer was washed with brine (50 mL) and concentrated to give the crude product which was purified by Prep-HPLC with the following conditions (Column: XSelect CSH Prep C18 OBD Column, 5 um, 19*150 mm; Mobile Phase A: Water(0.1% FA), Mobile Phase B: ACN; Flow rate: 20 mL/min; Gradient: 50% B to 87% B in 7 min; 254 nm; RT: 6.58 min) to afford 1-[(4-chlorophenyl)methyl]-7-(3-hydroxypropyl)-4-methyl-2-[3-(trifluoromethoxy)phenoxy]-1H,4H,5H,6H,7H,8H-imidazo[4,5-e][1,4]diazepine-6,8-dione (3.9 mg, 9.52%) as an off-white solid. $^1$H NMR (400 MHz, Chloroform-d) δ 7.54-7.45 (m, 1H), 7.43-7.28 (m, 2H), 7.24-7.02 (m, 5H), 5.57 (s, 2H), 4.04 (t, J=6.0 Hz, 2H), 3.90 (s, 2H), 3.50 (t, J=5.5 Hz, 2H), 3.15 (s, 3H), 1.80 (p, J=5.7 Hz, 2H). [M+H]$^+$ calculated for molecular formula C$_{24}$H$_{22}$ClF$_3$N$_4$O$_5$: 539, observed: 539.

Preparation of Compounds 22 and 23

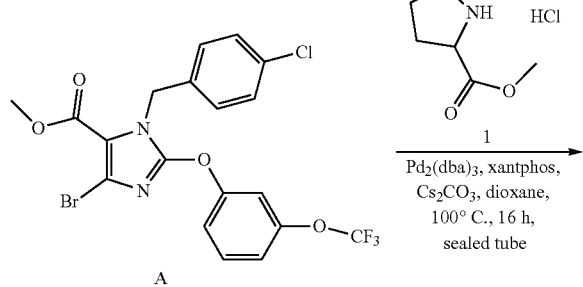

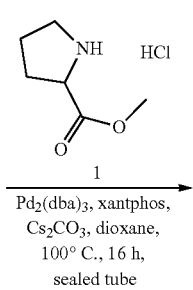

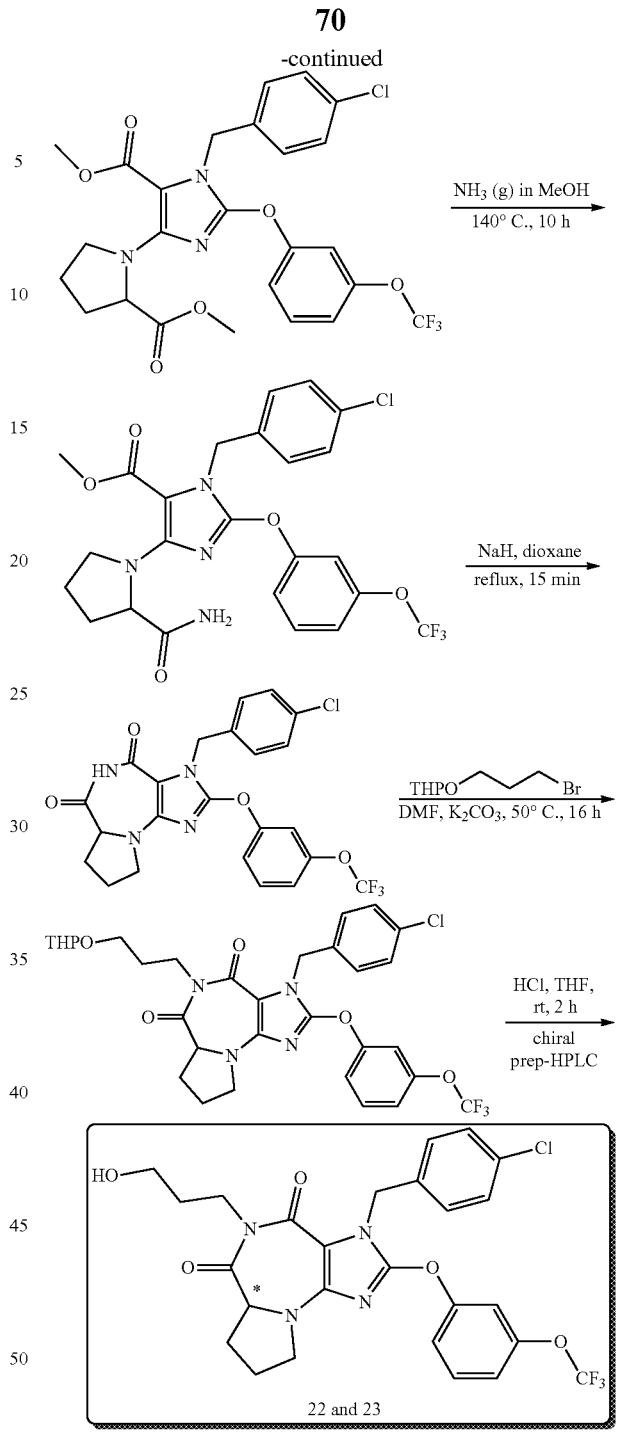

methyl 1-[(4-chlorophenyl)methyl]-4-[2-(methoxycarbonyl)pyrrolidin-1-yl]-2-[3-(trifluoromethoxy)phenoxy]-1H-imidazole-5-carboxylate A mixture of methyl 4-bromo-1-[(4-chlorophenyl)methyl]-2-[3-(trifluoromethoxy)phenoxy]-1H-imidazole-5-carboxylate (1.5 g, 2.97 mmol, 1 equiv.), Pd$_2$(dba)$_3$ (280 mg, 0.31 mmol, 0.103 equiv.), XantPhos (520 mg, 0.90 mmol, 0.303 equiv.), methyl pyrrolidine-2-carboxylate (800.0 mg, 6.19 mmol, 2.088 equiv.) and Cs$_2$CO$_3$ (4.9 g, 15.04 mmol, 5.070 equiv.) in dioxane (40 mL) was stirred at 100° C. for 14 hours. The reaction mixture was filtered and the filtrate was concentrated to give the crude product which was purified by silica gel column chromatography, eluting with PE:EA (20:1 to 4:1) to afford methyl 1-[(4-chlorophenyl)methyl]-4-[2-(methoxycarbonyl)pyrrolidin-1-yl]-2-[3-(trifluoromethoxy)phenoxy]-1H-imidazole-5-carboxylate (830 mg, 50.51%) as a light yellow oil.

methyl 4-(2-carbamoylpyrrolidin-1-yl)-1-(4-chlorobenzyl)-2-(3-(trifluoromethoxy)phenoxy)-1H-imidazole-5-carboxylate A mixture of methyl 1-[(4-chlorophenyl)methyl]-4-[2-(methoxycarbonyl)pyrrolidin-1-yl]-2-[3-(trifluoromethoxy)phenoxy]-1H-imidazole-5-carboxylate (1.65 g, 2.98 mmol, 1 equiv.) in Ammonia solution (7.0 M in methanol) (10 mL) was irradiated with microwave radiation for 10 hours at 140° C. The reaction mixture was cooled down to room temperature and concentrated to give a residue which was purified by flash chromatography on silica gel column, eluting with 70% ethyl acetate in petroleum ether to give methyl 4-(2-carbamoylpyrrolidin-1-yl)-1-(4-chlorobenzyl)-2-(3-(trifluoromethoxy)phenoxy)-1H-imidazole-5-carboxylate as a light yellow semi-solid (300 mg, 24% yield). $^1$H NMR (400 MHz, Chloroform-d) δ 7.41 (t, J=8.3 Hz, 1H), 7.34-7.24 (m, 4H), 7.23-7.18 (m, 3H), 7.12-7.07 (m, 1H), 6.52 (s, 1H), 5.41 (q, J=15.4 Hz, 2H), 4.53 (dd, J=8.2, 5.2 Hz, 1H), 3.87-3.69 (m, 4H), 3.32 (dt, J=10.5, 7.1 Hz, 1H), 2.28-2.09 (m, 2H), 2.05-1.83 (m, 2H).

5-[(4-chlorophenyl)methyl]-4-[3-(trifluoromethoxy)phenoxy]-1,3,5,8-tetraazatricyclo[8.3.0.0^[2,6]]trideca-2(6),3-diene-7,9-dione To a mixture of methyl 4-(2-carbamoylpyrrolidin-1-yl)-1-[(4-chlorophenyl)methyl]-2-[3-(trifluoromethoxy)phenoxy]-1H-imidazole-5-carboxylate (185 mg, 340 mmol, 1 equiv.) in dioxane (40 mL) was added NaH (96.1 mg, 2.40 mmol, 7.0 equiv, 60 wt %) at 0° C. and then the reaction mixture was refluxed for 15 min. The reaction mixture was cooled to room temperature and concentrated under reduced pressure. The residue product was purified by reverse phase flash with the following conditions (Column: Spherical C18 Column, 20-40 um, 120 g; Mobile Phase A: Water (0.1% HOAc), Mobile Phase B: ACN; Flow rate: 60 mL/min; Gradient: 65% B to 85% B in 15 min, 254 nm) to afford 5-[(4-chlorophenyl)methyl]-4-[3-(trifluoromethoxy)phenoxy]-1,3,5,8-tetraazatricyclo[8.3.0.0^[2,6]]trideca-2(6),3-diene-7,9-dione (115 mg, 66.09%) as an off-white solid. $^1$H NMR (400 MHz, DMSO-d6) δ 10.52 (s, 1H), 7.58 (t, J=8.3 Hz, 1H), 7.47 (d, J=2.7 Hz, 1H), 7.44-7.36 (m, 3H), 7.36-7.27 (m, 3H), 5.52 (dd, J=91.6, 15.5 Hz, 2H), 3.81 (dd, J=8.3, 5.2 Hz, 1H), 3.51 (dt, J=10.1, 7.3 Hz, 1H), 3.32 (d, J=7.1 Hz, 1H), 2.50 (s, 1H), 2.12-1.96 (m, 1H), 1.81 (qt, J=12.3, 6.6 Hz, 2H).

5-[(4-chlorophenyl)methyl]-8-[3-(oxan-2-yloxy)propyl]-4-[3-(trifluoromethoxy)phenoxy]-1,3,5,8-tetraazatricyclo[8.3.0.0^[2,6]]trideca-2(6),3-diene-7,9-dione A mixture of 5-[(4-chlorophenyl)methyl]-4-[3-(trifluoromethoxy)phenoxy]-1,3,5,8-tetraazatricyclo[8.3.0.0^[2,6]]trideca-2(6),3-diene-7,9-dione(150 mg, 300 mmol, 1 equiv.), 2-(3-bromopropoxy)oxane (198.1 mg, 890 mmol, 3.000 equiv.) and K$_2$CO$_3$ (122.7 mg, 0.89 mmol, 3.0 equiv.) in DMF (15.0 mL) was stirred at 50° C. for 16 hours. The reaction was cooled to room temperature and added EtOAc (100 mL) and H$_2$O (100 mL). The organic layer was washed with brine (2×30 mL) and concentrated under reduced pressure which was purified by reverse phase flash with the following conditions (Column: Spherical C18 Column, 20-40 um, 120 g; Mobile Phase A: Water (0.1% HOAc), Mobile Phase B: ACN; Flow rate: 60 mL/min; Gradient: 90% B to 98% B in 10 min, 254 nm) to afford 5-[(4-chlorophenyl)methyl]-8-[3-(oxan-2-yloxy)propyl]-4-[3-(trifluoromethoxy)phenoxy]-1,3,5,8-tetraazatricyclo[8.3.0.0^[2,6]]trideca-2(6),3-diene-7,9-dione (185 mg, 96.31%) as a light yellow oil. $^1$H NMR (400 MHz, Chloroform-d) δ 7.43 (t, J=8.3 Hz, 1H), 7.30 (s, 4H), 7.27-7.19 (m, 2H), 7.13 (d, J=8.3 Hz, 1H), 5.73 (d, J=14.9 Hz, 1H), 5.43 (d, J=15.1 Hz, 1H), 4.65-4.49 (m, 1H), 4.15 (ddt, J=19.0, 13.7, 7.1 Hz, 1H), 3.98-3.61 (m, 4H), 3.46 (tt, J=16.5, 7.6 Hz, 4H), 2.85 (dt, J=12.2, 6.3 Hz, 1H), 2.18-2.02 (m, 2H), 1.99-1.77 (m, 3H), 1.76-1.48 (m, 6H).

(10R)-5-[(4-chlorophenyl)methyl]-8-(3-hydroxypropyl)-4-[3-(trifluoromethoxy)phenoxy]-1,3,5,8-tetraazatricyclo[8.3.0.0^[2,6]]trideca-2(6),3-diene-7,9-dione and (10S)-5-[(4-chlorophenyl)methyl]-8-(3-hydroxypropyl)-4-[3-(trifluoromethoxy)phenoxy]-1,3,5,8-tetraazatricyclo[8.3.0.0^[2,6]]trideca-2(6),3-diene-7,9-dione A mixture of 5-[(4-chlorophenyl)methyl]-8-[3-(oxan-2-yloxy)propyl]-4-[3-(trifluoromethoxy)phenoxy]-1,3,5,8-tetraazatricyclo[8.3.0.0^[2,6]]trideca-2(6),3-diene-7,9-dione (160 mg, 250 mmol, 1 equiv.) in THF (5 mL) and 2 M HCl (5 mL) was stirred at room temperature for 2 hours. To the reaction mixture was added sat NaHCO$_3$(aq) to adjust pH to 9 and EtOAc (100 mL), then the organic layer was washed with brine (2×50 mL) and concentrated under reduced pressure. The residue was purified by Prep-HPLC with the following conditions (Column: XBridge Shield RP18 OBD Column 30*150 mm, 5 um; Mobile Phase A: Water(0.1% FA), Mobile Phase B: ACN; Flow rate: 60 mL/min; Gradient: 50% B to 80% B in 7 min; 254 nm; RT: 6.45 min) to afford racemic 5-[(4-chlorophenyl)methyl]-8-(3-hydroxypropyl)-4-[3-(trifluoromethoxy)phenoxy]-1,3,5,8-tetraazatricyclo[8.3.0.0^[2,6]]trideca-2(6),3-diene-7,9-dione(110 mg, 78.99%) as a colorless oil. 90 mg of this material was then submitted for chiral prep-HPLC (Column: CHIRALPAK AD-H, 2.0 cm I.D.*25 cm L; Mobile Phase A: Hexane 0.1% DEA—HPLC, Mobile Phase B: EtOH—HPLC; Flow rate: 20 mL/min; Gradient: 15 B to 15 B in 15 min; 220/254 nm; RT1:9.279; RT2:10.54) to afford compound 22 (RT 9.279 min, 17.7 mg, 19.67%) and compound 23 (RT 10.54 min, 19.11%).

Compound 22 characterization: $^1$H NMR (400 MHz, Methanol-d4) δ 7.55-7.51 (m, 1H), 7.36-7.27 (m, 6H), 7.23-7.20 (m, 1H), 5.70 (d, J=16.0 Hz, 1H), 5.52 (d, J=16.0 Hz, 11H), 4.13-4.05 (m, 1H), 3.90-3.83 (m, 1H), 3.75-3.73 (m, 1H), 3.69-3.62 (m, 1H), 3.58-3.51 (m, 2H), 3.45-3.41 (m, 1H), 2.80-2.72 (m, 1H), 2.19-2.10 (m, 11H), 2.05-1.92 (m, 2H), 1.91-1.68 (m, 2H). [M+H]$^+$ calculated for molecular formula C$_{26}$H$_{24}$ClF$_3$N$_4$O$_5$: 565, observed: 565

Compound 23 characterization: ¹H NMR (400 MHz, Methanol-d4) δ 7.55-7.51 (m, 1H), 7.35-7.28 (m, 6H), 7.23-7.21 (m, 1H), 5.70 (d, J=16.0 Hz, 1H), 5.52 (d, J=16.0 Hz, 1H), 4.13-4.06 (m, 11H), 3.90-3.82 (m, 1H), 3.77-3.73 (m, 1H), 3.69-3.62 (m, 1H), 3.55-3.51 (m, 2H), 3.46-3.41 (m, 11H), 2.79-2.70 (m, 1H), 2.19-2.10 (m, 1H), 2.04-1.94 (m, 2H), 1.79-1.70 (m, 2H). [M+H]⁺ calculated for molecular formula $C_{26}H_{24}ClF_3N_4O_5$: 565, observed: 565.

Preparation of Compounds 24 and 25

Preparation of the racemate of compounds 24 and 25 follows the methods and protocols as described for the synthesis of compounds 22 and 23, starting from intermediate I.

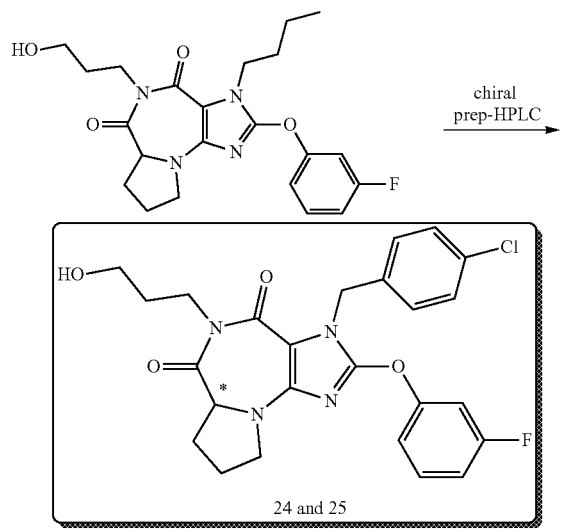

24 and 25

(10R)-5-butyl-4-(3-fluorophenoxy)-8-(3-hydroxypropyl)-1,3,5,8-tetraazatricyclo[8.3.0.0^[2,6]]trideca-2(6),3-diene-7,9-dione and (10S)-5-butyl-4-(3-fluorophenoxy)-8-(3-hydroxypropyl)-1,3,5,8-tetraazatricyclo[8.3.0.0^[2,6]]trideca-2(6),3-diene-7,9-dione Crude 5-butyl-4-(3-fluorophenoxy)-8-(3-hydroxypropyl)-1,3,5,8-tetraazatricyclo[8.3.0.0^[2,6]]trideca-2(6),3-diene-7,9-dione was purified by chiral HPLC (Column: XBridge Shield RP18 OBD Column, 5 um, 19*150 mm; Mobile Phase A: Water(10 MMOL/L NH₄HCO₃), Mobile Phase B: ACN; Flow rate: 20 mL/min; Gradient: 45% B to 70% B in 7 min; 220 nm; RT1: 15.00 min, RT2: 17.33 min) to afford compound 24 (RT=15.00 min, 20.3 mg, 8.09%) and compound 25 (RT=17.33 min, 18.9 mg, 7.53%).

Compound 24 characterization: ¹H NMR (400 MHz, Methanol-d4) δ 7.51-7.40 (m, 1H), 7.19-7.08 (m, 2H), 7.09-6.99 (m, 1H), 4.41 (dt, J=13.5, 6.8 Hz, 1H), 4.26 (dt, J=13.7, 7.4 Hz, 1H), 4.13 (ddd, J=13.4, 7.7, 5.8 Hz, 1H), 3.88 (dt, J=13.6, 7.3 Hz, 11H), 3.75 (dd, J=8.2, 4.7 Hz, 11H), 3.70-3.50 (m, 3H), 3.42 (dd, J=10.7, 5.8 Hz, 1H), 2.77 (dq, J=12.2, 6.0 Hz, 1H), 2.16 (dq, J=12.7, 7.8 Hz, 1H), 1.98 (h, J=6.1 Hz, 2H), 1.79 (dq, J=14.5, 7.1 Hz, 4H), 1.38 (p, J=7.4 Hz, 2H), 0.98 (t, J=7.4 Hz, 3H). [M+H]⁺ calculated for molecular formula $C_{22}H_{27}FN_4O_4$: 431, observed: 431.

Compound 25 characterization: ¹H NMR (400 MHz, Methanol-d4) δ 7.49-7.38 (m, 1H), 7.19-7.10 (m, 2H), 7.03 (d, J=7.8 Hz, 11H), 4.41 (dt, J=13.6, 6.8 Hz, 11H), 4.26 (dt, J=13.9, 7.4 Hz, 11H), 4.17-4.08 (m, 11H), 3.88 (dt, J=13.5, 7.2 Hz, 11H), 3.75 (dd, J=8.2, 4.7 Hz, 11H), 3.70-3.52 (m, 3H), 3.43 (dt, J=11.0, 5.8 Hz, 1H), 2.77 (dq, J=12.3, 6.1 Hz, 1H), 2.16 (dq, J=12.6, 7.8 Hz, 1H), 1.99 (hept, J=6.1 Hz, 2H), 1.80 (dp, J=14.6, 7.1 Hz, 4H), 1.35 (dd, J=17.2, 9.9 Hz, 2H), 0.98 (t, J=7.4 Hz, 3H). [M+H]⁺ calculated for molecular formula $C_{22}H_{27}FN_4O_4$: 431, observed: 431.

The following compounds were prepared by procedures analogous to those for preparation of compounds 22 and 23.

| Compound | Starting Material | NMR | LCMS |
|---|---|---|---|
| 26 | J | ¹H NMR (400 MHz, Methanol-d4) chemical shifts 7.44 (q, J = 7.8 Hz, 1H), 7.38-7.28 (m, 4H), 7.18-7.01 (m, 3H), 5.69 (d, J = 15.4 Hz, 1H), 5.50 (d, J = 15.4 Hz, 1H), 4.10 (dt, J = 13.3, 6.8 Hz, 1H), 3.87 (dt, J = 13.7, 7.3 Hz, 1H), 3.75 (dd, J = 8.2, 4.9 Hz, 1H), 3.67 (q, J = 7.8 Hz, 1H), 3.53 (t, J = 6.6 Hz, 2H), 3.44 (dt, J = 11.1, 6.0 Hz, 1H), 2.76 (dq, J = 12.1, 6.2 Hz, 1H), 2.15 (dd, J = 13.2, 7.4 Hz, 1H), 1.99 (dp, J = 12.8, 6.2 Hz, 2H), 1.85-1.65 (m, J = 6.8 Hz, 2H). | [M + H]⁺ calculated for molecular formula $C_{25}H_{24}ClFN_4O_4$: 499, observed: 499 |
| 27 | J | ¹H NMR (400 MHz, Methanol-d4) chemical shifts 7.44 (q, J = 7.8 Hz, 1H), 7.37-7.30 (m, 4H), 7.18-7.01 (m, 3H), 5.69 (d, J = 15.3 Hz, 1H), 5.50 (d, J = 15.4 Hz, 1H), 4.10 (dt, J = 13.4, 6.8 Hz, 1H), 3.86 (dt, J = 13.8, 7.3 Hz, 1H), 3.75 (dd, J = 8.2, 5.0 Hz, 1H), 3.67 (q, J = 7.6 Hz, 1H), 3.53 (t, J = 6.5 Hz, 2H), 3.44 (dt, J = 10.9, 5.9 Hz, 1H), 2.76 (dq, J = 12.2, 6.0 Hz, 1H), 2.15 (dq, J = 15.1, 7.8 Hz, 1H), 2.00 (tq, J = 12.9, 6.7, 6.3 Hz, 2H), 1.86-1.66 (m, J = 6.7 Hz, 2H). | [M + H]⁺ calculated for molecular formula $C_{25}H_{24}ClFN_4O_4$: 499, observed: 499 |
| 28 | K | ¹H NMR (400 MHz, Methanol-d4) chemical shifts 7.31 (d, J = 8.1 Hz, 2H), 7.23 (d, J = 8.2 Hz, 2H), 5.47 (d, J = 15.2 Hz, 1H), 5.26 (td, J = 13.6, 12.5, 7.1 Hz, 2H), 4.06 (dt, J = 13.4, 6.8 Hz, 1H), 3.93-3.75 (m, 2H), 3.71-3.64 (m, 1H), 3.50 (q, J = 5.6, 5.1 Hz, 3H), 2.76 (dq, J = 12.1, 6.0 Hz, 1H), 2.15 (dq, J = 14.6, 7.6 Hz, 1H), 2.01 (dp, J = 13.2, 6.1 Hz, 2H), 1.82-1.61 (m, J = 6.7 Hz, 2H), 1.47-1.25 (m, 6H). | [M + H]⁺ calculated for molecular formula $C_{22}H_{27}ClN_4O_4$: 447, observed: 447 |
| 29 | K | ¹H NMR (400 MHz, Methanol-d4) chemical shifts 7.31 (d, J = 8.1 Hz, 2H), 7.23 (d, J = 8.2 Hz, 2H), 5.47 (d, J = 15.2 Hz, 1H), 5.26 (td, J = 13.6, 7.2 Hz, 2H), | [M + H]⁺ calculated for molecular |

-continued

| Compound | Starting Material | NMR | LCMS |
|---|---|---|---|
|  |  | 4.06 (dt, J = 13.3, 6.8 Hz, 1H), 3.93-3.74 (m, 2H), 3.70 (dd, J = 8.1, 5.0 Hz, 1H), 3.50 (t, J = 6.2 Hz, 3H), 2.76 (dd, J = 12.6, 6.2 Hz, 1H), 2.15 (dq, J = 14.6, 7.6 Hz, 1H), 2.01 (dq, J = 13.3, 6.4 Hz, 2H), 1.73 (dp, J = 14.2, 6.8 Hz, 2H), 1.39 (dd, J = 6.3, 2.0 Hz, 6H). | formula $C_{22}H_{27}ClN_4O_4$: 447, observed: 447 |
| 30 | L | $^1$H NMR (400 MHz, Methanol-d4) chemical shifts 7.32 (d, J = 8.2 Hz, 2H), 7.23 (d, J = 8.2 Hz, 2H), 5.50 (d, J = 15.4 Hz, 1H), 5.32 (d, J = 15.3 Hz, 1H), 4.43 (t, J = 6.5 Hz, 2H), 4.06 (dt, J = 13.4, 6.7 Hz, 1H), 3.90-3.75 (m, 2H), 3.71 (dd, J = 8.2, 5.0 Hz, 1H), 3.51 (q, J = 6.9 Hz, 3H), 2.76 (dd, J = 12.4, 6.3 Hz, 1H), 2.15 (dq, J = 14.5, 7.5 Hz, 1H), 2.01 (dq, J = 13.3, 6.3 Hz, 2H), 1.76 (m, 4H), 0.99 (t, J = 7.4 Hz, 3H). | [M + H]$^+$ calculated for molecular formula $C_{22}H_{27}ClN_4O_4$: 447, observed: 447 |
| 31 | L | $^1$H NMR (400 MHz, Methanol-d4) chemical shifts 7.32 (d, J = 8.0 Hz, 2H), 7.23 (d, J = 8.1 Hz, 2H), 5.50 (d, J = 15.3 Hz, 1H), 5.32 (d, J = 15.2 Hz, 1H), 4.43 (t, J = 6.5 Hz, 2H), 4.06 (dt, J = 13.4, 6.9 Hz, 1H), 3.91-3.74 (m, 2H), 3.72-3.67 (m, 1H), 3.50 (t, J = 6.9 Hz, 3H), 2.76 (dd, J = 12.5, 6.3 Hz, 1H), 2.14 (dt, J = 14.9, 7.6 Hz, 1H), 2.00 (dt, J = 13.3, 6.9 Hz, 2H), 1.76 (m, 4H), 0.99 (t, J = 7.4 Hz, 3H). | [M + H]$^+$ calculated for molecular formula $C_{22}H_{27}ClN_4O_4$: 447, observed: 447 |
| 32 | M | $^1$H NMR (400 MHz, Methanol-d4) chemical shifts 7.44 (t, J = 8.2 Hz, 1H), 7.38 (d, J = 2.2 Hz, 1H), 7.32-7.28 (m, 1H), 7.24 (dd, J = 8.3, 2.4 Hz, 1H), 4.42 (dt, J = 13.5, 6.8 Hz, 1H), 4.26 (dt, J = 13.9, 7.4 Hz, 1H), 4.13 (ddd, J = 13.4, 7.7, 5.8 Hz, 1H), 3.88 (dt, J = 13.6, 7.3 Hz, 1H), 3.76 (dd, J = 8.2, 4.7 Hz, 1H), 3.64 (dt, J = 10.2, 7.4 Hz, 1H), 3.59-3.51 (m, 2H), 3.43 (dt, J = 10.8, 5.7 Hz, 1H), 2.77 (dq, J = 12.1, 5.9 Hz, 1H), 2.15 (dt, J = 12.9, 7.9 Hz, 1H), 1.98 (dp, J = 12.1, 6.4, 5.6 Hz, 2H), 1.86-1.70 (m, 4H), 1.40 (h, J = 7.3 Hz, 2H), 0.99 (t, J = 7.4 Hz, 3H). | [M + H] calculated for molecular formula $C_{22}H_{27}ClN_4O_4$: 447, observed: 447 |
| 33 | N | $^1$H NMR (400 MHz, Methanol-d4) chemical shifts 7.42 (t, J = 8.2 Hz, 1H), 7.37-7.30 (m, 6H), 7.25-7.18 (m, 1H), 5.70 (d, J = 15.3 Hz, 1H), 5.50 (d, J = 15.3 Hz, 1H), 4.10 (dt, J = 13.4, 6.4 Hz, 1H), 3.86 (dt, J = 13.7, 7.3 Hz, 1H), 3.75 (dd, J = 8.1, 4.9 Hz, 1H), 3.70-3.58 (m, 1H), 3.58-3.49 (m, 2H), 3.44 (dt, J = 10.9, 6.0 Hz, 1H), 2.76 (dq, J = 12.1, 5.9 Hz, 1H), 2.19-2.09 (m, 1H), 2.00 (tq, J = 12.7, 6.6, 6.2 Hz, 2H), 1.76 (dp, J = 14.3, 7.0 Hz, 2H). | [M + H]$^+$ calculated for molecular formula $C_{25}H_{24}Cl_2N_4O_4$: 515, observed: 515 |

Preparation of Compounds 34 and 35

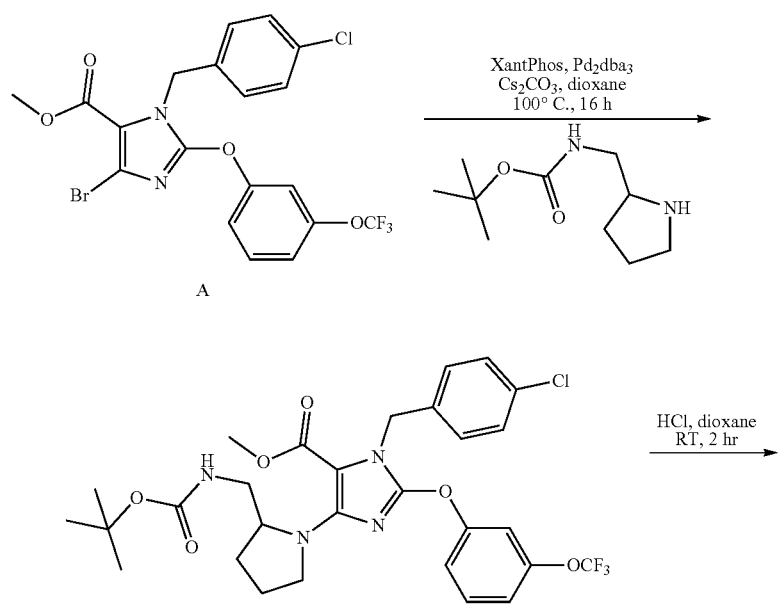

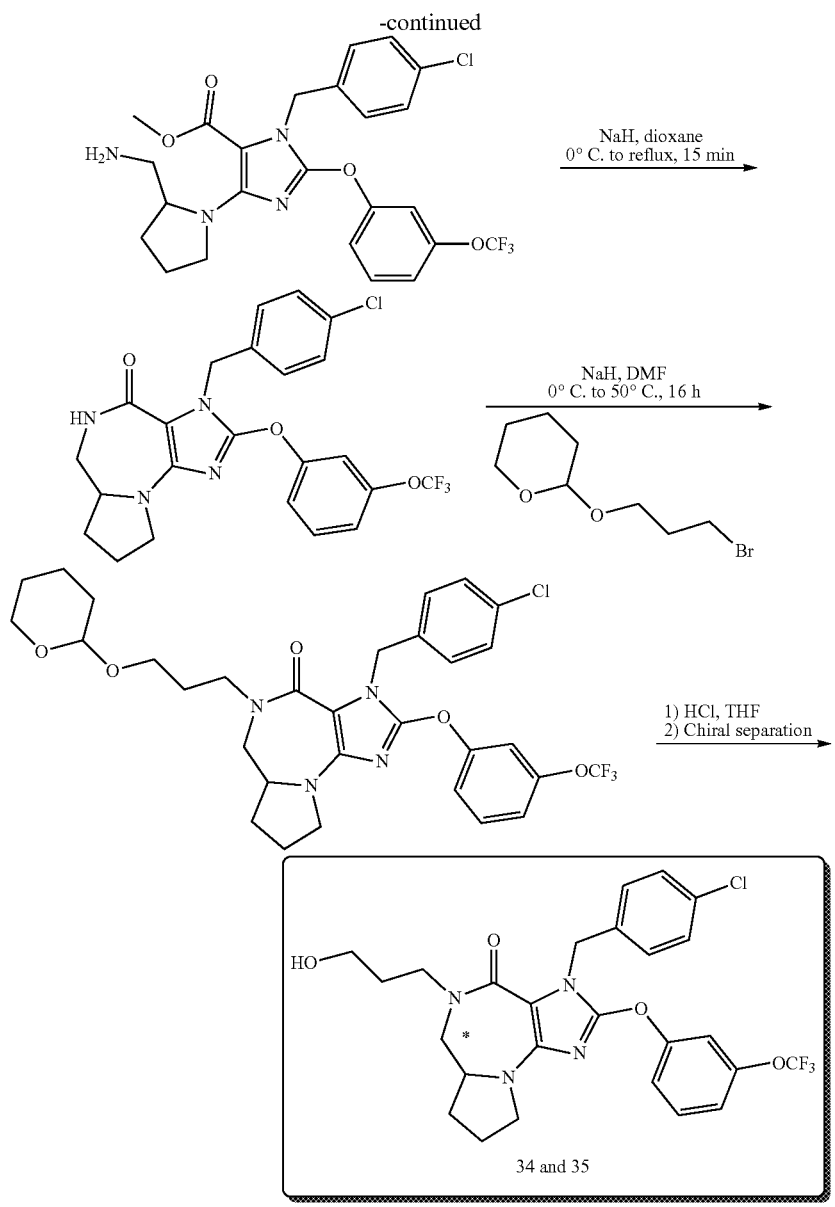

methyl 4-[2-([[(tert-butoxy)carbonyl]amino]methyl)pyrrolidin-1-yl]-1-[(4-chlorophenyl)methyl]-2-[3-(trifluoromethoxy)phenoxy]-1H-imidazole-5-carboxylate A mixture of methyl 4-bromo-1-[(4-chlorophenyl)methyl]-2-[3-(trifluoromethoxy)phenoxy]-1H-imidazole-5-carboxylate (Intermediate A, 6 g, 11.87 mmol, 1 equiv.), tert-butyl N-[(pyrrolidin-2-yl)methyl]carbamate (4.8 g, 23.73 mmol, 2.00 equiv.), XantPhos (2.1 g, 3.56 mmol, 0.3 equiv.), Pd$_2$(dba)$_3$ (1.1 g, 1.19 mmol, 0.1 equiv.) and Cs$_2$CO$_3$ (19.3 g, 59.33 mmol, 5 equiv.) in dioxane (100 mL) was stirred at 100 degrees C. for 16 h. The reaction mixture was filtered and the filtrate was concentrated to give the crude product which was purified by silica gel column chromatography, eluted with PE:EA (20:1 to 1:1) to afford methyl 4-[2-([[(tert-butoxy)carbonyl]amino]methyl)pyrrolidin-1-yl]-1-[(4-chlorophenyl)methyl]-2-[3-(trifluoromethoxy)phenoxy]-1H-imidazole-5-carboxylate (3.4 g, 45.84%) as light a yellow oil. $^1$H NMR (400 MHz, Chloroform-d) δ 7.42 (t, J=8.2 Hz, 1H), 7.31 (d, J=8.2 Hz, 2H), 7.23 (q, J=9.0, 8.4 Hz, 4H), 7.10 (d, J=8.3 Hz, 1H), 5.45 (d, J=15.8 Hz, 1H), 5.33 (d, J=15.4 Hz, 11H), 5.02 (s, 1H), 4.16 (dt, J=23.2, 6.8 Hz, 1H), 3.76 (s, 4H), 3.30 (s, 2H), 3.11 (s, 1H), 1.97 (d, J=41.7 Hz, 2H), 1.75 (d, J=6.8 Hz, 2H), 1.43 (s, 9H).

methyl 4-[2-(aminomethyl)pyrrolidin-1-yl]-1-[(4-chlorophenyl)methyl]-2-[3-(trifluoromethoxy)phenoxy]-1H-imidazole-5-carboxylate To a stirred solution of methyl 4-[2-([[(tert-butoxy)carbonyl]amino]methyl)pyrrolidin-1-yl]-1-[(4-chlorophenyl)methyl]-2-[3-(trifluoromethoxy)phenoxy]-1H-imidazole-5-carboxylate (3.4 g, 5.44 mmol, 1 equiv.) in HCl (4M) (30 mL, 987.36 mmol, 181.51 equiv.) was stirred at room temperature for 2 hours. The reaction mixture was basified to pH 10 with K$_2$CO$_3$ and extracted with ethyl acetate (5×150 mL), then the organic layer was washed with brine (2×150 mL), dried over anhydrous $Na_2SO_4$ and filtered. The filtrate was concentrated to afford methyl 4-[2-(aminomethyl)pyrrolidin-1-yl]-1-[(4-chlorophenyl)methyl]-2-[3-(trifluoromethoxy)phenoxy]-1H-imidazole-5-carboxylate (2.85 g, crude) as a light yellow oil. $^1$H NMR (400 MHz, Chloroform-d) δ 7.39 (t, J=8.3 Hz, 1H), 7.34-7.28 (m, 3H), 7.19 (t, J=7.6 Hz, 3H), 7.07 (d, J=8.3 Hz, 1H), 5.44 (d, J=15.5 Hz, 1H), 5.32 (d, J=15.4 Hz, 1H), 4.25-4.08 (m, 2H), 3.92-3.66 (m, 5H), 3.11 (ddd, J=10.9, 6.8, 3.2 Hz, 1H), 2.81 (d, J=4.9 Hz, 2H), 2.04-1.86 (m, 2H), 1.75 (td, J=12.2, 7.8 Hz, 2H).

5-[(4-chlorophenyl)methyl]-4-[3-(trifluoromethoxy)phenoxy]-1,3,5,8-tetraazatricyclo [8.3.0.0^[2,6]] trideca-2(6),3-dien-7-one To a mixture of methyl 4-[2-(aminomethyl)pyrrolidin-1-yl]-1-[(4-chlorophenyl)methyl]-2-[3-(trifluoromethoxy)phenoxy]-1H-imidazole-5-carboxylate (2.75 g, 5.24 mmol, 1 equiv.) in dioxane (50 mL) was added NaH (1.5 g, 36.67 mmol, 7.00 equiv., 60%) at 0 degrees C. and then the reaction mixture was refluxed for 15 min. The reaction mixture was cooled to room temperature and concentrated to give the residue. The residue product was purified by silica gel column chromatography, eluted with PE:EA (1:2 to 0:1) to afford 5-[(4-chlorophenyl)methyl]-4-[3-(trifluoromethoxy)phenoxy]-1,3,5,8-tetraazatricyclo[8.3.0.0^[2,6]] trideca-2(6),3-dien-7-one (1.5 g, 58.09%) as a white solid. $^1$H NMR (400 MHz, Chloroform-d) δ 7.38 (t, J=8.3 Hz, 1H), 7.26 (s, 5H), 7.18 (dd, J=8.4, 2.3 Hz, 1H), 7.06 (d, J=8.3 Hz, 1H), 5.67 (d, J=14.9 Hz, 2H), 5.40 (d, J=14.9 Hz, 1H), 3.68-3.38 (m, 4H), 3.22-3.09 (m, 1H), 2.18 (dt, J=12.8, 6.4 Hz, 1H), 1.93 (tdd, J=21.4, 11.8, 6.7 Hz, 2H), 1.61 (qd, J=11.5, 7.9 Hz, 1H), 5-[(4-chlorophenyl)methyl]-8-[3-(oxan-2-yloxy)propyl]-4-[3-(trifluoromethoxy)phenoxy]-1,3,5,8-tetraazatricyclo[8.3.0.0^[2,6]]trideca-2(6),3-dien-7-one To a mixture of 5-[(4-chlorophenyl)methyl]-4-[3-(trifluoromethoxy)phenoxy]-1,3,5,8-tetraazatricyclo[8.3.0.0^[2,6]] trideca-2(6),3-dien-7-one (350 mg, 0.71 mmol, 1 equiv.) in DMF (40 mL) was added NaH (85.2 mg, 2.13 mmol, 3 equiv., 60%) at 0 degrees C. under nitrogen atmosphere for 0.5 h. To the above mixture was added 2-(3-bromopropoxy)oxane (475.3 mg, 2.13 mmol, 3.00 equiv.) at 0 degrees C. The resulting mixture was stirred for additional 16 h at 50 degrees C. The resulting mixture was added ethyl acetate (300 mL) and brine (100 mL), then the water layer was extracted with ethyl acetate (200 mL). The combined organic layer was dried over anhydrous $Na_2SO_4$ and filtered. The filtrate was concentrated to give the crude product which was purified by silica gel column chromatography, eluted with PE:EA (10:1 to 1:1) to afford 5-[(4-chlorophenyl)methyl]-8-[3-(oxan-2-yloxy)propyl]-4-[3-(trifluoromethoxy)phenoxy]-1,3,5,8-tetraazatricyclo[8.3.0.0^[2,6]] trideca-2(6),3-dien-7-one (300 mg, 66.52%) as a light yellow oil.

(10R)-5-[(4-chlorophenyl)methyl]-8-(3-hydroxypropyl)-4-[3-(trifluoromethoxy)phenoxy]-1,3,5,8-tetraazatricyclo[8.3.0.0^[2,6]]trideca-2(6),3-dien-7-one and (10S)-5-[(4-chlorophenyl)methyl]-8-(3-hydroxypropyl)-4-[3-(trifluoromethoxy)phenoxy]-1,3,5,8-tetraazatricyclo[8.3.0.0^[2,6]]trideca-2(6),3-dien-7-one To a stirred solution of 5-[(4-chlorophenyl)methyl]-8-[3-(oxan-2-yloxy)propyl]-4-[3-(trifluoromethoxy)phenoxy]-1,3,5,8-tetraazatricyclo[8.3.0.0^[2,6]]trideca-2(6),3-dien-7-one (300 mg, 0.47 mmol, 1 equiv.) in THF (15 mL) was added dropwise HCl (2M) (15 mL) at room temperature. Then the resulting mixture was stirred at room temperature for 2 hours. The reaction mixture was basified to pH 10 with $K_2CO_3$ and extracted with ethyl acetate (3×100 mL), then the organic layer was washed with brine (2×50 mL), dried over anhydrous $Na_2SO_4$ and filtered. The filtrate was concentrated to give the crude product which was purified by prep chiral HPLC (Column: (R,R)Whelk-01, 21.1*250 mm, 5 um; Mobile Phase A: Hex—HPLC, Mobile Phase B: EtOH—HPLC; Flow rate: 20 mL/min; Gradient: 50 B to 50 B in 14 min; 220/254 nm; RT1:8.638; RT2:11.063) to afford compound 34 (37.8 mg, 14.52%) and compound 35 (51.9 mg, 19.94%).

Compound 34 characterization: $^1$H NMR (400 MHz, Methanol-d4) chemical shifts 7.49 (t, J=8.2 Hz, 1H), 7.29 (d, J=8.2 Hz, 2H), 7.26-7.18 (m, 4H), 7.15 (d, J=8.3 Hz, 1H), 5.64 (d, J=15.3 Hz, 1H), 5.34 (d, J=15.3 Hz, 1H), 3.80 (dt, J=14.3, 7.4 Hz, 1H), 3.65-3.38 (m, 6H), 3.25 (dd, J=13.4, 6.5 Hz, 1H), 3.15 (dd, J=14.8, 7.6 Hz, 1H), 2.24 (dt, J=12.0, 6.0 Hz, 1H), 2.02-1.85 (m, 2H), 1.76 (p, J=6.5 Hz, 2H), 1.69-1.56 (m, 1H). [M+H]$^+$ calculated for molecular formula $C_{26}H_{26}ClF_3N_4O_4$: 551, observed: 551.

Compound 35 characterization: $^1$H NMR (400 MHz, Methanol-d4) chemical shifts 7.49 (t, J=8.2 Hz, 11H), 7.29 (d, J=8.3 Hz, 2H), 7.26-7.18 (m, 4H), 7.15 (d, J=8.3 Hz, 1H), 5.64 (d, J=15.2 Hz, 1H), 5.34 (d, J=15.3 Hz, 11H), 3.80 (dt, J=14.3, 7.4 Hz, 1H), 3.66-3.38 (m, 6H), 3.25 (dd, J=13.5, 6.4 Hz, 1H), 3.15 (dd, J=14.8, 7.6 Hz, 1H), 2.24 (dt, J=12.3, 6.2 Hz, 11H), 2.11-1.85 (m, 2H), 1.76 (p, J=6.4 Hz, 2H), 1.70-1.58 (m, 1H). [M+H]$^+$ calculated for molecular formula $C_{26}H_{26}ClF_3N_4O_4$: 551, observed: 551.

Example 2: Assay Protocols

I. Human TRPC5 Expressing Cells.

ICLN-1633 cells (HEK-TREx hTRPC5) expressing TRPC5 were generated as follows. Commercially available HekTrex-293 cells were seeded at 0.7×106 cells/well in a 1×6-well plate 24 hrs prior to transfection using 2 mL cell growth media containing no antibiotics (1×DMEM/high glucose (Hyclone #SH30022.02); 10% fetal bovine serum (Sigma) 2 mM sodium pyruvate, 10 mM HEPES). The human TRPC5 coding sequence (NM_012471 with a silent T478C mutation) was cloned into pcDNA5/TO (Invitrogen; Cat No. V103320) using hygromycin as the resistance gene and the plasmid (SEQ ID NO: 1) propagated using T-Rex-293 cells (Invitrogen; Cat No. R71007) following manufacturer's directions. On day 2, 2 μg of plasmid DNA plus 6 μl of Xtreme-GENE HP reagent in Optimem (200 μl total volume) was prepared and incubated for 15 min at room temperature. This plasmid solution was then gently overlayed dropwise onto each well and the plate was gently swirled to mix complex with the media for approximately 30 seconds. Transfected cells were incubated at 37° C. in a 10% $CO_2$ incubator for 24 hrs. The transfected cells were harvested and transferred into 2×150 mm dishes containing cell growth media with no antibiotics at 37° C.

The next day selection was initiated to generate a stable pool by adding cell growth media containing 150 μg/mL Hygromycin and 5 μg/mL Blasticidin and cells were allowed to grow. Media with the selection agent was changed every 1-2 days as needed to remove dead cells. After 7 days, the hygromycin concentration was reduced to 75 μg/mL and cells growth was allowed to continue.

Single clones were selected as follows. The stable pool was diluted to 10 cells/mL and seeded (100 μl/well) into 24×96 well plates (~1 cell/well) and allowed to grow for 7 days in cell growth media. Fresh media (100 μl) was added and the cells allowed to grow for another 1-2 weeks and then stored frozen or used immediately.

II. Automated Patch Clamp Assay (Qpatch)

The automated electrophysiological assay was carried out at room temperature. On the day of the experiment, TRPC5 cells were cultured according to our Standard Operating Procedure. Briefly, cells were harvested using TrypLE™ Express, re-suspended in serum free medium, added to the automated platform and used within 0.5-3 hours. Internal and external physiological solutions were freshly prepared prior to the assay. The external solution contained: 145 mM NaCl, 4 mM KCl, 2 mM $CaCl_2$, 1 mM $MgCl_2$, 10 mM HEPES, 10 mM glucose, pH 7.4 with NaOH and 310 mOsm/L. The internal solution contained 120 mM L-aspartic acid, 120 mM $CsOH.H_2O$, 20 mM CsCl, 2 mM $MgCl_2$, 8.8 mM $CaCl_2$, 10 mM EGTA, 10 mM HEPES and 2 mM $Na_2ATP$; pH 7.2 with CsOH and 330 mOsm/L. The free internal $Ca^{2+}$ concentration was buffered to 1 μM, according to the WCabuf software. The automated electrophysiological platform QPatch 16 from Sophion (Denmark) was used to carry out the compounds profiling. The series resistance and quality of seals were continuously monitored during the experiments. Data were analyzed using Sophion QPatch assay software 5.6 (Odense). Data were normalized using the maximum activation obtained during the pre-compound agonist application as the top value (1.0) and maximum inhibition induced by ML-204 as the bottom value (0.0). IC50 values were calculated using a least squares regression algorithm (Hill equation).

To monitor the ion currents, a voltage ramp from −100 mV to +100 mV, over 300 ms, was applied every 10 seconds, from a holding potential of −60 mV. Antagonist-mode: After recording for a minimum of 60 seconds control period, the EC60 concentration of the TRPC5 agonist, Rosiglitazone (30 μM), was applied to activate the channel. After reaching steady-state, co-application of increasing concentrations of test compound were applied followed by two applications of Rosiglitazone EC60 and a saturating concentration of the specific blocker ML-204 (100 μM).

III. FLIPR Protocol:

Compounds were made up to, or supplied as a 10 mM stock solution generally using DMSO as the vehicle. 10-point dose response curves were generated using the Echo-550 acoustic dispenser. Compound source plates were made by serially diluting compound stocks to create 10 mM, 1 mM, and 0.1 mM solutions in DMSO into Echo certified LDV plates. The Echo then serially spotted 100% DMSO stock solutions into source dose response plates to generate a 4-fold dilution scheme. 100% DMSO was added to the spotted dose response plates to bring the final volume to 5 μl. 300 μl of the dose response stock plate was then spotted into pre-incubation and stimulation assay plates. 50 μl of pre-incubation buffer and 100 μl of stimulation buffer was then added to the plates resulting in a final assay test concentration range of 30 μM to 0.0001 μM with a final DMSO concentration of 0.3%.

Human ICLN-1633 cells expressing were plated onto 384 well, black poly-D-lysine-coated microplates and maintained in TRPC5 growth media the day prior to use for experiments. TRPC5 expression was induced by the application of 1 μg/mL tetracycline at the time of plating. Media was removed from the plates and 10 g of 4 μM of Fluo-4 AM (mixed with equal volume of Pluronic F-127) in Earls's Balanced Salt Solution (EBSS) was added to the cells. Cells were incubated at room temperature, protected from light, for 60-90 minutes. After the incubation period, the dye was removed and replaced with 10 μl of EBSS. Cell, pre-incubation and stimulation plates were loaded onto the FLIPR-II and the assay was initiated. The FLIPR measured a 10 second baseline and then added 10 μl of 2× compounds (or controls). Changes in fluorescence were monitored for an additional 5 minutes. After the 5 minute pre-incubation, 20 μl of 2× riluzole (with 1× compound or controls) was added to the cell plate. The final riluzole stimulation concentration in the assay was 30 μM. After the riluzole addition, changes in fluorescence were monitored for an additional 5 minutes. Reduction in the riluzole-activated calcium response relative to control wells was reported as inhibition. A compound-mediated increase in the riluzole response relative to control riluzole response (no test agent present) with no enhancement of calcium entry during preincubation phase was reported as an agonist response.

Compound inhibition of TRPC5 calcium response was determined as follows. After the riluzole addition, fluorescence was monitored for a 5-minute period. For inhibition, the maximum relative fluorescence response (minus the control response of 1 μM of an internal control compound known to maximally block TRPC5 calcium response, the "REF INHIB" in the formula below) was captured and exported from the FLIPR.

Compound inhibition is calculated using the following formula:

$$\% \text{ inhibition} = \frac{RFU \text{ TEST AGENT} - \text{Plate Average } RFU \text{ REF INHIB}}{\text{Plate Average } RFU \text{ CONTROL} - \text{Plate Average } RFU \text{ REF INHIB}} \times 100$$

wherein "RFU" is the relative fluorescent units.

Compound activation (agonism) of TRPC5 calcium response was determined as follows. After the initial compound addition, fluorescence was monitored for 5 minutes. The maximum relative fluorescence response (minus the control response of EBSS buffer alone) is captured and exported from the FLIPR. Compound activation is calculated using the following formula:

$$\% \text{ activation} = \frac{RFU \text{ TEST AGENT} - \text{Plate Average } RFU \text{ Buffer}}{\text{Plate Average } RFU \text{ Riluzole CONTROL} - \text{Plate Average } RFU \text{ Buffer}} \times 100$$

Example 3: Exemplary Biological Assay Data

Potency Range:
QPatch assay: A=0.001-1 μM; B=1-30 μM; C=>30 μM; ND=not tested.
FLIPR assay (Inhibitor and Agonist activity): A=0.001-1 μM; B=1-10 μM; C=>10 μM; D=tested with a positive result for agonism, but $EC_{50}$ not calculated; ND=not tested.

Enantiomeric pairs indicated in Table 2 (see, e.g., Compounds 6 and 7; Compounds 12 and 13; Compounds 15 and 16, etc.) have relative stereochemistry to one another. In other words, the two enantiomers were separated from a racemic mixture, but the absolute stereochemistry of each has not been determined.

TABLE 2

QPatch, FLIPR Inhibitor and FLIPR Agonist potency ranges for representative compounds of the disclosure.

| Compound | Structure | Qpatch Potency Range | Inhibitor Potency Range | Agonist Potency Range |
|---|---|---|---|---|
| 1 | 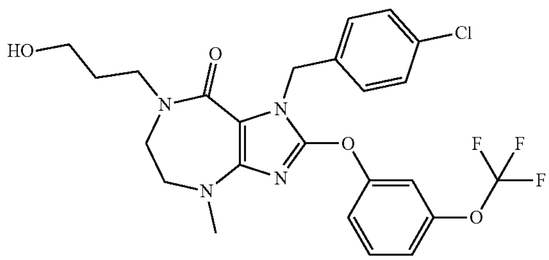 [SMILES: CN1CCN(CCCO)C(=O)c2c1nc(Oc1cccc(OC(F)(F)F)c1)n2Cc1ccc(Cl)cc1] | B | ND | ND |
| 2 | 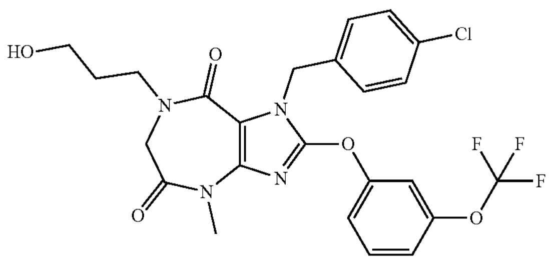 [SMILES: CN1C(=O)CN(CCCO)C(=O)c2c1nc(Oc1cccc(OC(F)(F)F)c1)n2Cc1ccc(Cl)cc1] | B | B | ND |
| 3 | 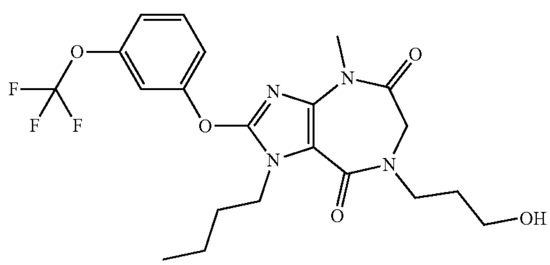 [SMILES: CCCCn1c(Oc2cccc(OC(F)(F)F)c2)nc2c1C(=O)N(CCCO)CC(=O)N2C] | ND | B | ND |
| 4 | 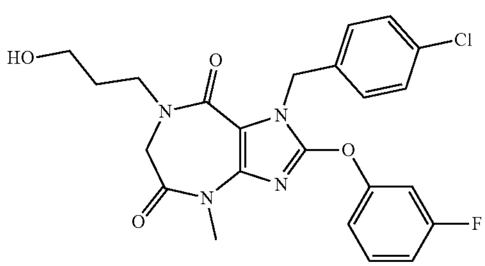 [SMILES: CN1C(=O)CN(CCCO)C(=O)c2c1nc(Oc1cccc(F)c1)n2Cc1ccc(Cl)cc1] | ND | B | ND |
| 5 | 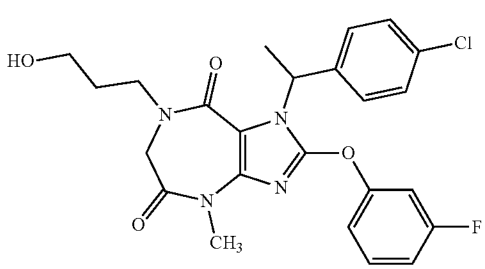 [SMILES: CC(c1ccc(Cl)cc1)n1c(Oc2cccc(F)c2)nc2c1C(=O)N(CCCO)CC(=O)N2C] | ND | ND | ND |

TABLE 2-continued

QPatch, FLIPR Inhibitor and FLIPR Agonist potency ranges for representative compounds of the disclosure.

| Compound | Structure | Qpatch Potency Range | Inhibitor Potency Range | Agonist Potency Range |
|---|---|---|---|---|
| 6 | 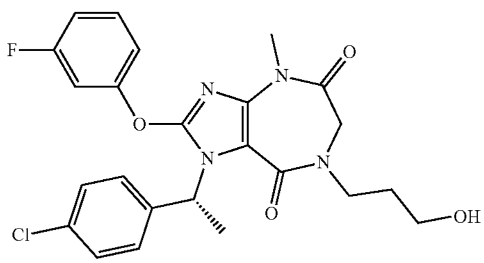 [SMILES: C[C@H](c1ccc(Cl)cc1)n1c(Oc2cccc(F)c2)nc2c1C(=O)N(CCCO)CC(=O)N2C] | C | C | ND |
| 7 | 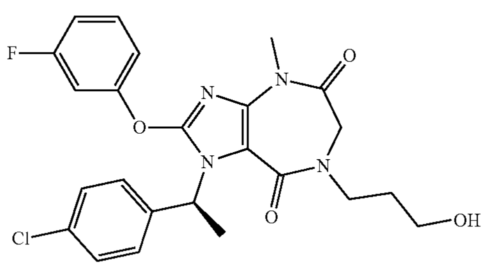 [SMILES: C[C@@H](c1ccc(Cl)cc1)n1c(Oc2cccc(F)c2)nc2c1C(=O)N(CCCO)CC(=O)N2C] | B | C | ND |
| 8 | 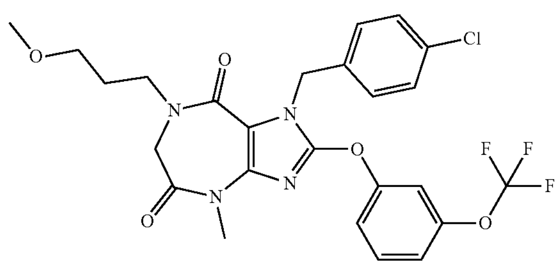 [SMILES: COCCCN1CC(=O)N(C)c2nc(Oc3cccc(OC(F)(F)F)c3)n(Cc3ccc(Cl)cc3)c2C1=O] | ND | B | ND |
| 9 | 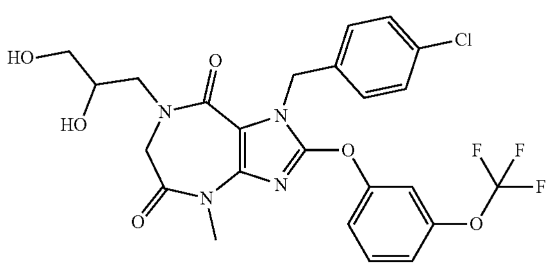 [SMILES: CN1C(=O)CN(CC(O)CO)C(=O)c2c1nc(Oc1cccc(OC(F)(F)F)c1)n2Cc1ccc(Cl)cc1] | B | ND | ND |
| 10 | 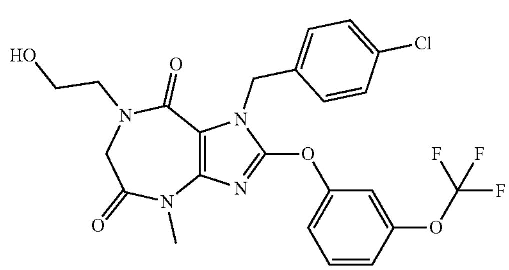 [SMILES: CN1C(=O)CN(CCO)C(=O)c2c1nc(Oc1cccc(OC(F)(F)F)c1)n2Cc1ccc(Cl)cc1] | ND | B | ND |

TABLE 2-continued
QPatch, FLIPR Inhibitor and FLIPR Agonist potency ranges for representative compounds of the disclosure.
| Compound | Structure | Qpatch Potency Range | Inhibitor Potency Range | Agonist Potency Range |
|---|---|---|---|---|
| 11 | 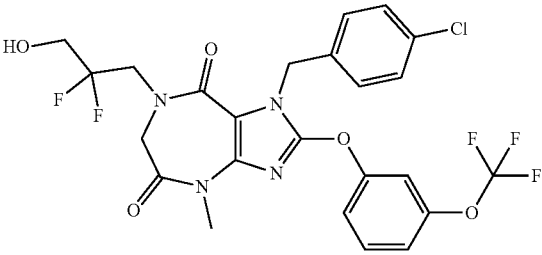 [SMILES: CN1C(=O)CN(CC(F)(F)CO)C(=O)c2c1nc(Oc1cccc(OC(F)(F)F)c1)n2Cc1ccc(Cl)cc1] | C | B | ND |
| 12 | 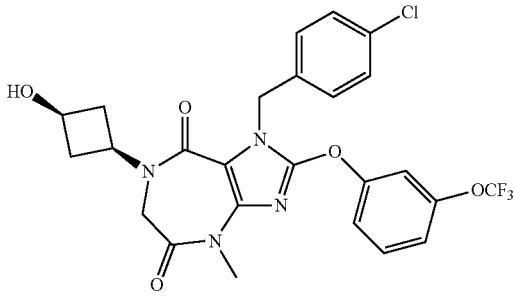 [SMILES: CN1C(=O)CN([C@H]2C[C@@H](O)C2)C(=O)c2c1nc(Oc1cccc(OC(F)(F)F)c1)n2Cc1ccc(Cl)cc1] | ND | ND | ND |
| 13 | 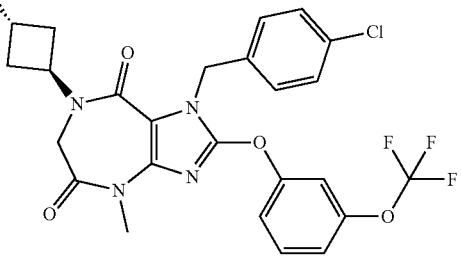 | B | ND | ND |
| 14 | 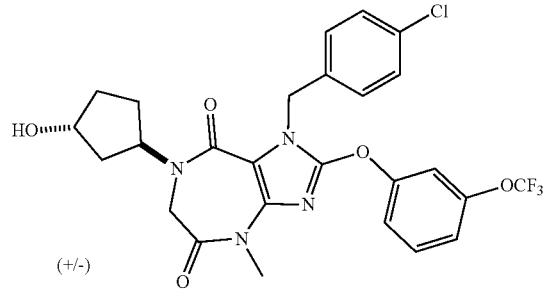 | ND | ND | ND |
| 15 | 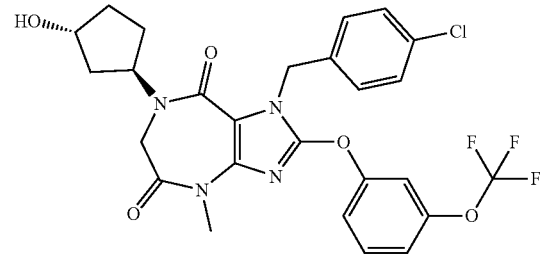 [SMILES: CN1C(=O)CN([C@@H]2CC[C@@H](O)C2)C(=O)c2c1nc(Oc1cccc(OC(F)(F)F)c1)n2Cc1ccc(Cl)cc1] | ND | A | ND |

TABLE 2-continued
QPatch, FLIPR Inhibitor and FLIPR Agonist potency ranges for representative compounds of the disclosure.
| Compound | Structure | Qpatch Potency Range | Inhibitor Potency Range | Agonist Potency Range |
|---|---|---|---|---|
| 16 | 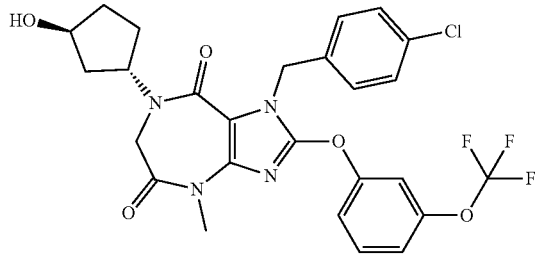 [SMILES: CN1C(=O)CN([C@H]2CC[C@H](O)C2)C(=O)c2c1nc(Oc1cccc(OC(F)(F)F)c1)n2Cc1ccc(Cl)cc1] | ND | B | ND |
| 17 | 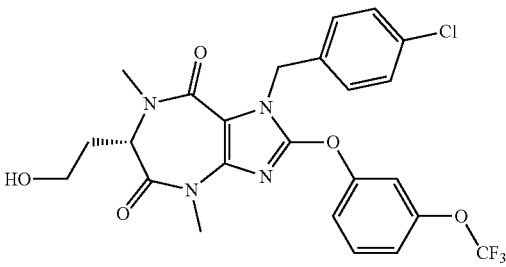 [SMILES: CN1C(=O)[C@H](CCO)N(C)C(=O)c2c1nc(Oc1cccc(OC(F)(F)F)c1)n2Cc1ccc(Cl)cc1] | C | ND | ND |
| 18 | 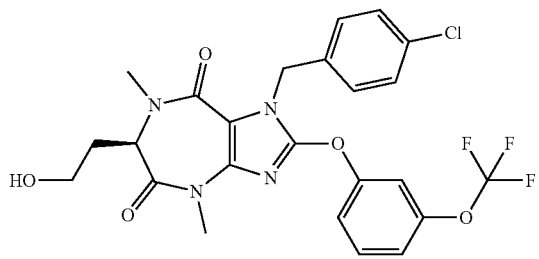 [SMILES: CN1C(=O)[C@@H](CCO)N(C)C(=O)c2c1nc(Oc1cccc(OC(F)(F)F)c1)n2Cc1ccc(Cl)cc1] | A | C | ND |
| 19 | 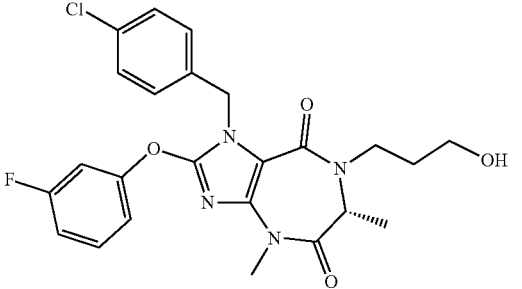 [SMILES: C[C@@H]1C(=O)N(C)c2nc(Oc3cccc(F)c3)n(Cc3ccc(Cl)cc3)c2C(=O)N1CCCO] | C | C | D |
| 20 | 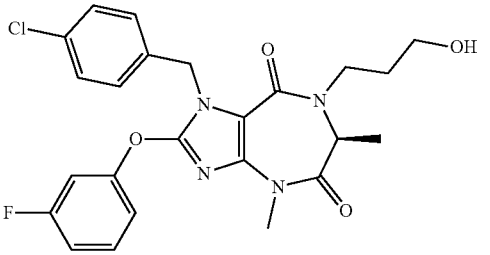 [SMILES: C[C@H]1C(=O)N(C)c2nc(Oc3cccc(F)c3)n(Cc3ccc(Cl)cc3)c2C(=O)N1CCCO] | B | A | ND |

TABLE 2-continued

QPatch, FLIPR Inhibitor and FLIPR Agonist potency ranges for representative compounds of the disclosure.

| Compound | Structure | Qpatch Potency Range | Inhibitor Potency Range | Agonist Potency Range |
|---|---|---|---|---|
| 21 | 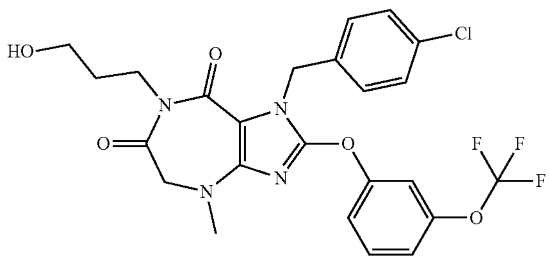 [SMILES: CN1CC(=O)N(CCCO)C(=O)c2c1nc(Oc1cccc(OC(F)(F)F)c1)n2Cc1ccc(Cl)cc1] | B | A | C |
| 22 | 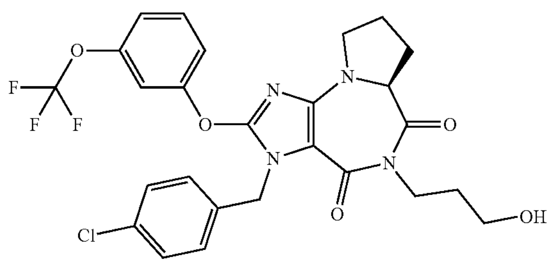 [SMILES: O=C1c2c(nc(Oc3cccc(OC(F)(F)F)c3)n2Cc2ccc(Cl)cc2)N2CCC[C@H]2C(=O)N1CCCO] | C | C | B |
| 23 | 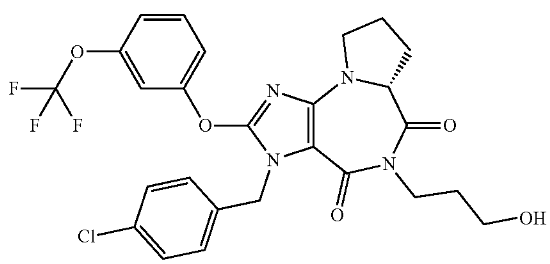 [SMILES: O=C1c2c(nc(Oc3cccc(OC(F)(F)F)c3)n2Cc2ccc(Cl)cc2)N2CCC[C@@H]2C(=O)N1CCCO] | B | A | C |
| 24 | 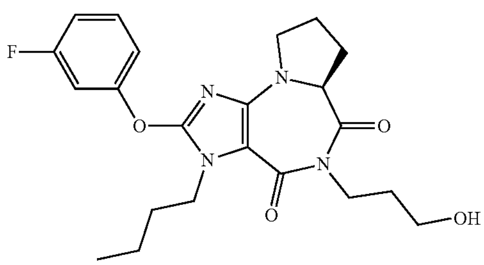 [SMILES: CCCCn1c(Oc2cccc(F)c2)nc2c1C(=O)N(CCCO)C(=O)[C@@H]1CCCN21] | A | A | ND |
| 25 | 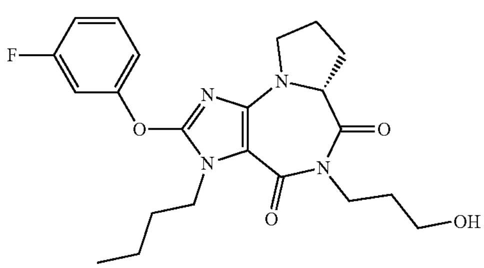 [SMILES: CCCCn1c(Oc2cccc(F)c2)nc2c1C(=O)N(CCCO)C(=O)[C@H]1CCCN21] | ND | C | D |

TABLE 2-continued
QPatch, FLIPR Inhibitor and FLIPR Agonist potency ranges for representative compounds of the disclosure.
| Compound | Structure | Qpatch Potency Range | Inhibitor Potency Range | Agonist Potency Range |
|---|---|---|---|---|
| 26 | 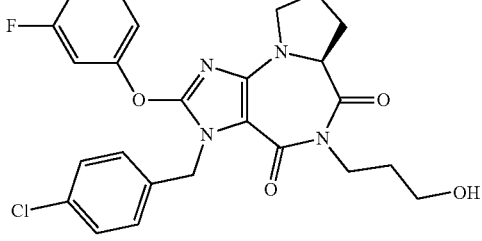 | ND | A | ND |
| 27 | 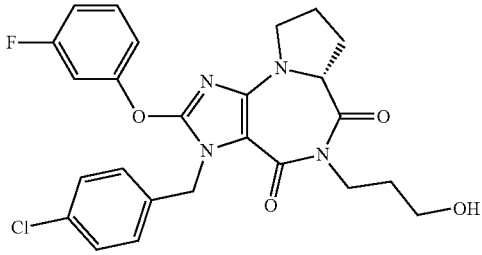 [SMILES: O=C1c2c(nc(Oc3cccc(F)c3)n2Cc2ccc(Cl)cc2)N2CCC[C@@H]2C(=O)N1CCCO] | ND | C | A |
| 28 | 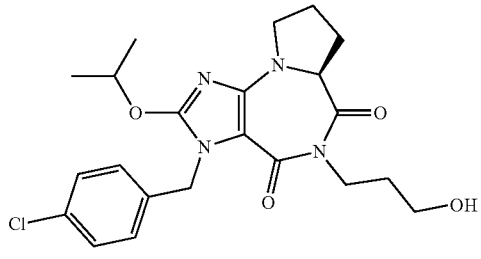 [SMILES: CC(C)Oc1nc2c(n1Cc1ccc(Cl)cc1)C(=O)N(CCCO)C(=O)[C@@H]1CCCN21] | ND | C | A |
| 29 | 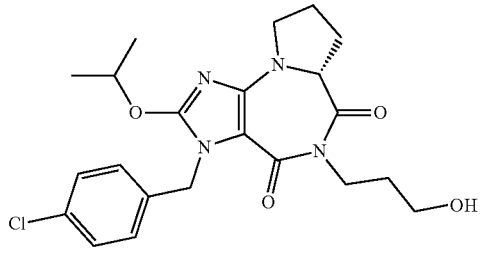 [SMILES: CC(C)Oc1nc2c(n1Cc1ccc(Cl)cc1)C(=O)N(CCCO)C(=O)[C@H]1CCCN21] | ND | C | B |
| 30 | 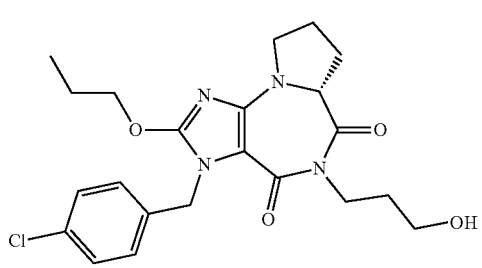 [SMILES: CCCOc1nc2c(n1Cc1ccc(Cl)cc1)C(=O)N(CCCO)C(=O)[C@H]1CCCN21] | ND | C | B |

TABLE 2-continued

QPatch, FLIPR Inhibitor and FLIPR Agonist potency ranges for representative compounds of the disclosure.

| Compound | Structure | Qpatch Potency Range | Inhibitor Potency Range | Agonist Potency Range |
|---|---|---|---|---|
| 31 | 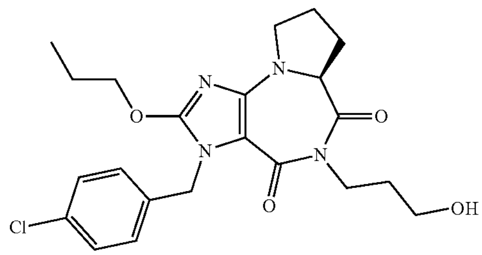 [SMILES: CCCOc1nc2c(n1Cc1ccc(Cl)cc1)C(=O)N(CCCO)C(=O)[C@@H]1CCCN21] | ND | C | A |
| 32 | 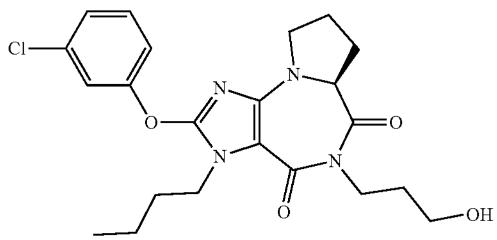 [SMILES: CCCCn1c(Oc2cccc(Cl)c2)nc2c1C(=O)N(CCCO)C(=O)[C@@H]1CCCN21] | ND | A | ND |
| 33 | 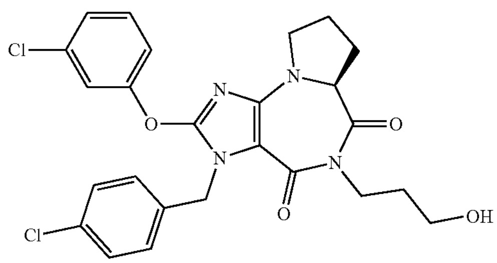 [SMILES: O=C1c2c(nc(Oc3cccc(Cl)c3)n2Cc2ccc(Cl)cc2)N2CCC[C@H]2C(=O)N1CCCO] | ND | A | ND |
| 34 | 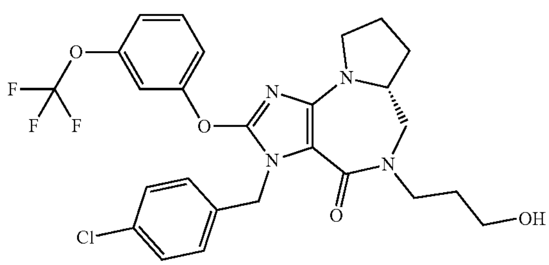 [SMILES: O=C1c2c(nc(Oc3cccc(OC(F)(F)F)c3)n2Cc2ccc(Cl)cc2)N2CCC[C@@H]2CN1CCCO] | ND | A | ND |
| 35 | 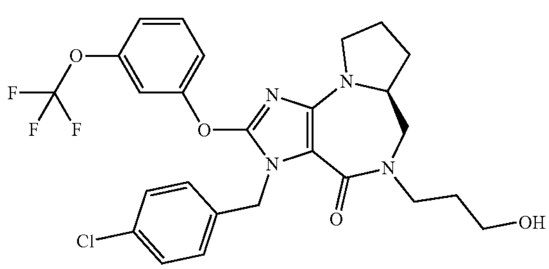 [SMILES: O=C1c2c(nc(Oc3cccc(OC(F)(F)F)c3)n2Cc2ccc(Cl)cc2)N2CCC[C@H]2CN1CCCO] | ND | B | ND |

TRPC5 Plasmid Sequence
The DNA sequence of the TRPC5 plasmid used in Example 2 is included below. Underlined nucleic acids represent those encoding human TRPC5.

SEQ ID NO: 1

GACGGATCGGGAGATCTCCCGATCCCCTATGGTGCACTCTCAGTACAATCTGCTCTG

ATGCCGCATAGTTAAGCCAGTATCTGCTCCCTGCTTGTGTGTTGGAGGTCGCTGAGT

AGTGCGCGAGCAAAATTTAAGCTACAACAAGGCAAGGCTTGACCGACAATTGCATG

AAGAATCTGCTTAGGGTTAGGCGTTTTGCGCTGCTTCGCGATGTACGGGCCAGATAT

ACGCGTTGACATTGATTATTGACTAGTTATTAATAGTAATCAATTACGGGGTCATTA

GTTCATAGCCCATATATGGAGTTCCGCGTTACATAACTTACGGTAAATGGCCCGCCT

GGCTGACCGCCCAACGACCCCCGCCCATTGACGTCAATAATGACGTATGTTCCCATA

GTAACGCCAATAGGGACTTTCCATTGACGTCAATGGGTGGAGTATTTACGGTAAACT

GCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTT

CCTACTTGGCAGTACATCTACGTATTAGTCATCGCTATTACCATGGTGATGCGGTTTT

GGCAGTACATCAATGGGCGTGGATAGCGGTTTGACTCACGGGGATTTCCAAGTCTCC

ACCCCATTGACGTCAATGGGAGTTTGTTTTGGCACCAAAATCAACGGGACTTTCCAA

AATGTCGTAACAACTCCGCCCCATTGACGCAAATGGGCGGTAGGCGTGTACGGTGG

GAGGTCTATATAAGCAGAGCTCTCCCTATCAGTGATAGAGATCTCCCTATCAGTGAT

AGAGATCGTCGACGAGCTCGTTTAGTGAACCGTCAGATCGCCTGGAGACGCCATCC

ACGCTGTTTTGACCTCCATAGAAGACACCGGGACCGATCCAGCCTCCGGACTCTAGC

GTTTAAACTTAAGCCCAAGCTGGCTAGACCGCC<u>ATGGCCCAACTGTACTACAAAAA</u>

<u>GGTCAACTACTCACCGTACAGAGACCGCATCCCCCTGCAAATTGTGAGGGCTGAGA</u>

<u>CAGAGCTCTCTGCAGAGGAGAAGGCCTTCCTCAATGCTGTGGAGAAGGGGGACTAT</u>

<u>GCCACTGTGAAGCAGGCCCTTCAGGAGGCTGAGATCTACTATAATGTTAACATCAAC</u>

<u>TGCATGGACCCCTTGGGCCGGAGTGCCCTGCTCATTGCCATTGAGAACGAGAACCTG</u>

<u>GAGATCATGGAGCTACTGCTGAACCACAGCGTGTATGTGGGTGATGCATTGCTCTAT</u>

<u>GCCATACGCAAGGAAGTGGTGGGCGCTGTGGAGCTTCTGCTCAGCTACAGGCGGCC</u>

<u>CAGCGGAGAGAAGCAGGTCCCCACTCTGATGATGGACACGCAGTTCTCTGAATTCA</u>

<u>CACCGGACATCACTCCCATCATGCTGGCTGCCCACACCAACAACTACGAAATCATCA</u>

<u>AACTGCTTGTCCAAAAACGGGTCACTATCCCACGGCCCCACCAGATCCGCTGCAACT</u>

<u>GTGTGGAGTGTGTGTCTAGTTCAGAGGTAGACAGCCTGCGCCACTCTCGCTCCCGAC</u>

<u>TGAACATCTATAAGGCTCTGGCAAGCCCCTCACTCATTGCCTTATCAAGTGAGGACC</u>

<u>CCATCCTAACTGCCTTCCGTCTGGGCTGGGAGCTCAAGGAGCTCAGCAAGGTGGAG</u>

<u>AATGAGTTCAAGGCCGAGTATGAGGAGCTCTCTCAGCAGTGCAAGCTCTTTGCCAAA</u>

<u>GACCTGCTGGACCAAGCTCGGAGCTCCAGGGAACTGGAGATCATCCTCAACCATCG</u>

<u>AGATGACCACAGTGAAGAGCTTGACCCTCAGAAGTACCATGACCTGGCCAAGTTGA</u>

<u>AGGTGGCAATCAAATACCACCAGAAAGAGTTTGTTGCTCAGCCCAACTGCCAACAG</u>

<u>TTGCTTGCCACCCTGTGGTATGATGGCTTCCCTGGATGGCGGCGGAAACACTGGGTA</u>

<u>GTCAAGCTTCTAACCTGCATGACCATTGGGTTCCTGTTTCCCATGCTGTCTATAGCCT</u>

<u>ACCTGATCTCACCCAGGAGCAACCTTGGGCTGTTCATCAAGAAACCCTTTATCAAGT</u>

<u>TTATCTGCCACACAGCATCCTATTTGACCTTCCTCTTTATGCTTCTCCTGGCTTCTCAG</u>

<u>CACATTGTCAGGACAGACCTTCATGTACAGGGGCCTCCCCCAACTGTCGTGGAATGG</u>

-continued

ATGATATTGCCTTGGGTTCTAGGTTTCATTTGGGGTGAGATTAAGGAAATGTGGGAT

GGTGGATTTACTGAATACATCCATGACTGGTGGAACCTGATGGATTTTGCAATGAAC

TCCCTCTACCTGGCAACTATTTCCCTGAAGATTGTGGCCTATGTCAAGTATAATGGTT

CTCGTCCAAGGGAGGAATGGGAAATGTGGCACCCGACTCTGATTGCGGAAGCACTC

TTCGCAATATCCAACATTTTAAGTTCGTTGCGTCTCATATCCCTGTTCACAGCCAACT

CCCACTTAGGACCTCTGCAGATCTCTTTGGGACGCATGCTGCTTGATATCCTCAAATT

CCTCTTTATCTACTGCCTGGTACTACTAGCTTTTGCCAATGGACTGAACCAGCTTTAC

TTCTATTATGAAACCAGAGCTATCGATGAGCCTAACAACTGCAAGGGGATCCGATGT

GAGAAACAGAACAATGCCTTCTCCACGCTCTTTGAGACTCTTCAGTCACTCTTCTGG

TCTGTATTTGGCCTTTTAAATCTATATGTCACCAATGTGAAAGCCAGACACGAATTC

ACCGAGTTTGTAGGAGCTACCATGTTTGGAACATACAATGTCATCTCCCTGGTAGTG

CTGCTGAACATGCTGATTGCTATGATGAACAACTCCTATCAGCTTATTGCCGATCAT

GCTGATATCGAGTGGAAGTTTGCAAGGACGAAGCTCTGGATGAGTTACTTTGATGAA

GGTGGCACCTTGCCACCTCCTTTCAACATCATCCCCAGCCCCAAGTCATTTCTATACC

TTGGTAACTGGTTCAACAACACCTTCTGCCCCAAAAGAGACCCTGACGGTAGACGG

AGAAGGCGCAACTTGAGAAGTTTCACAGAACGCAATGCTGACAGCCTGATACAAAA

TCAACATTATCAGGAAGTTATCAGGAATTTAGTCAAAAGATATGTGGCTGCTATGAT

AAGAAATTCCAAAACACATGAGGGACTTACAGAAGAAAATTTTAAGGAATTAAAGC

AAGACATCTCCAGCTTTCGGTATGAAGTGCTTGACCTCTTGGGAAATAGAAAACATC

CAAGGAGCTTTTCCACTAGCAGCACTGAACTGTCTCAGAGAGACGATAATAATGAT

GGCAGTGGTGGGGCTCGGGCCAAATCCAAGAGTGTCTCTTTTAATTTAGGCTGCAAG

AAAAAGACTTGCCATGGGCCACCTCTCATCAGAACCATGCCAAGGTCCAGTGGTGC

CCAAGGAAAGTCAAAAGCTGAGTCATCAAGCAAACGCTCCTTCATGGGTCCTTCTCT

CAAGAAACTGGGTCTCCTATTCTCCAAATTTAATGGTCATATGTCTGAACCCAGTTC

AGAGCCAATGTACACAATTTCTGATGGAATTGTTCAGCAGCACTGTATGTGGCAGGA

CATCAGATATTCTCAGATGGAGAAAGGGAAAGCAGAGGCCTGTTCTCAAAGTGAAA

TTAACCTCAGTGAGGTAGAATTAGGTGAAGTCCAGGGCGCTGCTCAGAGCAGTGAA

TGCCCTCTAGCCTGTTCCAGCTCTCTTCACTGTGCATCCAGCATCTGCTCCTCAAATT

CTAAACTTTTAGACTCCTCAGAGGATGTATTTGAAACTTGGGGAGAGGCTTGTGACT

TGCTCATGCACAAATGGGGTGATGGACAGGAAGAACAAGTTACAACTCGCCTCTAA

TGACTCGAGTCTAGAGGGCCCGTTTAAACCCGCTGATCAGCCTCGACTGTGCCTTCT

AGTTGCCAGCCATCTGTTGTTTGCCCCTCCCCCGTGCCTTCCTTGACCCTGGAAGGTG

CCACTCCCACTGTCCTTTCCTAATAAAATGAGGAAATTGCATCGCATTGTCTGAGTA

GGTGTCATTCTATTCTGGGGGGTGGGGTGGGCAGGACAGCAAGGGGAGGATTGG

GAAGACAATAGCAGGCATGCTGGGGATGCGGTGGGCTCTATGGCTTCTGAGGCGGA

AAGAACCAGCTGGGGCTCTAGGGGGTATCCCCACGCGCCCTGTAGCGGCGCATTAA

GCGCGGCGGGTGTGGTGGTTACGCGCAGCGTGACCGCTACACTTGCCAGCGCCCTA

GCGCCCGCTCCTTTCGCTTTCTTCCCTTCCTTTCTCGCCACGTTCGCCGGCTTTCCCCG

TCAAGCTCTAAATCGGGGGCTCCCTTTAGGGTTCCGATTTAGTGCTTTACGGCACCTC

GACCCCAAAAAACTTGATTAGGGTGATGGTTCACGTAGTGGGCCATCGCCCTGATAG

-continued

```
ACGGTTTTTCGCCCTTTGACGTTGGAGTCCACGTTCTTTAATAGTGGACTCTTGTTCC

AAACTGGAACAACACTCAACCCTATCTCGGTCTATTCTTTTGATTTATAAGGGATTTT

GCCGATTTCGGCCTATTGGTTAAAAAATGAGCTGATTTAACAAAAATTTAACGCGAA

TTAATTCTGTGGAATGTGTGTCAGTTAGGGTGTGGAAAGTCCCCAGGCTCCCCAGCA

GGCAGAAGTATGCAAAGCATGCATCTCAATTAGTCAGCAACCAGGTGTGGAAAGTC

CCCAGGCTCCCCAGCAGGCAGAAGTATGCAAAGCATGCATCTCAATTAGTCAGCAA

CCATAGTCCCGCCCCTAACTCCGCCCATCCCGCCCCTAACTCCGCCCAGTTCCGCCC

ATTCTCCGCCCCATGGCTGACTAATTTTTTTATTTATGCAGAGGCCGAGGCCGCCTC

TGCCTCTGAGCTATTCCAGAAGTAGTGAGGAGGCTTTTTGGAGGCCTAGGCTTTTG

CAAAAAGCTCCCGGGAGCTTGTATATCCATTTTCGGATCTGATCAGCACGTGATGAA

AAAGCCTGAACTCACCGCGACGTCTGTCGAGAAGTTTCTGATCGAAAAGTTCGACA

GCGTCTCCGACCTGATGCAGCTCTCGGAGGGCGAAGAATCTCGTGCTTTCAGCTTCG

ATGTAGGAGGGCGTGGATATGTCCTGCGGGTAAATAGCTGCGCCGATGGTTTCTACA

AAGATCGTTATGTTTATCGGCACTTTGCATCGGCCGCGCTCCCGATTCCGGAAGTGC

TTGACATTGGGGAATTCAGCGAGAGCCTGACCTATTGCATCTCCCGCCGTGCACAGG

GTGTCACGTTGCAAGACCTGCCTGAAACCGAACTGCCCGCTGTTCTGCAGCCGGTCG

CGGAGGCCATGGATGCGATCGCTGCGGCCGATCTTAGCCAGACGAGCGGGTTCGGC

CCATTCGGACCGCAAGGAATCGGTCAATACACTACATGGCGTGATTTCATATGCGCG

ATTGCTGATCCCCATGTGTATCACTGGCAAACTGTGATGGACGACACCGTCAGTGCG

TCCGTCGCGCAGGCTCTCGATGAGCTGATGCTTTGGGCCGAGGACTGCCCCGAAGTC

CGGCACCTCGTGCACGCGGATTTCGGCTCCAACAATGTCCTGACGGACAATGGCCGC

ATAACAGCGGTCATTGACTGGAGCGAGGCGATGTTCGGGGATTCCCAATACGAGGT

CGCCAACATCTTCTTCTGGAGGCCGTGGTTGGCTTGTATGGAGCAGCAGACGCGCTA

CTTCGAGCGGAGGCATCCGGAGCTTGCAGGATCGCCGCGGCTCCGGGCGTATATGC

TCCGCATTGGTCTTGACCAACTCTATCAGAGCTTGGTTGACGGCAATTTCGATGATG

CAGCTTGGGCGCAGGGTCGATGCGACGCAATCGTCCGATCCGGAGCCGGGACTGTC

GGGCGTACACAAATCGCCCGCAGAAGCGCGGCCGTCTGGACCGATGGCTGTGTAGA

AGTACTCGCCGATAGTGGAAACCGACGCCCCAGCACTCGTCCGAGGGCAAAGGAAT

AGCACGTGCTACGAGATTTCGATTCCACCGCCGCCTTCTATGAAAGGTTGGGCTTCG

GAATCGTTTTCCGGGACGCCGGCTGGATGATCCTCCAGCGCGGGGATCTCATGCTGG

AGTTCTTCGCCCACCCCAACTTGTTTATTGCAGCTTATAATGGTTACAAATAAAGCA

ATAGCATCACAAATTTCACAAATAAAGCATTTTTTTCACTGCATTCTAGTTGTGGTTT

GTCCAAACTCATCAATGTATCTTATCATGTCTGTATACCGTCGACCTCTAGCTAGAGC

TTGGCGTAATCATGGTCATAGCTGTTTCCTGTGTGAAATTGTTATCCGCTCACAATTC

CACACAACATACGAGCCGGAAGCATAAAGTGTAAAGCCTGGGGTGCCTAATGAGTG

AGCTAACTCACATTAATTGCGTTGCGCTCACTGCCCGCTTTCCAGTCGGGAAACCTG

TCGTGCCAGCTGCATTAATGAATCGGCCAACGCGCGGGGAGAGGCGGTTTGCGTATT

GGGCGCTCTTCCGCTTCCTCGCTCACTGACTCGCTGCGCTCGGTCGTTCGGCTGCGGC

GAGCGGTATCAGCTCACTCAAAGGCGGTAATACGGTTATCCACAGAATCAGGGGAT

AACGCAGGAAAGAACATGTGAGCAAAAGGCCAGCAAAAGGCCAGGAACCGTAAAA

AGGCCGCGTTGCTGGCGTTTTTCCATAGGCTCCGCCCCCCTGACGAGCATCACAAAA
```

```
ATCGACGCTCAAGTCAGAGGTGGCGAAACCCGACAGGACTATAAAGATACCAGGCG

TTTCCCCCTGGAAGCTCCCTCGTGCGCTCTCCTGTTCCGACCCTGCCGCTTACCGGAT

ACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCC

CGTTCAGCCCGACCGCTGCGCCTTATCCGGTAACTATCGTCTTGAGTCCAACCCGGT

AAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTA

GAAGAACAGTATTTGGTATCTGCGCTCTGCTGAAGCCAGTTACCTTCGGAAAAAGAG

TTGGTAGCTCTTGATCCGGCAAACAAACCACCGCTGGTAGCGGTTGGTTTTTTGTTTG

CAAGCAGCAGATTACGCGCAGAAAAAAAGGATCTCAAGAAGATCCTTTGATCTTTT

CTACGGGGTCTGACGCTCAGTGGAACGAAAACTCACGTTAAGGGATTTTGGTCATGA

GATTATCAAAAAGGATCTTCACCTAGATCCTTTTAAATTAAAAATGAAGTTTTAAAT

CAATCTAAAGTATATATGAGTAAACTTGGTCTGACAGTTACCAATGCTTAATCAGTG

AGGCACCTATCTCAGCGATCTGTCTATTTCGTTCATCCATAGTTGCCTGACTCCCCGT

CGTGTAGATAACTACGATACGGGAGGGCTTACCATCTGGCCCCAGTGCTGCAATGAT

ACCGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTATTA

ATTGTTGCCGGGAAGCTAGAGTAAGTAGTTCGCCAGTTAATAGTTTGCGCAACGTTG

TTGCCATTGCTACAGGCATCGTGGTGTCACGCTCGTCGTTTGGTATGGCTTCATTCAG

CTCCGGTTCCCAACGATCAAGGCGAGTTACATGATCCCCCATGTTGTGCAAAAAAGC

GGTTAGCTCCTTCGGTCCTCCGATCGTTGTCAGAAGTAAGTTGGCCGCAGTGTTATC

ACTCATGGTTATGGCAGCACTGCATAATTCTCTTACTGTCATGCCATCCGTAAGATG

CTTTTCTGTGACTGGTGAGTACTCAACCAAGTCATTCTGAGAATAGTGTATGCGGCG

ACCGAGTTGCTCTTGCCCGGCGTCAATACGGGATAATACCGCGCCACATAGCAGAA

CTTTAAAAGTGCTCATCATTGGAAAACGTTCTTCGGGGCGAAAACTCTCAAGGATCT

TACCGCTGTTGAGATCCAGTTCGATGTAACCCACTCGTGCACCCAACTGATCTTCAG

CATCTTTTACTTTCACCAGCGTTTCTGGGTGAGCAAAAACAGGAAGGCAAAATGCCG

CAAAAAAGGGAATAAGGGCGACACGGAAATGTTGAATACTCATACTCTTCCTTTTTC

AATATTATTGAAGCATTTATCAGGGTTATTGTCTCATGAGCGGATACATATTTGAAT

GTATTTAGAAAAATAAACAAATAGGGGTTCCGCGCACATTTCCCCGAAAAGTGCCA

CCTGACGTC
```

INCORPORATION BY REFERENCE

All of the U.S. patents and U.S. and PCT published patent applications cited herein are hereby incorporated by reference.

EQUIVALENTS

The foregoing written specification is sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The invention claimed is:

1. A compound of Formula (II), or a tautomer or a pharmaceutically acceptable salt thereof,

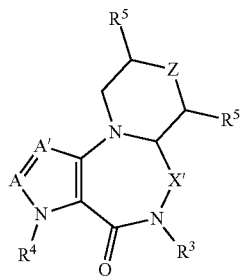

wherein
A' is N, and A is CR; or A is N, and A' is CR;
R is L-R$^1$;
L is O, CH$_2$, SO$_2$, or NR$^2$, or is absent;
R$^1$ is selected from optionally substituted alkyl, optionally substituted aryl, and optionally substituted heteroaryl, and when L is absent, R$^1$ is additionally selected from H;
each R$^2$ is independently alkyl or H;
R$^3$ is selected from optionally substituted alkyl, optionally substituted alkylene-OR$^2$, optionally substituted cycloalkylene-OR$^2$, optionally substituted alkylene-N(R$^7$)$_2$, optionally substituted cycloalkylene-N(R$^7$)$_2$, optionally substituted alkylene-C(O)N(R$^2$)$_2$, optionally substituted cycloalkylene-C(O)N(R$^2$)$_2$, optionally substituted alkylene-S(O)$_2$N(R$^2$)$_2$, and optionally substituted cycloalkylene-S(O)$_2$N(R$^2$)$_2$;
R$^4$ is selected from optionally substituted alkylene-aryl, alkyl, and optionally substituted alkylene-heteroaryl;
each R$^5$ is independently selected from H, N(R$^2$)$_2$, OR$^2$;
each R$^7$ is independently selected from H, alkyl, (alkyl)C(O)—, (aryl)C(O)—, (alkyl)S(O)$_2$—, and (aryl)S(O)$_2$—;
X' is —C(O)—, CH$_2$, CHR$^{3'}$, or C(R$^{3'}$)$_2$;
each R$^{3'}$ is independently selected from optionally substituted alkyl, optionally substituted alkylene-OR$^2$, optionally substituted cycloalkylene-OR$^2$, optionally substituted alkylene-N(R$^7$)$_2$, optionally substituted cycloalkylene-N(R$^7$)$_2$, optionally substituted alkylene-C(O)N(R$^2$)$_2$, optionally substituted cycloalkylene-C(O)N(R$^2$)$_2$, optionally substituted alkylene-S(O)$_2$N(R$^2$)$_2$, and optionally substituted cycloalkylene-S(O)$_2$N(R$^2$)$_2$; and
Z is absent.

2. The compound of claim 1, wherein A is CR and A' is N.

3. The compound of claim 1, wherein L is O.

4. The compound of claim 1, wherein R$^1$ is phenyl substituted with one or more substituents independently selected from halogen, —CF$_3$, —C(H)F$_2$, and —OCF$_3$.

5. The compound of claim 1, wherein R$^1$ is optionally substituted alkyl.

6. The compound of claim 1, wherein R$^3$ is optionally substituted alkylene-OH.

7. The compound of claim 6, wherein R$^3$ is selected from

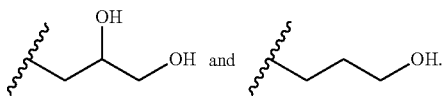 [SMILES: *CC(O)CO ; *CCCO]

8. The compound of claim 1, wherein each R$^5$ is H.

9. The compound of claim 1, wherein the compound is selected from:

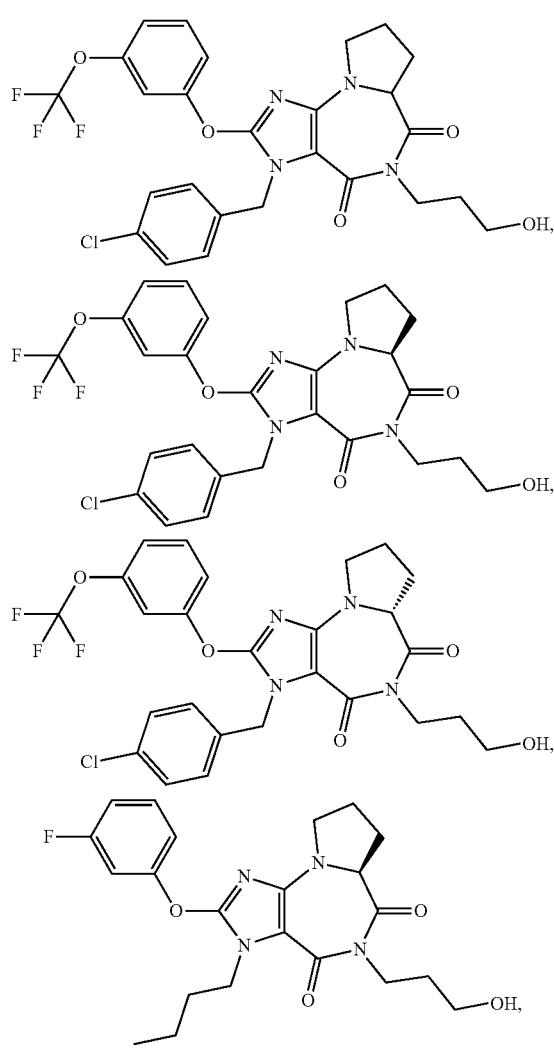

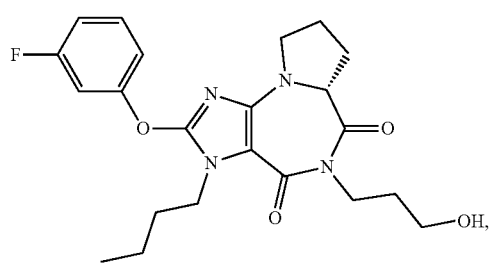

-continued
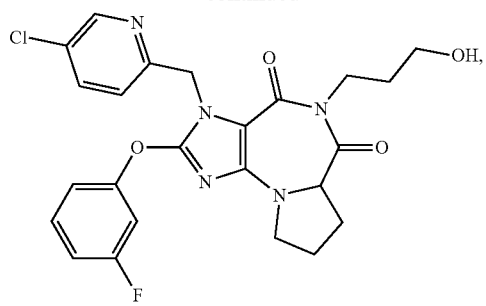
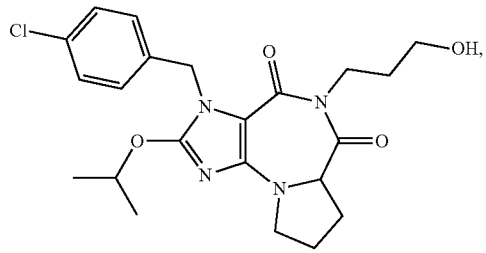
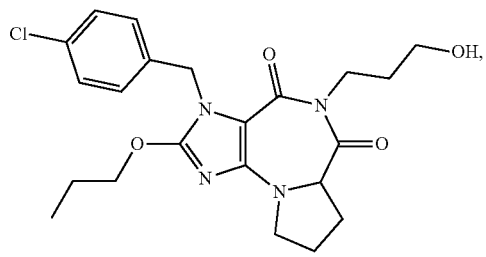
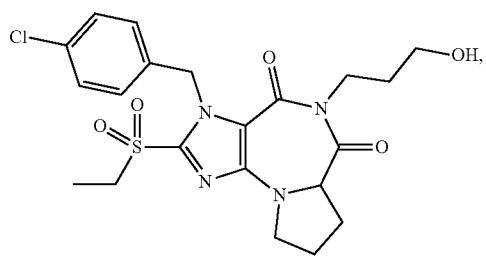
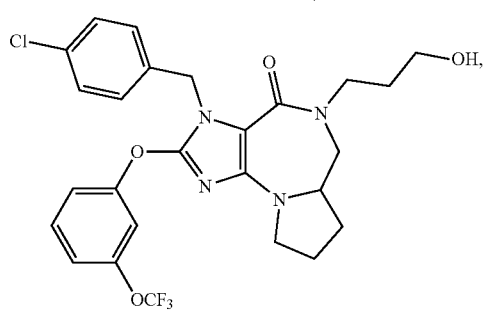
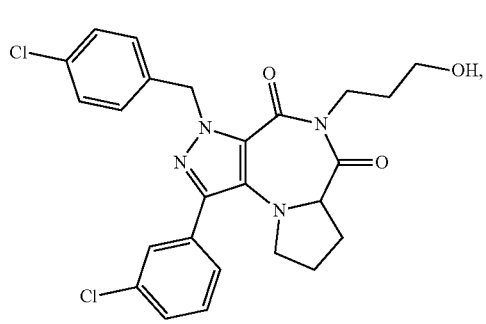
-continued
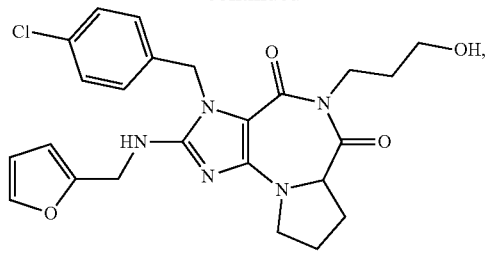
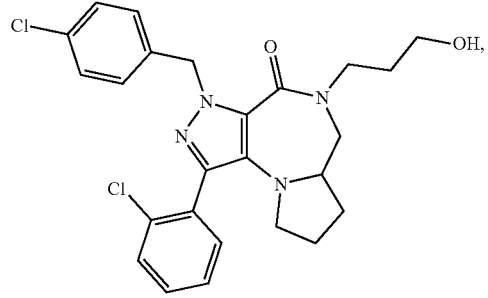
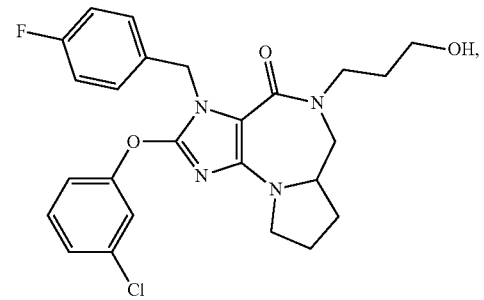
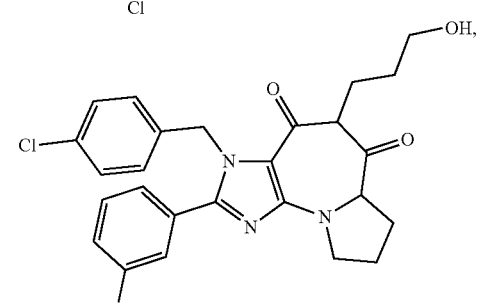
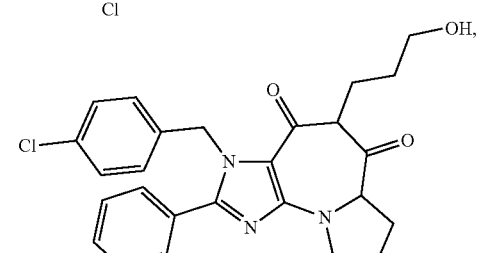
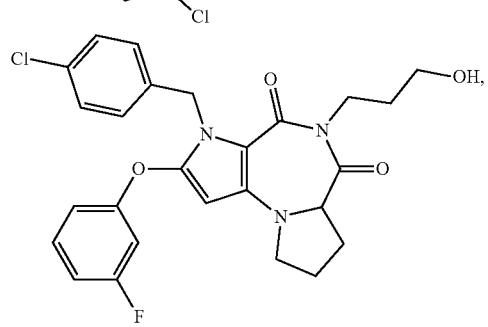

117
-continued
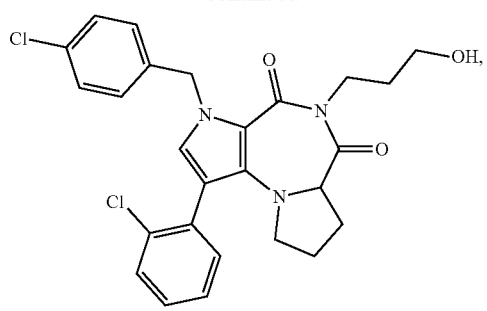
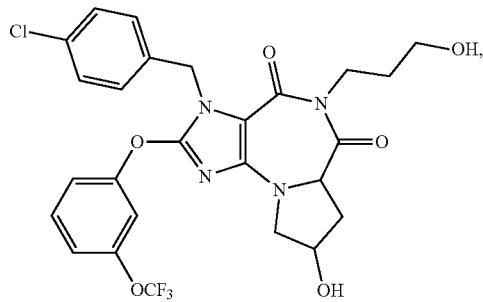
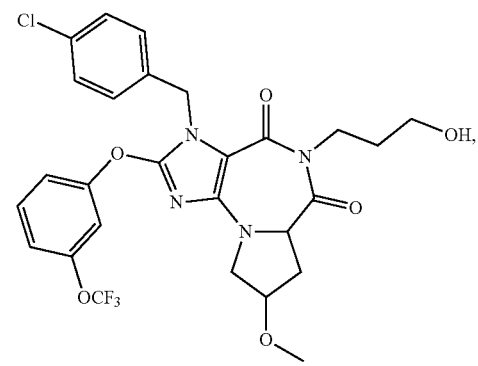
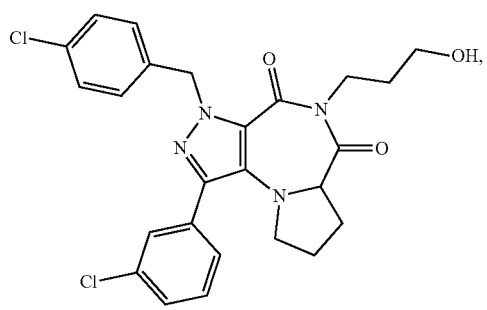
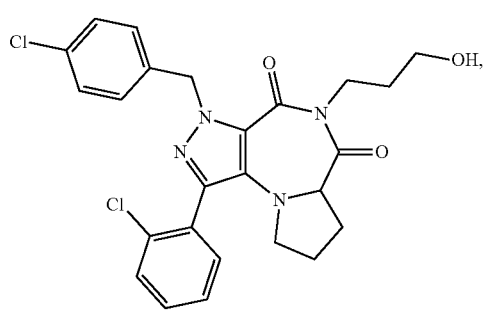
118
-continued
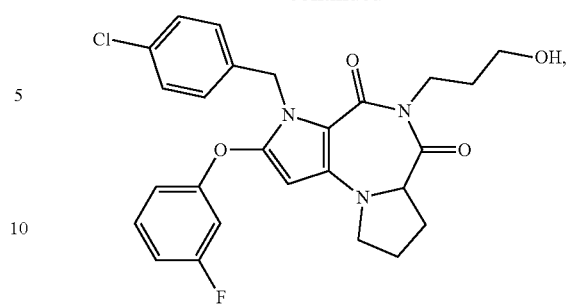
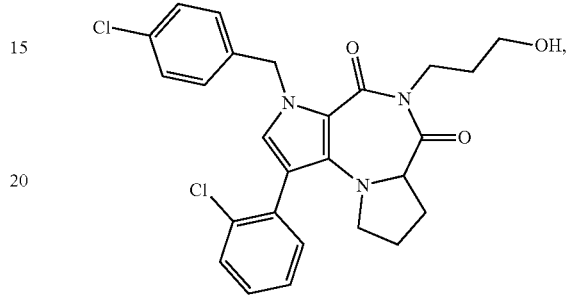
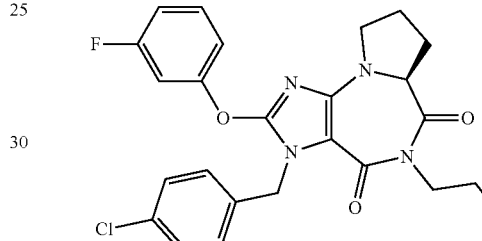
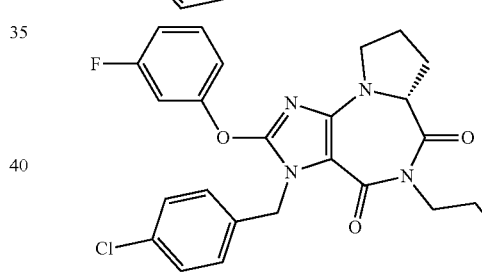
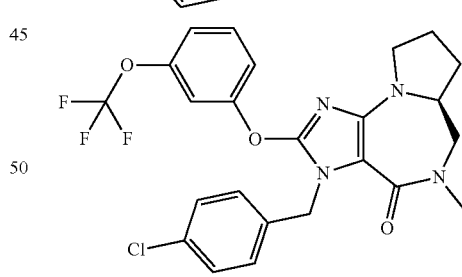
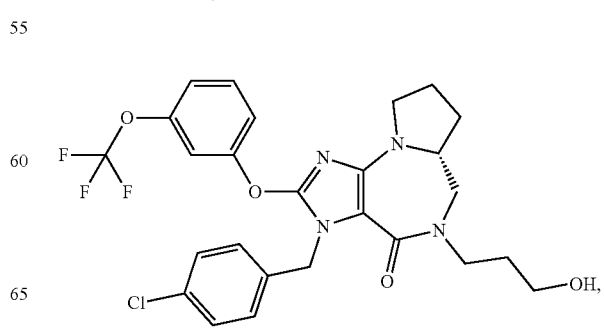

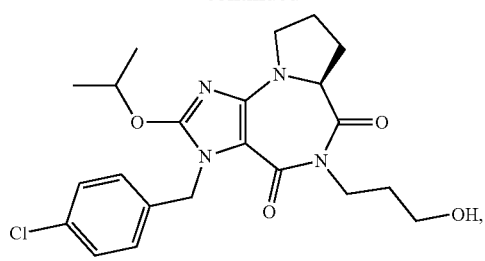
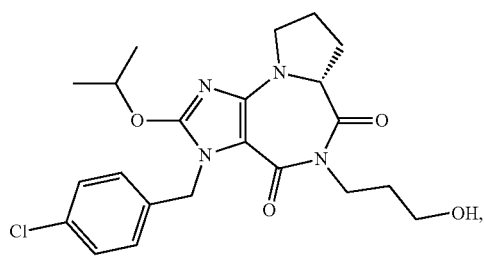
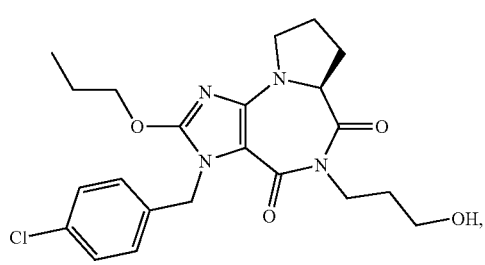
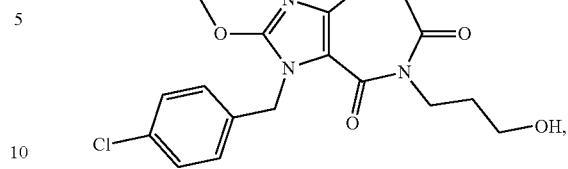
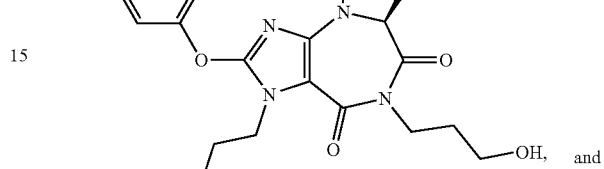
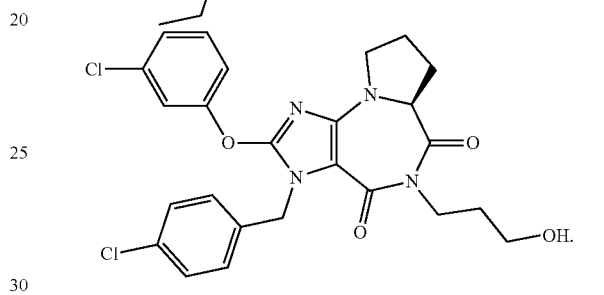
10. A composition, comprising a compound of claim 1 or a tautomer or a pharmaceutically acceptable salt thereof, and a pharmaceutically acceptable excipient.
\* \* \* \* \*

SEQUENCE LISTING

<160> NUMBER OF SEQ ID NOS: 1

<210> SEQ ID NO 1
<211> LENGTH: 8541
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg    780
gtaggcgtgt acggtgggag gtctatataa gcagagctct ccctatcagt gatagagatc    840
tccctatcag tgatagagat cgtcgacgag ctcgtttagt gaaccgtcag atcgcctgga    900
gacgccatcc acgctgtttt gacctccata aagacaccg gaccgatcc agcctccgga    960
ctctagcgtt taaacttaag cccaagctgg ctagaccgcc atggcccaac tgtactacaa   1020
aaaggtcaac tactcaccgt acagagaccg catcccctg caaattgtga gggctgagac   1080
agagctctct gcagaggaga aggccttcct caatgctgtg gagaagggg actatgccac   1140
tgtgaagcag gcccttcagg aggctgagat ctactataat gttaacatca actgcatgga   1200
ccccttgggc cggagtgccc tgctcattgc cattgagaac gagaacctgg agatcatgga   1260
gctactgctg aaccacagcg tgtatgtggg tgatgcattg ctctatgcca tacgcaagga   1320
agtggtgggc gctgtggagc ttctgctcag ctacaggcgg cccagcggag agaagcaggt   1380
cccccactctg atgatggaca cgcagttctc tgaattcaca ccggacatca ctcccatcat   1440
gctggctgcc cacaccaaca actacgaaat catcaaactg cttgtccaaa acgggtcac   1500
tatcccacgg ccccaccaga tccgctgcaa ctgtgtggag tgtgtgtcta gttcagaggt   1560
agacagcctg cgccactctc gctcccgact gaacatctat aaggctctgg caagcccctc   1620
actcattgcc ttatcaagtg aggacccca cctaactgcc ttccgtctgg gctgggagct   1680
caaggagctc agcaaggtgg agaatgagtt caaggccgag tatgaggagc tctctcagca   1740
gtgcaagctc tttgccaaag acctgctgga ccaagctcgg agctccaggg aactggagat   1800
catcctcaac catcgagatg accacagtga agagcttgac cctcagaagt accatgacct   1860
ggccaagttg aaggtggcaa tcaaatacca ccagaaagag tttgttgctc agcccaactg   1920
ccaacagttg cttgccaccc tgtggtatga tggcttccct ggatggcggc ggaaacactg   1980
```

```
ggtagtcaag cttctaacct gcatgaccat tgggttcctg tttcccatgc tgtctatagc    2040
ctacctgatc tcacccagga gcaaccttgg gctgttcatc aagaaaccct ttatcaagtt    2100
tatctgccac acagcatcct atttgacctt cctctttatg cttctcctgg cttctcagca    2160
cattgtcagg acagaccttc atgtacaggg gcctcccca actgtcgtgg aatggatgat    2220
attgccttgg gttctaggtt tcatttgggg tgagattaag gaaatgtggg atggtggatt    2280
tactgaatac atccatgact ggtggaacct gatggatttt gcaatgaact ccctctacct    2340
ggcaactatt tccctgaaga ttgtggccta tgtcaagtat aatggttctc gtccaaggga    2400
ggaatgggaa atgtggcacc cgactctgat tgcggaagca ctcttcgcaa tatccaacat    2460
tttaagttcg ttgcgtctca tatccctgtt cacagccaac tcccacttag acctctgca    2520 gatctctttg ggacgcatgc tgcttgatat cctcaaattc ctctttatct actgcctggt    2580
actactagct tttgccaatg gactgaacca gctttacttc tattatgaaa ccagagctat    2640
cgatgagcct aacaactgca aggggatccg atgtgagaaa cagaacaatg ccttctccac    2700
gctctttgag actcttcagt cactcttctg gtctgtattt ggccttttaa atctatatgt    2760
caccaatgtg aaagccagac acgaattcac cgagtttgta ggagctacca tgtttggaac    2820
atacaatgtc atctccctgg tagtgctgct gaacatgctg attgctatga tgaacaactc    2880
ctatcagctt attgccgatc atgctgatat cgagtggaag tttgcaagga cgaagctctg    2940
gatgagttac tttgatgaag gtggcacctt gccacctcct ttcaacatca tccccagccc    3000
caagtcattt ctataccttg gtaactggtt caacaacacc ttctgcccca aagagaccc    3060 tgacggtaga cggagaaggc gcaacttgag aagtttcaca gaacgcaatg ctgacagcct    3120
gatacaaaat caacattatc aggaagttat caggaattta gtcaaaagat atgtggctgc    3180
tatgataaga aattccaaaa cacatgaggg acttacagaa gaaattttta aggaattaaa    3240
gcaagacatc tccagctttc ggtatgaagt gcttgacctc ttgggaaata gaaaacatcc    3300
aaggagcttt tccactagca gcactgaact gtctcagaga gacgataata atgatggcag    3360 tggtgggct cgggccaaat ccaagagtgt ctcttttaat ttaggctgca agaaaaagac    3420
ttgccatggg ccacctctca tcagaaccat gccaaggtcc agtggtgccc aaggaaagtc    3480
aaaagctgag tcatcaagca acgctccctt catgggtcct tctctcaaga aactgggtct    3540
cctattctcc aaatttaatg gtcatatgtc tgaacccagt tcagagccaa tgtacacaat    3600
ttctgatgga attgttcagc agcactgtat gtggcaggac atcagatatt ctcagatgga    3660
gaaagggaaa gcagaggcct gttctcaaag tgaaattaac ctcagtgagg tagaattagg    3720
tgaagtccag ggcgctgctc agagcagtga atgccctcta gcctgttcca gctctcttca    3780
ctgtgcatcc agcatctgct cctcaaattc taaacttta gactcctcag aggatgtatt    3840
tgaaacttgg ggagaggctt gtgacttgct catgcacaaa tggggtgatg acaggaaga    3900 acaagttaca actcgcctct aatgactcga gtctagaggg cccgtttaaa cccgctgatc    3960
agcctcgact gtgccttcta gttgccagcc atctgttgtt tgcccctccc ccgtgccttc    4020
cttgaccctg gaaggtgcca ctcccactgt cctttcctaa taaaatgagg aaattgcatc    4080
gcattgtctg agtaggtgtc attctattct ggggggtggg gtgggcagg acagcaaggg    4140 ggaggattgg gaagacaata gcaggcatgc tggggatgcg gtgggctcta tggcttctga    4200
ggcggaaaga accagctggg gctctagggg gtatccccac gcgccctgta gcggcgcatt    4260
aagcgcggcg ggtgtggtgg ttacgcgcag cgtgaccgct acacttgcca gcgccctagc    4320
gcccgctcct ttcgctttct tcccttcctt tctcgccacg ttcgccggct tccccgtca    4380
```

```
agctctaaat cgggggctcc ctttagggtt ccgatttagt gctttacggc acctcgaccc   4440
caaaaaactt gattagggtg atggttcacg tagtgggcca tcgccctgat agacggtttt   4500
tcgccctttg acgttggagt ccacgttctt taatagtgga ctcttgttcc aaactggaac   4560
aacactcaac cctatctcgg tctattcttt tgatttataa gggattttgc cgatttcggc   4620
ctattggtta aaaatgagc tgatttaaca aaatttaac gcgaattaat tctgtggaat    4680
gtgtgtcagt tagggtgtgg aaagtcccca ggctccccag caggcagaag tatgcaaagc   4740
atgcatctca attagtcagc aaccaggtgt ggaaagtccc caggctcccc agcaggcaga   4800
agtatgcaaa gcatgcatct caattagtca gcaaccatag tcccgcccct aactccgccc   4860
atcccgcccc taactccgcc cagttccgcc cattctccgc cccatggctg actaatttt    4920 tttatttatg cagaggccga ggccgcctct gcctctgagc tattccagaa gtagtgagga   4980
ggcttttttg gaggcctagg cttttgcaaa aagctcccgg gagcttgtat atccattttc   5040
ggatctgatc agcacgtgat gaaaaagcct gaactcaccg cgacgtctgt cgagaagttt   5100
ctgatcgaaa agttcgacag cgtctccgac ctgatgcagc tctcggaggg cgaagaatct   5160
cgtgctttca gcttcgatgt aggagggcgt ggatatgtcc tgcgggtaaa tagctgcgcc   5220
gatggtttct acaaagatcg ttatgtttat cggcactttg catcggccgc gctcccgatt   5280
ccggaagtgc ttgacattgg ggaattcagc gagagcctga cctattgcat ctccgccgt    5340 gcacagggtg tcacgttgca agacctgcct gaaaccgaac tgcccgctgt tctgcagccg   5400
gtcgcggagg ccatggatgc gatcgctgcg gccgatctta gccagacgag cgggttcggc   5460
ccattcggac cgcaaggaat cggtcaatac actacatggc gtgatttcat atgcgcgatt   5520
gctgatcccc atgtgtatca ctggcaaact gtgatggacg acaccgtcag tgcgtccgtc   5580
gcgcaggctc tcgatgagct gatgctttgg gccgaggact gccccgaagt ccggcacctc   5640
gtgcacgcgg atttcggctc caacaatgtc ctgacggaca atggccgcat aacagcggtc   5700
attgactgga gcgaggcgat gttcgggat tcccaatacg aggtcgccaa catcttcttc    5760
tggaggccgt ggttggcttg tatgagcag cagacgcgct acttcgagcg gaggcatccg    5820
gagcttgcag gatcgccgcg gctccgggcg tatatgctcc gcattggtct tgaccaactc   5880
tatcagagct tggttgacgg caatttcgat gatgcagctt gggcgcaggg tcgatgcgac   5940
gcaatcgtcc gatccggagc cgggactgtc gggcgtacac aaatcgcccg cagaagcgcg   6000
gccgtctgga ccgatggctg tgtagaagta ctcgccgata gtggaaaccg acgccccagc   6060
actcgtccga gggcaaagga atagcacgtg ctacgagatt tcgattccac cgccgccttc   6120
tatgaaaggt tgggcttcgg aatcgttttc cgggacgccg gctggatgat cctccagcgc   6180
ggggatctca tgctggagtt cttcgcccac cccaacttgt ttattgcagc ttataatggt   6240
tacaaataaa gcaatagcat cacaaatttc acaaataaag catttttttc actgcattct   6300
agttgtggtt tgtccaaact catcaatgta tcttatcatg tctgtatacc gtcgacctct   6360
agctagagct tggcgtaatc atggtcatag ctgtttcctg tgtgaaattg ttatccgctc   6420
acaattccac acaacatacg agccggaagc ataaagtgta aagcctgggg tgcctaatga   6480
gtgagctaac tcacattaat tgcgttgcgc tcactgcccg ctttccagtc gggaaacctg   6540
tcgtgccagc tgcattaatg aatcggccaa cgcgcgggga gaggcggttt gcgtattggg   6600
cgctcttccg cttcctcgct cactgactcg ctgcgctcgg tcgttcggct gcggcgagcg   6660
gtatcagctc actcaaaggc ggtaatacgg ttatccacag aatcagggga taacgcagga   6720
```

```
aagaacatgt gagcaaaagg ccagcaaaag gccaggaacc gtaaaaaggc cgcgttgctg      6780 gcgttttcc ataggctccg cccccctgac gagcatcaca aaaatcgacg ctcaagtcag       6840
aggtggcgaa acccgacagg actataaaga taccaggcgt ttccccctgg aagctccctc      6900
gtgcgctctc ctgttccgac cctgccgctt accggatacc tgtccgcctt tctcccttcg      6960
ggaagcgtgg cgctttctca tagctcacgc tgtaggtatc tcagttcggt gtaggtcgtt      7020
cgctccaagc tgggctgtgt gcacgaaccc cccgttcagc ccgaccgctg cgccttatcc      7080
ggtaactatc gtcttgagtc caacccggta agacacgact tatcgccact ggcagcagcc      7140
actggtaaca ggattagcag agcgaggtat gtaggcggtg ctacagagtt cttgaagtgg      7200
tggcctaact acggctacac tagaagaaca gtatttggta tctgcgctct gctgaagcca      7260
gttaccttcg gaaaaagagt tggtagctct tgatccggca acaaaccac cgctggtagc       7320 ggttggtttt ttgtttgcaa gcagcagatt acgcgcagaa aaaaggatc tcaagaagat       7380 cctttgatct tttctacggg gtctgacgct cagtggaacg aaaactcacg ttaagggatt      7440
ttggtcatga gattatcaaa aaggatcttc acctagatcc ttttaaatta aaatgaagt       7500 tttaaatcaa tctaaagtat atatgagtaa acttggtctg acagttacca atgcttaatc      7560
agtgaggcac ctatctcagc gatctgtcta tttcgttcat ccatagttgc ctgactcccc      7620
gtcgtgtaga taactacgat acgggagggc ttaccatctg gccccagtgc tgcaatgata      7680
ccgcgagacc cacgctcacc ggctccagat ttatcagcaa taaccagcc agccggaagg       7740 gccgagcgca gaagtggtcc tgcaacttta tccgcctcca tccagtctat taattgttgc      7800
cgggaagcta gagtaagtag ttcgccagtt aatagtttgc gcaacgttgt tgccattgct      7860
acaggcatcg tggtgtcacg ctcgtcgttt ggtatggctt cattcagctc cggttcccaa      7920
cgatcaaggc gagttacatg atcccccatg ttgtgcaaaa aagcggttag ctccttcggt      7980
cctccgatcg ttgtcagaag taagttggcc gcagtgttat cactcatggt tatggcagca      8040
ctgcataatt ctcttactgt catgccatcc gtaagatgct tttctgtgac tggtgagtac      8100
tcaaccaagt cattctgaga atagtgtatg cggcgaccga gttgctcttg cccggcgtca      8160
atacgggata ataccgcgcc acatagcaga actttaaaag tgctcatcat tggaaaacgt      8220 tcttcgggc gaaaactctc aaggatctta ccgctgttga gatccagttc gatgtaaccc       8280
actcgtgcac ccaactgatc ttcagcatct tttactttca ccagcgtttc tgggtgagca      8340
aaaacaggaa ggcaaaatgc cgcaaaaaag ggaataaggg cgacacggaa atgttgaata      8400
ctcatactct ccttttttca atattattga agcatttatc agggttattg tctcatgagc      8460
ggatacatat ttgaatgtat ttagaaaaat aaacaaatag gggttccgcg cacatttccc      8520
cgaaaagtgc cacctgacgt c                                                 8541
```